US012649897B2

(12) United States Patent
Strange et al.

(10) Patent No.: US 12,649,897 B2
(45) Date of Patent: Jun. 9, 2026

(54) BIOPROCESSING SYSTEM

(71) Applicant: Cellular Origins Limited, Melbourn (GB)

(72) Inventors: Daniel Strange, Royston (GB); Peter Crossley, Royston (GB); Martin Mottram, Royston (GB); Edwin Stone, Royston (GB); Leo Steenson, Royston (GB); Paul Crisp, Royston (GB); Lukas Stauskis, Royston (GB)

(73) Assignee: Cellular Origins Limited, Melbourn (GB)

( * ) Notice: Subject to any disclaimer, the term of this patent is extended or adjusted under 35 U.S.C. 154(b) by 0 days.

(21) Appl. No.: 18/182,114

(22) Filed: Mar. 10, 2023

(65) Prior Publication Data

US 2023/0203419 A1     Jun. 29, 2023

Related U.S. Application Data

(63) Continuation of application No. PCT/GB2022/051737, filed on Jul. 6, 2022.

(30) Foreign Application Priority Data

Jul. 6, 2021    (GB) ..................................... 2109779

(51) Int. Cl.
   *C12M 1/00*      (2006.01)
   *C12M 1/12*      (2006.01)
   *C12M 1/34*      (2006.01)

(52) U.S. Cl.
   CPC ............ *C12M 23/58* (2013.01); *C12M 23/50* (2013.01); *C12M 29/00* (2013.01); *C12M 37/04* (2013.01); *C12M 41/00* (2013.01)

(58) Field of Classification Search
   CPC ...... C12M 23/58; C12M 23/50; C12M 29/00; C12M 37/04; C12M 41/00; B25J 5/00;
          (Continued)

(56) References Cited

U.S. PATENT DOCUMENTS 4,369,779 A    1/1983   Spencer
4,619,642 A   10/1986   Spencer
        (Continued)

FOREIGN PATENT DOCUMENTS

CH         698798 B1    10/2009
CN    102862292 A   *   1/2013
        (Continued)

OTHER PUBLICATIONS

Published U.S. Appl. No. 63/196,029, by applicants/assignee Hodge. U.S. Appl. No. 63/196,029 was disclosed to the public on Aug. 1, 2024 as it was incorporated by reference into US Application Pub No. 20240252803 (Year: 2021) (Year: 2021).*
        (Continued)

*Primary Examiner* — Elizabeth A Robinson
*Assistant Examiner* — Tingchen Shi
(74) *Attorney, Agent, or Firm* — Foley & Lardner LLP

(57) ABSTRACT

A bioprocessing system comprising a series of processing stations for performing operations for bioprocessing is disclosed. The bioprocessing system includes an automated system comprising means for manipulating a fluid connection between a first container and a separable second container whereby to create an aseptic connection that enables a controlled transfer of fluid or cell material between the first container and the second container, wherein the means for manipulating a fluid connection is configured to create an aseptic connection that can be disconnected after the transfer of fluid or cell material is complete to enable a further such fluid connection to be manipulated between the first con- (Continued)

Cell washing and concentration      Activation, Transduction, Expansion      Fill finish tainer and a separable third container, and means for controlling an automated sequence of operation of the processing stations.

20 Claims, 56 Drawing Sheets

(58) Field of Classification Search
CPC ..... B25J 9/02; B25J 9/06; B25J 9/0087; B25J 9/043; G01N 23/2204; C12N 5/00; C12N 5/0636
See application file for complete search history.

(56) References Cited

U.S. PATENT DOCUMENTS

| | | | |
|---|---|---|---|
| 4,793,880 | A | 12/1988 | Shaposka et al. |
| 5,397,425 | A | 3/1995 | Ivansons et al. |
| 6,351,690 | B1* | 2/2002 | Lenz .................. G01N 35/0099 |
| | | | 435/468 |
| 9,783,768 | B2 | 10/2017 | Larcher et al. |
| 10,562,041 | B2 | 2/2020 | Camisani et al. |
| 10,906,180 | B1* | 2/2021 | Chefitz .................. B25J 9/0006 |
| 11,371,007 | B2 | 6/2022 | Griffin et al. |
| 2003/0141009 | A1 | 7/2003 | Landherr et al. |
| 2005/0194059 | A1* | 9/2005 | Py ............................. B65B 7/00 |
| | | | 141/18 |
| 2005/0239196 | A1 | 10/2005 | Yanai et al. |
| 2008/0023135 | A1 | 1/2008 | Ivansons et al. |
| 2014/0030802 | A1 | 1/2014 | Eberle et al. |
| 2016/0068793 | A1 | 3/2016 | Maggiore |
| 2017/0128905 | A1 | 5/2017 | Pighin et al. |
| 2017/0217027 | A1* | 8/2017 | Boucard ................ B25J 19/023 |
| 2019/0048303 | A1* | 2/2019 | Maggiore ............ B67D 3/0012 |
| 2019/0117888 | A1* | 4/2019 | Burkholz ............. G02B 27/017 |
| 2020/0025782 | A1 | 1/2020 | Ahlfors |
| 2021/0283606 | A1 | 9/2021 | Thakkar et al. |
| 2022/0143610 | A1 | 5/2022 | Biz et al. |
| 2024/0252803 | A1* | 8/2024 | Hodge ................... C12M 37/04 |

FOREIGN PATENT DOCUMENTS

| | | |
|---|---|---|
| DE | 102010060634 A1 | 5/2012 |
| EP | 0 442 04 A2 | 1/1982 |
| EP | 0357166 A1 | 3/1990 |
| EP | 0 507 321 A1 | 10/1992 |
| EP | 0 639 384 A2 | 2/1995 |
| EP | 0 847 847 A1 | 6/1998 |
| EP | 1 144 026 B1 | 7/2004 |
| EP | 1 652 653 A1 | 5/2006 |
| EP | 3252147 A1 | 12/2017 |
| EP | 3284815 A1 | 2/2018 |
| EP | 3792635 A1 | 3/2021 |
| EP | 3500862 B1 | 4/2021 |
| GB | 2095403 A | 9/1982 |
| JP | 2013-162965 A | 8/2013 |
| WO | WO-02/066098 A1 | 8/2002 |
| WO | 2008018904 A2 | 2/2008 |
| WO | WO-2015/152789 A1 | 10/2015 |
| WO | 2017098331 A1 | 6/2017 |
| WO | 2017203249 A1 | 11/2017 |
| WO | 2018148346 A1 | 8/2018 |
| WO | 2019071450 A1 | 4/2019 |
| WO | WO-2020/127570 A1 | 6/2020 |
| WO | WO-2021/183687 A2 | 9/2021 |
| WO | 2022256403 A1 | 12/2022 |
| WO | 2022256404 A1 | 12/2022 |
| WO | 2022261041 A1 | 12/2022 |
| WO | WO-2023/281258 A1 | 1/2023 |
| WO | 2023018902 A1 | 2/2023 |
| WO | WO-2023/187414 A1 | 10/2023 |

OTHER PUBLICATIONS

International Search Report for Application No. PCT/GB2022/051737 mailed Dec. 19, 2022, pp. 1-7.
Search Report for Application No. GB2109779.5 dated Aug. 6, 2021. 1 pg.
Combined Search and Examination Report for Application No. GB2303541.3 dated Apr. 24, 2023. 6 pgs.
Combined Search and Examination Report for Application No. GB2303543.9 dated Apr. 24, 2023. 6 pgs.
International Search Report for Application No. PCT/GB2022/051739 mailed Nov. 9, 2022, pp. 1-4.
Sartorius, "Biowelder Total Containment—Sartorius Stedim Biowelder® TC Operating Manual," Serial No. BWTC#2000; Sartorius Stedim Biotech GmbH, Goettingen, Germany; May 2021 (239 pages).
Sartorius, "Biowelder Total Containment—Sartorius Stedim Biowelder, TC Operating Manual," Serial No. BWTC#2000; https://www.youtube.com/watch?v=CV08EtVbdEE; Dated Jan. 7, 2015 (18 pages).
Wilson Wolf, "Future of T Cell Manufacturing Video," Wilson Wolf; https://www.wilsonwolf.com/future-of-t-cell-manufacturing-video/; published Dec. 12, 2016 (46 pages).

* cited by examiner

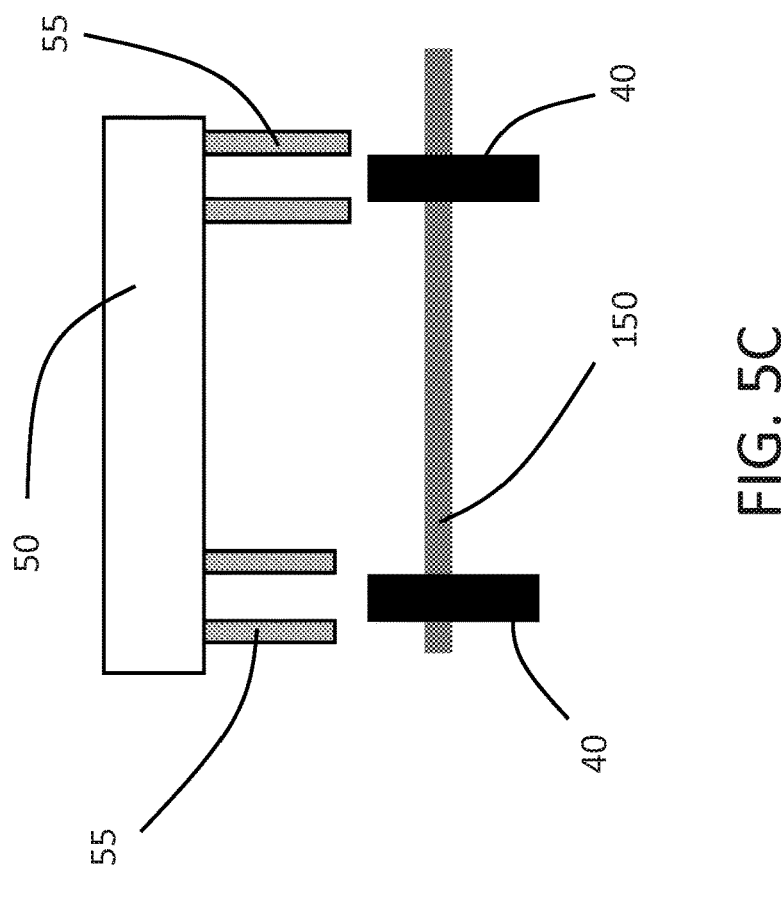
FIG. 5C
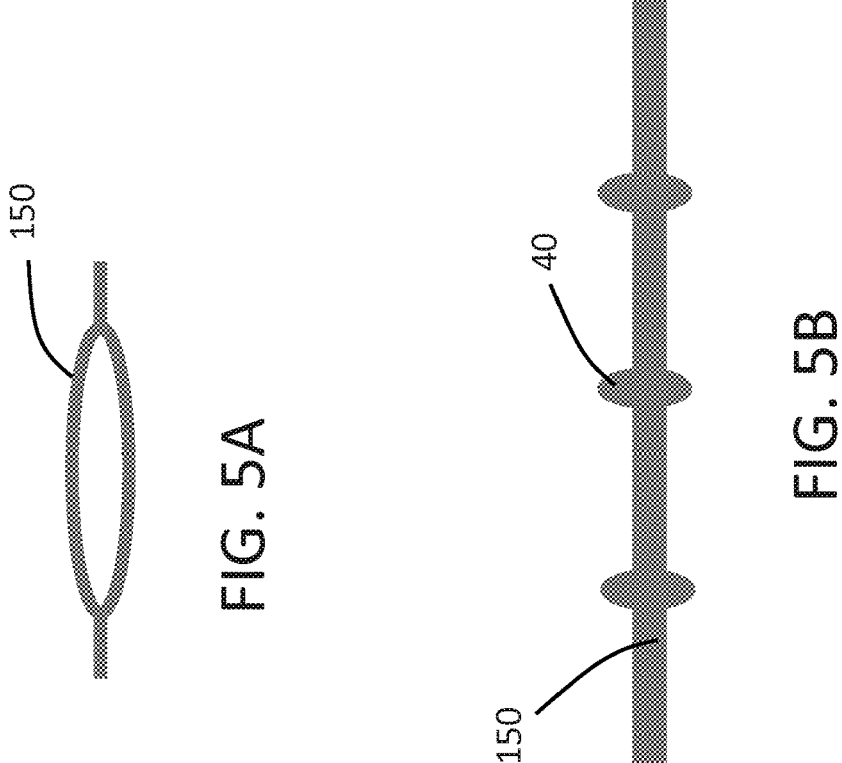
FIG. 5A
FIG. 5B

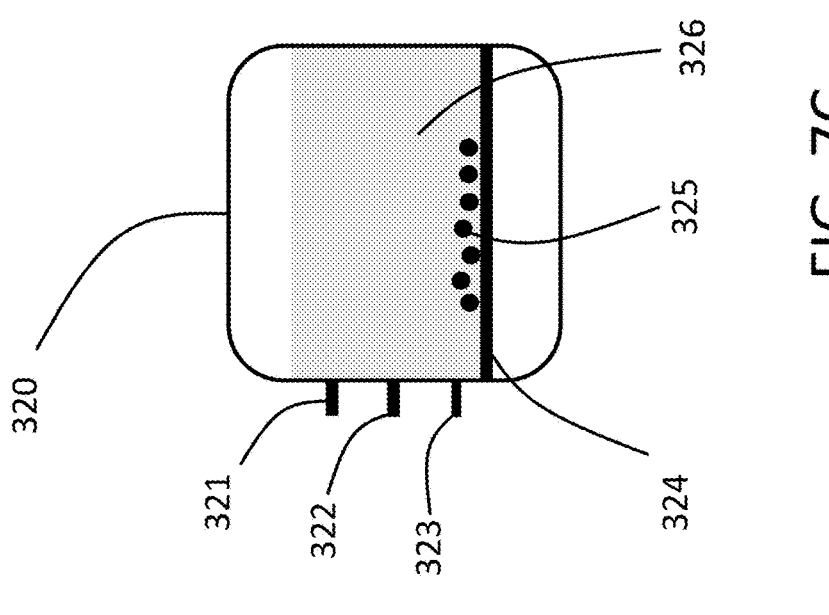
FIG. 7C
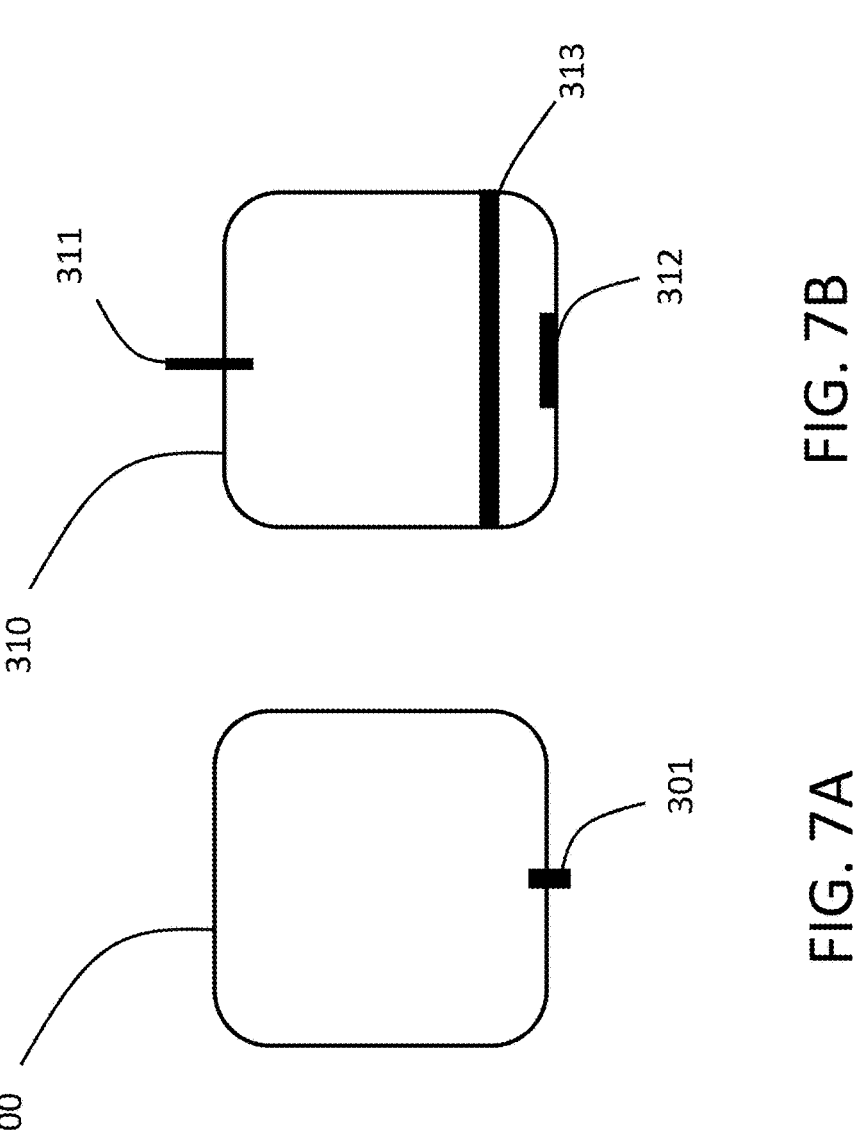
FIG. 7B
FIG. 7A

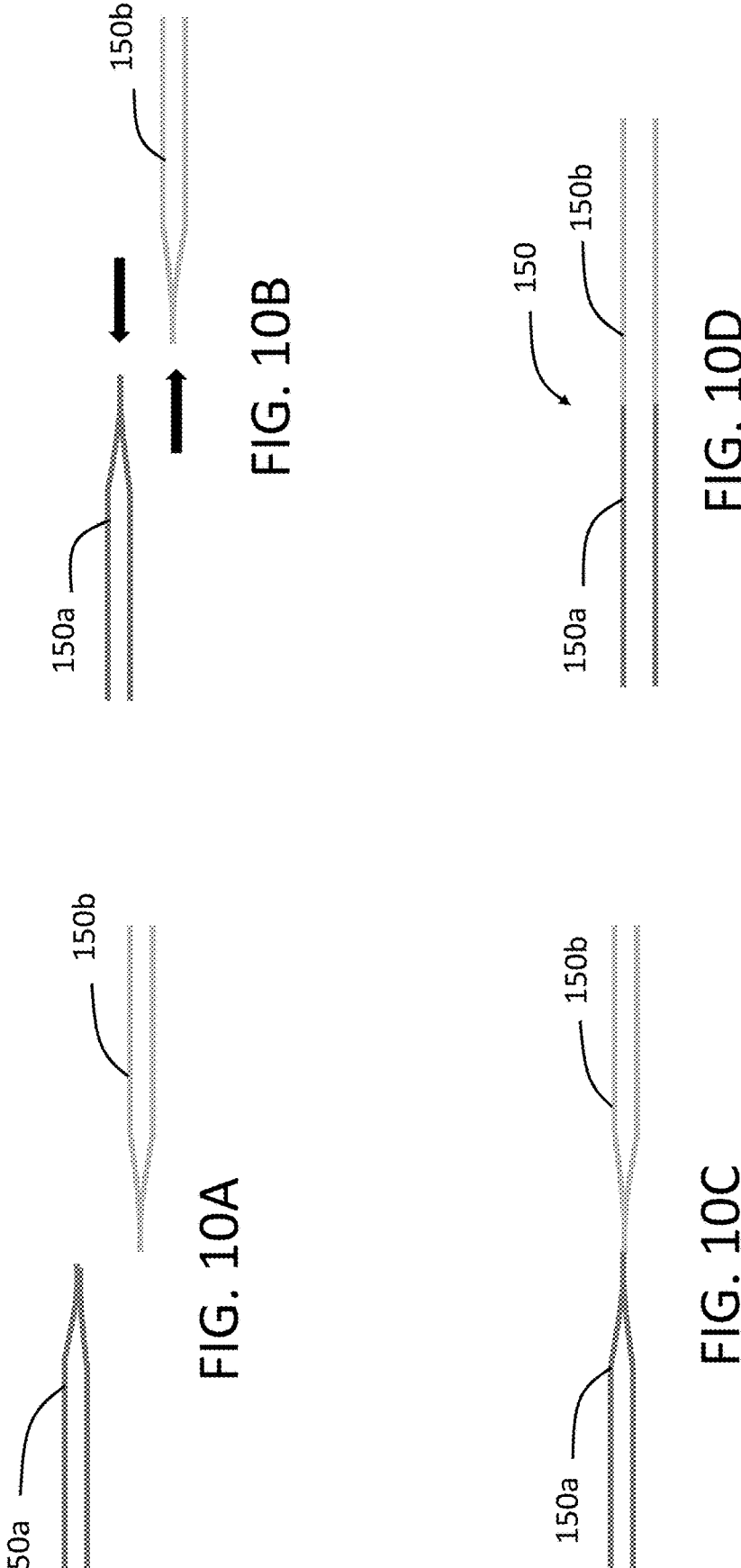

BIOPROCESSING SYSTEM

CROSS-REFERENCE TO RELATED APPLICATIONS

This application is a continuation of International Application No. PCT/GB2022/051737 filed on Jul. 6, 2022, which claims priority from Application No. GB2109779.5, filed on Jul. 6, 2021, the disclosures of which are incorporated herein by reference.

FIELD OF THE INVENTION

The present invention relates to a bioprocessing system for manipulating biologic samples, and more specifically to an automated bioprocessing system, which may be used to automate cell therapy manufacturing for example. BACKGROUND TO THE INVENTION Therapeutics are increasingly using cells rather than small molecules as the starting point. The approaches to manufacturing these products are rapidly evolving to keep up with constantly emerging new therapies. In recent years, there has been an increased use of a number of new classes of cell therapies. One class is autologous cell therapies.

Autologous cell therapies are a promising class of therapy, which have significant clinical and commercial potential ranging from treating cancer to fixing genetic defects. These therapies involve taking cells from a patient, manipulating the cells over the course of days to weeks, and re-introducing the cells back into that patient's body to produce a therapeutic effect. The steps taken during autologous cell therapies are often complex; for example, a typical CAR-T process may involve a sequence of steps starting with a cryopreserved leukopak, thawing, washing to remove DMSO, enrichment of T cells, activation, transduction, expansion, concentration, formulation fill finish into an IV bag, and cryopreservation, with several other intermediate washing steps. To date, these processes have typically been performed with labour intensive manual processes in expensive class five cleanrooms or isolators.

Due to the complexity of bioprocessing, there is a desire to automate the process while maintaining a closed system that removes the need to perform the steps in such a high-grade cleanroom, thereby reducing the labour and cost required. A closed system is one where there is no exposure of the process to the surrounding environment such that there can be no ingress of contaminants from the environment or cross contamination from other processes that are being performed simultaneously, whilst also avoiding contamination of the environment with the product under manufacture. There are systems that have tried to provide a solution to this, but each have limitations. For example, robotic systems within isolators where the robots carry out standard liquid handling manoeuvres have been developed to carry out the end-to-end cell therapy process. However, these systems are limited to carrying out one patient therapy at a time as there is no way to minimise the risk of cross-contamination, which makes the systems expensive and space inefficient. There are also significant validation burdens in ensuring the isolator can be cleaned sterilised in between each run.

A more common approach is to use closed systems involving a complex consumable element, which connects the biological sample to all the other necessary processing stations, for example via a tube that is fluidly connected to the consumable element, and provides pumping and valving to allow the steps to be performed in a particular sequence.

However, these consumable elements are very complex to manufacture and install and are consequently relatively expensive, and often unreliable. Each consumable element needs to be individually tailored to the process being performed, making the system inflexible to modifications and expensive to adapt to new processes. As the processes become more complex, so too do these consumables. Furthermore, typically only one consumable element can be operated/manipulated at once by these systems, which makes the bioprocessing expensive and space inefficient to scale up for use with multiple patients. Often, the system is still not capable of performing all the steps required for a complete bioprocessing method, and instead multiple isolated units may be operated in sequence, which means that additional labour and expertise is required to transfer the cells (e.g. patient samples) between the isolated units. This also introduces a further risk of cross contamination, and there is no simple way to detect that contamination has not occurred.

One way of forming sterile connections between tubes is tube welding, a process that is performed manually using semi-automated instruments. Sterile tube welders allow connections to be made between two tubes with closed ends without exposing the contents of either tube to the environment, and are the only widely accepted means of reusably creating closed connections within a single system. However, existing tube welding systems are generally heavy, require precise manual manipulation to insert the tubes into the welder correctly, to remove the tubes from the welder correctly, and to unpinch the weld region to permit fluid flow following welding. Additionally, existing tube welding systems need visual inspection by an operator after each weld to confirm successful welding. Overall, the welding process can take between 4 to 7 minutes of operator time. As a result of the manual operation, large portions of the tubes are often discarded by the user during each tube welding operation. Furthermore, conventional tube welding systems are not additionally configured to cut through a tube and reseal securely the ends of the separated tubes afterward, which means that they cannot maintain closure of the contents when disconnecting tubes.

However, there are a large number of reasons that would make tube welding appear incompatible with full (operator independent) automation. For example, tube welding requires the handling of long flexible tubes, which are well known to be extremely challenging to handle by automated handling means, such as robots. For example, flexible tubing is unlikely to stay within a well-defined deterministic location when moved by a robot, making engagement, alignment and orientation of the tubes challenging. When the end of a sufficiently long flexible tube, constrained at one end, is manipulated at the other, the path defined by the tube will have a number of non-unique solutions as to what the path between the constrained end and the manipulated end will take-up, dependent on the internal stress in the tube. Such a system has many degrees of freedom. Such applications are ideal for humans but very challenging for automation and therefore typically left for human operators. Since weld strength is very dependent on precise positioning and compression of the tube, any errors in engagement of the tubing by a robot may lead to failure of the weld. It is also challenging to avoid tubes becoming twisted and/or entangled with other tubes and with other parts of the bioprocessing system. Furthermore, the tubes may apply unexpected tension to the robot or any attached consumables, reducing the chance of success of the weld, or potentially damaging the connection to the consumable.

Lastly, while the core welding steps have been automated, there are no commercially available welding systems that have automated ancillary steps requiring precise manual manipulation such as unpinching the weld. Thus, until now it has been considered impractical to develop a bioprocessing system that includes automated tube welding.

Even if the above challenges could be overcome, there is still a significant reluctance in the industry to use tube welding or other in-process aseptic transfers in place of pre-connected single use tubing sets within systems where reliability and contamination issues are crucial, such as in bioprocessing systems. In an automated cell therapy process, hundreds of aseptic fluid transfers between different containers must be performed per therapy without any of them failing—failure may cause contamination of the therapy or the external environment. Where a single-use tubing set is used, it is possible to conduct an integrity test on the pre-sterilised tubing set immediately prior to use, confirming integrity has not been breached, significantly mitigating the risk of any loss of sterility/contamination breach. In contrast, it is not possible to pre-check an in-process connection, and even if an individual transfer or weld has a 99% success rate, when performing one hundred aseptic fluid transfers in succession, the chance of all of the aseptic fluid transfers being successful is only 35%. As a result, in order to achieve an acceptable 99.9% success for one hundred welds, each individual weld must have a success rate of 99.999%. One option is to try and minimize the number of tube welding operations required by the process; indeed, according to the ISO 23565 standard on design equipment systems for cell therapy manufacturing, "the equipment should be designed and utilized in such a way that the number of in-process connections, such as tube welding, is minimized in order to reduce the risk of contaminations". It is also noted in the industry that no automated, multi-use fluid connectors currently exist that are capable of multiple connection and disconnection cycles.

Therefore, the common wisdom of the industry is to entirely avoid and circumvent the problem of unreliable tube welding, by limiting the number of in process connections through the use of extensive pre-connected single-use-consumables, and by carrying out transfers manually with close operator inspection.

Therefore, none of the conventional approaches are able to provide a flexible autonomous bioprocessing system that can reliably perform many therapies, and preferably wherein multiple therapies can be performed simultaneously. Therefore, there has been little progress in attempts to automate bioprocessing systems that utilise tube welding, due to the substantial complexity and size of existing tube welding systems, and the strict requirements for reliability when applied to a bioprocessing system.

There is a need for a bioprocessing system that can optionally handle multiple patient samples at the same time, and for improved ways of manipulating aseptic fluid connections for the closed transfer of fluids and cell material, ideally which can maintain sterility/prevent contamination of the consumables and patient samples irrespective of whether the manipulation is performed within a sterile or non-sterile atmosphere in such a system.

SUMMARY OF THE INVENTION

Described herein is a bioprocessing system, comprising: a series (e.g. a plurality) of processing stations for performing operations for bioprocessing; an automated system, comprising: means for manipulating a fluid connection between a first container and a separable second container whereby to create an aseptic connection that enables a controlled transfer of fluid or cell material between the first container and the second container, wherein the means for manipulating a fluid connection is configured to create an aseptic connection that can be disconnected after the transfer of fluid or cell material is complete to enable a further such fluid connection to be manipulated between the first container and a separable third container; and means for controlling an automated sequence of operation of the processing stations.

By providing an automated system that can create (and then disconnect) aseptic (fluid) connections between (multiple) different containers (e.g. an automated system that can connect and/or disconnect containers aseptically), it is possible to perform a sequence of bioprocessing operations without the need for a human operator. This may eliminate human error and may allow the automated system to perform a bioprocessing method very reliably. As referred to herein, a "container" may be considered to be a form of "consumable" (element) in the context of the present invention.

Advantageously, the aseptic connections ensure that transfer of material between containers may occur without exposing the contents of the containers to the surrounding environment, which could otherwise contaminate the contents. After the transfer of fluid or cell material between containers is complete, the containers may then be disconnected and then one/both containers can be fluidly connected to a different container. This means that it is not strictly necessary to provide the automated system (and the processing stations) within a sterile enclosure.

Since the bioprocessing system (i.e. the manipulating means) is capable of both connecting and disconnecting the aseptic connections, the containers may be relatively simple as compared to existing containers for bioprocessing.

Furthermore, the bioprocessing system may be very flexible, since it can be adapted to process a wide variety of bioprocessing methods (i.e. different sequences of bioprocessing operations). The bioprocessing system is also very scalable, since it is possible to add further processing stations over time. Thus, such an automated system may be used to process multiple patient samples at the same time, while maintaining (e.g. aseptic) separation between the different samples, which may be held in one or more of the containers.

The means for controlling an automated sequence of operations may be provided by a processing and control unit (e.g. a "control system") of the bioprocessing system. The means to access the control system may be local or remote to the control system. The means for controlling an automated sequence of operation of the processing stations may also control the automated system (e.g. overall).

The means for manipulating a fluid connection may be configured to create and/or maintain a closed aseptic connection when manipulating a fluid connection (e.g. or creating an aseptic connection) between containers, so as to inhibit (and preferably prevent) exposure of the contents of fluidly connected containers to their surroundings. Additionally, or alternatively, the means for manipulating a fluid connection may (further) be configured to create and/or maintain a closed aseptic disconnection when disconnecting a fluid connection between containers, so as to inhibit (and preferably prevent) exposure of the contents of a disconnected container to its surroundings. A closed aseptic disconnection may also be referred to as creating or maintaining an "aseptic seal" on (or to) the container.

As used herein, the term "closed aseptic connection" or "closed aseptic disconnection" preferably connotes an aseptic connection or aseptic disconnection where contents of the containers are not exposed to the surroundings at any stage during the connection/disconnection process. A closed aseptic connection/disconnection may therefore be considered to be a "dry" aseptic connection/disconnection, which preferably connotes an aseptic connection/disconnection that does not require the use of a sterilant during its formation to ensure that it is sterile.

Indeed, for a truly closed connection/disconnection, no sterilant should be required in order to prevent contamination. In this way, there is no need to provide and maintain a supply of sterilant (or "disinfectant") within the bioprocessing system, and the need for pumps and valves to transport the sterilant is eliminated. As such, there is no risk of spillage or leakage of the sterilant, which may interfere with electronics or other devices within the bioprocessing system. This also removes the risk that sterilant finds its way into the containers and damages or kills the cells; it is difficult to supply sterilant fully to an area of interest while simultaneously ensuring that no sterilant can enter containers, thereby damaging or killing the cells. Moreover, this removes the need to find a sterilant that works with a large variety of contaminants and fully impregnates the area of interest. Furthermore, it is advantageous to keep the connection closed rather than just sterile as contaminants such as toxic heavy metals or pyrogens could still be harmful and may be very difficult to remove using sterilant.

The means for manipulating a fluid connection may be further configured to seal a disconnected fluid connection, such that the transfer of fluid or cells to or from the first and second containers is inhibited (and preferably prevented). In other words, once a fluid connection is disconnected, each of the disconnected containers is preferably sealed by the manipulating mean, ready for a new fluid connection to be formed with another container. Thus, the means for manipulating may further be configured to create an aseptic seal on/to a container when disconnecting a fluid connection.

In this way, a container may be disconnected from the bioprocessing system while maintaining a "closed" system throughout the process of many fluid connections and disconnections (e.g. between different containers). This may allow a full bioprocessing method to be performed without any exposure of the contents of a container to the surroundings, which could potentially cause contamination of the contents of the container and/or the surroundings, during connection or disconnection. Thus, the container may be connected and disconnected as many times as necessary for a particular process. Alternatively, or additionally, a separate means for sealing (a container) may be provided. The means for sealing may comprise an electromagnetic source such as a radio frequency (RF) source.

The bioprocessing system may further comprise means for installing the one or more containers into each of the series of processing stations and moving the containers between stations.

In this way, it is possible to perform a number of additional steps within a bioprocessing method without the need for operator intervention. The means for installing may be provided by a robotic device that may comprise a robotic arm on a mobile manipulation unit, or by a conveyor. The means for installing may also provide the means for manipulating a fluid connection. Advantageously, a mobile manipulation unit allows for asynchronous processes to be run simultaneously rather than needing to follow a precise sequence of operations.

The fluid connection may be created by the manipulating means joining together the (free) ends of two (preferably flexible) tubes, which may each be fluidly connected to a respective container, to create an aseptic connection therebetween. The tubes on each container will of course have a length such that the free end is sufficiently spaced from the other end attached container to allow one or more fluid connections to be manipulated.

The bioprocessing system may further comprise means for enabling the transfer of fluid or cells between aseptically connected containers. The transfer means may be in the form of a pump such as a peristaltic pump, a syringe pump, and/or a pressure driven flow pump. Advantageously, this pump may pump fluid or cells between containers while maintaining a closed system, thereby preventing contamination of the containers and/or the surroundings.

The bioprocessing system may be located within a non-sterile atmosphere. Advantageously, this significantly reduces the factory running costs and additionally may allow operators to access parts of the bioprocessing system without risk of contaminating the process.

The bioprocessing system may further comprise means for determining if the fluid connection has been successfully connected, for example by inspecting the fluid connection, preferably wherein the fluid connection is inspected automatically. The determination may be an inspection that may be performed visually, such as with a machine vision system, may be performed mechanically, for example. The means for determining (e.g. inspecting) may be located on a robotic device or may be located elsewhere in the bioprocessing system. The determination may be performed such that if a failure is detected, a corrective action may be taken, for example to isolate the contaminated region or to perform bioburden inspections. The determination (e.g. inspection) may be performed prior to commencing fluid transfer through the fluid connection, such that if there is a failure the process can be repeated until a satisfactory connection is made before any process materials enter the connection region. Advantageously, this means that required levels of reliability can be maintained, even with a large number of in process connections.

The bioprocessing system may further comprise an image capture system or device, such as a camera, for example with a microscope lens, to inspect the aseptic connection and/or to identify each of the containers. As noted above, the aseptic connection could be a fluid connection created between (preferably flexible) tubes that are fluidly connected to each container, said tubes being joined together by the manipulating means to create the aseptic connection.

Advantageously, the bioprocessing system may thereby be able to automatically maintain traceability of containers, preventing error of cross-contamination, even when large numbers of therapies are run simultaneously. The bioprocessing system may comprise a plurality of such apparatus or devices located at various locations throughout the system. The image capture apparatus or devices may be referred to as a machine vision system.

The bioprocessing system may further comprise one or more sensors configured to detect fluid leakage from the aseptic connection. The one or more sensors may comprise at least one of: a fluid sensor and a pressure sensor. Where the fluid connection between containers is created by the means for manipulating joining together free ends of tubing (e.g. that is connected to each container), the means for manipulating a fluid connection may be further configured to apply to the joined tubes a force (e.g. a tensile force) on either side of the aseptic connection such that a mechanical property can be determined.

The automated sequence of operation(s) may be controlled according to one or more predetermined workflow(s), preferably one or more reconfigurable bioprocessing workflow(s). In this way, a particular bioprocessing method may be carried out by the bioprocessing system, and the process may be readily modified or adapted without requiring any modification to the bioprocessing system itself.

The means for controlling an automated sequence of operation may be configured to simulate the automated sequence of operation prior to the bioprocessing system performing said sequence. The means for controlling an automated sequence of operation may convey at least one outcome of the simulation to an operator. The at least one outcome may comprise: an indication when particular operations occur, an indication when manual steps may need to be performed, and/or an indication that a conflict between two concurrent operations may (or may not) occur. The simulation may use current therapy quality metrics as well historical process data to inform the simulation. The simulation may also provide an indication of the likely number of cells of a given type that will be achieved by a given time period and may also give an indication of their quality.

The bioprocessing system may further comprise a monitoring system to verify that the automated sequence of operation has occurred. The monitoring system may be provided by the means for controlling the automated sequence of operation of the processing station. Preferably, inputs to the monitoring system are provided using one or more sensors that are not used by other parts of the bioprocessing system.

Preferably, the series of processing stations includes means to perform concentrations, washing and incubation. In this way, the bioprocessing system can be used to readily adapt and perform all the steps in a typical CAR-T process, which require operations such as lymphocyte enrichment, activation, transfection, washing, expansion, and harvest to be performed. There may be multiple instances of any of the processing stations, such as to provide redundancy or reduce the impact of rate-limiting steps. For example, additional incubation stations may be provided since incubation is typically the rate limiting step, though it will be appreciated that any other processing stations may be added or removed in order to reduce the impact of rate-limiting steps.

Preferably, the series of processing stations includes a means to determine cell count, cell viability, and/or cell phenotype. This increases robustness of the system and enables operators to track a cell therapy process and determine that it is within specification; this may enable a more reliable system, as out of specification processes can be identified early. In this way, it is possible to automatically monitor the process and determine if the current patient batch that is being processed is within specification. It also enables the potential for adaptive processing where parameters including cell count are used to update the automated sequence of operation. Data from the means for determining cell count, cell viability, and/or cell phenotype may be used as inputs for the means for simulating an automated sequence of operation.

The bioprocessing system may be configured to process multiple containers at the same time, preferably wherein two or more of the containers contain patient samples. In this way, it is possible to perform multiple bioprocessing methods in parallel, which may increase the efficiency of processing multiple patient samples. Since the bioprocessing system makes connections using aseptic connections, there is no need to disinfect or restart the bioprocessing system in order to process multiple containers with different patient samples. The containers corresponding to different patient samples may use the same predetermined workflow.

A first container containing a first patient sample may be processed using a different predetermined workflow to a second container containing a second patient sample. In this way, different workflows may be used for different patients without requiring modification to the bioprocessing system or use of a separate bioprocessing system. The means for controlling an automated sequence of operations may be configured to automatically schedule a sequence of actions to be followed by the bioprocessing system.

The sequence of actions may be automatically updated based on inputs received from at least one sensor of the bioprocessing system. In this way, multiple patient samples may be processed simultaneously by the bioprocessing system while minimizing the risk of conflicts between the corresponding bioprocessing workflows. For example, the sequence of operations may be scheduled to minimize and preferably prevent any of the processing stations or parts of the automated system being required simultaneously for separate bioprocessing workflows. If it is not possible to avoid a conflict, the means for controlling an automated sequence of operations may delay one of the conflicting actions based on a pre-programmed or user-configurable list of priorities.

The means for manipulating a fluid connection may be configured to create an aseptic connection between a first tube connecting to the first container, and a second tube connecting to the second container. While tubing is very difficult to handle by an automated handling means, using tubes provides a number of advantages. Firstly, tubes are already widely used in manual bioprocessing, so it is easier to adopt and work with third party consumables and other hardware. Secondly, the overall space and form factor of the automated bioprocessing system can be smaller as each unit operation only needs to work with a small tube rather than a large single-use consumable. Thirdly, since tubing is the main disposable part and can be manufactured in large volume, the overall cost is significantly reduced, and overall reliability is increased as compared to the single-use consumables containing many parts.

The means for manipulating a fluid connection may comprise a tube welder configured to join the first tube to the second tube. Preferably, the tube welder is configured to join a free end of the first tube to a free end of the second tube, though it will be appreciated that the connection may be located anywhere along the length of the tube. As used herein, the term "tube welder" refers to any device that is configured to join (i.e. weld) the first and second tubes (preferably at their free ends), thereby providing an aseptic (fluid) connection between the tubes. Tube welding is a convenient method of creating an aseptic connection without the need for a sterilant, i.e. it is generally accepted that welding is a "closed (aseptic) connection process". The tube welder may further comprise means for cutting through a length of tubing, whereby to separate the tubing. An advantage of the aseptic connection being a "closed connection", over simply being sterilised, is that contamination may still enter a connection pathway, which could still be harmful to a connection that has simply been sterilised.

The bioprocessing system may further comprise a means to manipulate the joined tubes to release a pinched portion whereby to establish a fluidic path through the joined tubes. Typical tube welders are not capable of removing the pinched portion, and thus cannot readily by incorporated into a bioprocessing system. Therefore, by providing a means to release the pinched portion, a bioprocessing method may be performed without any operator intervention.

The bioprocessing system may further comprise a tube supply means arranged to provide supplementary tubing for use by the means for manipulating a fluid connection.

One problem with using tubes to form fluid connections between containers is that the tubes may become entangled with each other and with other parts of the bioprocessing system. Therefore, it is advantageous to keep the tubes connecting to the corresponding containers relatively short. By providing a tube supply means, such as a tube reel, it is possible to extend the tubes whenever necessary, while still minimizing the risk of entanglement.

At least one of the tubes may comprise at least one identification mark at a location along the said tube, preferably wherein the identification mark is readable by an image capture system that is further configured to determine the location of the identification mark on the tube.

Preferably, the identification mark is located at a predetermined position along said tube. Preferably, the tube comprises a plurality of identification marks that may be located at regular intervals along its length. The identification marks may indicate: a tube size, a tube material, a distance between the identification mark and the corresponding container, an ID of the substance contained within the corresponding container, and/or an orientation of the tube (such as to indicate which direction leads towards the corresponding container). Advantageously, this reduces the risk of the automated system incorrectly connecting two tubes. Additionally, this allows the means for manipulating a fluid connection to engage the first tube and the second tube at an exact position and orientation, thereby reducing wastage of the tubes.

The bioprocessing system may further comprise at least one tube clip configured to secure (or "retain") the first or second tube at a pre-determined fixed/known (or readily identifiable) location relative to the tube clip. The tube clip may be located at a fixed/known location in the bioprocessing system or may be movable to/from a fixed/known location before/after/during a bioprocessing operation. By enabling the tubing to be held in position relative to a tube clip at a fixed/known location, it is much easier for an automated (e.g. robotic system) to locate and engage with the tubing rather than with the tubing hanging in space. The tube clip may comprise an identification mark that uniquely identifies the location of the tube clip in the bioprocessing system. Advantageously, this allows the means for manipulating a fluid connection to move to an exact position in the bioprocessing system in order to engage the first or second tube. The at least one tube clip may comprise additional sensors such a sensor to detect the presence of a tube, air in the tube, and/or flow rate of fluid through the tube. The tube clip may also be an active tube clip, which can be moved from an open position to a closed position that retains the tube. Advantageously the tube clips substantially reduce the risk of the automation system incorrectly engaging with and manipulating the tubes, ultimately improving the reliability of the system. The bioprocessing system may further comprise a means for sealing the tube. The means for sealing the tube may comprise an electromagnetic source such as an RF source.

Preferably, the bioprocessing system comprises at least one robotic device configured to provide at least one of: the means for manipulating a fluid connection, the means for installing the one or more containers into each of the series of processing stations, the means for enabling transfer of fluid or cells between aseptically connected containers, the means for sealing the tube and/or the means for inspecting the fluid connection. The at least one robotic device may comprise at least one robotic arm, and may comprise at least one end effector. Advantageously, by configuring the robotic device with an end effector in this way, the robotic device can move towards the tube to be engaged, thereby engaging the tubing near the consumables to be welded and reducing the need for long flexible tube lengths. This significantly eases the challenge of automation as well as provides benefits to the overall bioprocessing system in terms of reduced dead volumes contained within the tubing Also described herein is an automated system for fluidly connecting two containers (e.g. for use with the above-described bioprocessing system), wherein at least the first container has a tube fluidly connected at a first end thereto, with a second end of the tube configured to form an aseptic connection with another such tube, the automated system comprising: a robotic device (or other automated means) configured to engage the second end of the tube that is fluidly connected to the first container, and to position the tube into one or more positions to be manipulated; and means for manipulating a portion of the tube towards the second end of the tube whereby to configure the second end of the tube for creating an aseptic connection with another such tube.

The other tube may itself be connected to a second separate container, or may be a length of tube that is not connected to a container. For example, this tube may be provided in a tube supply means, such as a tube reel. The means for manipulating a portion of the tube may be part of the robotic device or may be a separate component (such as a separate robotic device) in the automated system.

It will be appreciated that any of the features discussed herein in relation to the "automated system for fluidly connecting two containers" (discussed above and herein), may equivalently be incorporated into the "bioprocessing system" (discussed above and herein), and vice versa.

The robotic device may be configured to engage the tube and/or position the tube by moving along one or more predetermined pathways.

Advantageously, by moving along repeatable and verifiable pathways, the risk of entanglement between tubes and/or the risk of collisions with other parts of the automated system is minimized For example, the robotic device may locate a consumable or a tube (such as via a tube clip) and navigate from that position in a predetermined manner. In this way, while the starting position may be variable (such as being set by the various positions of consumables and tubes), the robotic device engages and positions the tube in a repeatable and verifiable way from that position, such as by moving along a pre-determined vector or set of vectors.The means for manipulating a portion of the tube may further comprise: means for clamping a portion of the tube towards the second end of the tube whereby to form a pinched portion in the tube such that the tube is fluidly sealed upstream of the pinched portion; and means for removing a section of the tube downstream of the pinched portion whereby to remove the second end of the tube such that a new second end of the tube is thereby formed that has not previously contacted another such tube.

The section of the tube downstream of the pinched portion may be referred to as the "end section" or "downstream section". Advantageously by fluidically sealing the tube upstream of the pinch portion, if there is a failure in creating the aseptic connection the process can be repeated until a satisfactory connection is made before any process materials enter the connection region.

The automated system may further comprise means for enabling a controlled transfer of fluid and cell material between the first container and the second container. The means for enabling a controlled transfer may be in the form of a pump such as a peristaltic pump, a syringe pump, or a pressure driven flow pump. Advantageously, this pump may pump fluid or cells between the containers while maintaining a closed system, thereby preventing contamination of the containers and/or the surroundings. The means for enabling a controlled transfer may be configured as an end effector for a robotic arm.

The means for enabling a controlled transfer of fluid and cell material may be further configured to draw fluid away from the pinched portion in the tube before the aseptic connection is made with another such tube. Advantageously, drawing fluid away from the pinched portion ensures that the pinched portion is dry, which may improve reliability of removing the end section of the tube. Furthermore, drawing fluid away from the pinched portion may help to keep the tube pinched shut during removal of the end section of the tube.

The means for clamping a portion of the tube may be a station of the bioprocessing system separate to the robotic device. The means for removing a section of the tube may be a station of the bioprocessing system separate to the robotic device. At least one of: (i) the means for clamping a portion of the tube; and (ii) the means for removing a section of the tube, may be configured as an end effector for a robotic arm. In this way, the robotic arm may move in order to engage the tube, clamp the tube to form the pinched portion, and/or remove the end section of the tube without needing to place the tube in a further device. Both the means for clamping and the means for removing may be provided by a single common end effector. Alternatively, the means for clamping and the means for removing may be provided on separate end effectors, on separate robotic arms, and/or on separate robotic devices. The end effector and/or the robotic arm may be the same as the end effector and/or the robotic arm that is configured to provide the means for enabling a controlled transfer of fluid and cells, or may be a different end effector and robotic arm.

The means for removing a section of the tube may comprise at least one of: a cutting blade and a heating device, for example a laser, an RF heater, and ultrasound heater, or an inductance heater. In one embodiment, the cutting blade may be heated by the heating device, and then the cutting blade is subsequently moved to intersect and thereby cut the tube. In other embodiments, the heating device (such as an RF heater) may directly heat the tube before the cutting blade is moved to intersect and thereby cut the tube. Alternatively, the means for removing a section of the tube is configured to remove a section of tube without directly contacting the tube.

The automated system may further comprise means for manipulating the tube such that the pinched portion formed in the tube remains fluidly sealed when the tube is removed from the means for clamping.

The automated system may further comprise means for manipulating the tube, once joined with another such tube, to release the pinched portion whereby to establish a fluidic path through the joined tubes. In this way, it is possible to transfer fluid between the containers without requiring an operator to release the pinched portion. The means for manipulating the tube to release the pinched portion may be part of any of the robotic devices and/or the end effectors described above or may be a separate component of the automated system.

The means for manipulating a portion of the tube may further comprise means for sterilising the second end of the tube. The tube may further comprise an internal valve configured such that the flow of fluid or cell material into or out of the first container through the tube can be inhibited (preferably prevented) when not connected to another such tube.

The automated system may further comprise means for joining the second end of the tube with another such tube. The means for joining the tubes may comprise means for welding the tubes together to form a tube weld. By welding tubes together to form a tube weld, it is possible to allow multiple connections and disconnections to be made while maintaining a closed system. The aseptic connections may be formed without the need for a sterilant.

The means for joining the tubes may comprise a connection piece configured to connect between the second end of the tube and the other such tube, preferably wherein the connection piece is configured to receive a sterilizing fluid, for example steam, once the tubes are fluidly connected whereby to create the aseptic connection.

The end effector may comprise at least one gripping unit configured to engage and move the tube. The tube may comprise a holding device located around the tube, whereby the gripping unit grips the holder in order to engage and move the tube. The holding device may be movable along a length of the tube, such that the tube can be translated (e.g. rotated or linearly) through the holding device when gripping unit grips the holding device. The tube may have one or more protrusions on its external surface for the gripping unit to engage.

Also disclosed herein is a method of performing bioprocessing in a system having a series of processing stations for performing operations for bioprocessing using one or more containers (e.g. such as the bioprocessing system described above), the method comprising: configuring an automated system to: manipulate a fluid connection between a first container and a separable second container whereby to create an aseptic connection that enables a controlled transfer of fluid or cell material between the first container and the second container, wherein manipulating the fluid connection creates an aseptic connection that can be disconnected after the transfer of fluid or cell material is complete to enable a further such fluid connection to be manipulated between the first container and a separable third container; and controlling an automated sequence of operation of the processing stations.

Advantageously, by configuring an automated system to create and disconnect aseptic connections between containers, it is possible to perform a sequence of bioprocessing operations without the need for a human operator. This may eliminate human error and may allow the automated system to perform a bioprocessing method very reliably. Additionally, the aseptic connections ensure that transfer of material between containers may occur without exposing the contents of the containers to the surrounding environment. This means that it is not strictly necessary to provide the automated system and the processing stations within a sterile enclosure. Since the bioprocessing system is capable of both connecting and disconnecting the aseptic connections, the containers may be relatively simple as compared to existing containers for bioprocessing. Furthermore, the bioprocessing system may be very flexible, since it can be adapted to process a wide variety of bioprocessing methods (i.e. different sequence of bioprocessing operations). The bioprocessing system is also very scalable, since it is possible to add further processing stations over time.

The method may further comprise controlling the automated sequence of operation according to a predetermined workflow, preferably a reconfigurable bioprocessing workflow. In this way, a particular bioprocessing method may be carried out by the bioprocessing system, and the method may be readily modified or adapted without requiring any modification to the bioprocessing system itself.

Also described herein is a robotic end effector for joining a first tube to another such tube (preferably via a tube weld) whereby to form a fluidic path therethrough, comprising (e.g. one of more of the following): means for engaging the tube and moving it into one or more positions to be manipulated; and/or means for clamping a portion of the tube whereby to form a pinched portion of the tube towards an end of the tube such that the tube is fluidly sealed upstream of the pinched portion; and/or means for removing a section of the tube downstream of the pinched portion whereby to remove said end of the tube such that a new end of the tube is thereby formed within the pinched portion that has not previously contacted another such tube; and/or means for joining the pinched portion at the new end of the tube with a corresponding pinched portion of another such tube; and/or means for manipulating the tube, once joined with the another such tube, to release the pinched portion whereby to establish a fluidic path between the joined tubes. In one aspect, the robotic end effector may comprise all of these recited features.

Also described herein is a robotic device for a bioprocessing system (e.g. a bioprocessing system having a series of processing stations for performing operations for bioprocessing using a plurality of separable containers), the robotic device comprising: a base unit configured for automated movement around the bioprocessing system; at least one robotic arm mounted to the base unit; and at least one end effector attached to the robotic arm, the at least one end effector configured to perform at least one of the following operations: (i) manipulate a fluid connection between two containers whereby to form an aseptic connection that enables a controlled transfer of fluid or cell material between them; (ii) manipulate a fluid connection formed between two containers to perform a controlled transfer fluid or cell material between them; (iii) disconnect a fluid connection formed between two containers after the transfer of fluid or cell material is complete and thereby aseptically seal each container so as to enable a further such fluid connection to be formed between each container and a different separable container.

The robotic device (e.g. which may also be referred to as a "mobile manipulation unit") may comprise an end effector for manipulating the fluid connection between the tubes (which could include both forming and disconnection an aseptic connection) and a separate end effector for transferring (e.g. pumping) fluid along the tubes between containers. Each end effector may be located on a separate robotic arm, or multiple end effectors may be located on the same robotic arm. Alternatively, the robotic device may comprise a single end effector for both manipulating a fluid connection between the tubes and for transferring fluid along the tubes between containers. The robotic device may further comprise an end effector for sealing tubes, such as an RF tube sealer. Such an end effector for sealing tubes may be located on a separate robotic arm or it may be located on the same robotic arm as one or more of the other end effector(s).

The robotic device may be configured for automated movement around (or within) the bioprocessing system, for example between processing stations of the bioprocessing system. Alternatively, or additionally, the robotic device may be configured for automated movement across a factory floor in which the bioprocessing system is located. The robotic device may be configured to take samples from a container of the bioprocessing system, transfer fluid from the container into a sampling container, and transport the sampling container to a quality control area (e.g. a quality control (QC) lab). The QC Lab may be part of the bioprocessing system, or may be an external QC lab. The robotic device may further comprise a storage area, that may be used to store the sampling containers in or on the robotic device during transportation to the quality control area.

As used herein, the term "bioprocessing" preferably includes cell therapy, such as autologous and allogenic cell therapies, as well as vaccines and (small batch) bioprocess, for example.

As used herein, the term "automated system" preferably connotes a system operated and/or controlled by automation, and which term preferably includes one more of the following: robotic devices, conveyers, one or more actuators configured to engage and/or move containers or indeed any combination of these features that are capable of moving and/or manipulating the containers and/or tubes within the system.

As used herein, the term "robotic device" (or "robot") preferably connotes an automated machine or device programmed to perform specific mechanical functions, and which term preferably includes robots, cobots, x-y-robots, robotic arms, and one or more actuators, possibly also comprising one or more robot end effectors, and will typically also include one or more sensors, microprocessors and power supply. A robotic device may be located at a fixed location in the bioprocessing system, or may be configured to move through several locations in the bioprocessing system. For example, the robotic device may be provided upon rails, or the robotic device may comprise wheels and/or motors that allow the robotic device to move or drive around a floor of the bioprocessing system; such a robotic device may be referred to as the "mobile manipulation unit" described herein.

As used herein, the term "aseptic connection" preferably connotes a connection where contents of the respective containers being connected are not exposed to the surrounding air or atmosphere. The term "aseptic connection" may equivalently be referred to as a "closed connection" or a "sterile connection", for example.

As used herein, the term "fluid" preferably connotes liquid and/or gas, and may further include material such as cell material contained therein.

As used herein, the term "tube" or "tubing" preferably connotes a flexible tubing, or at least a tube having a flexible portion, which may be formed from a thermoplastic, for example, or other (e.g. elastomeric) materials such as CFlex®.

It will be understood by a skilled person that any apparatus feature described herein may be provided as a method feature, and vice versa. It will also be understood that particular features, or one or more combinations of features, described and defined in any aspects described herein can be implemented and/or supplied and/or used independently.

Moreover, it will be understood that the present invention is described herein purely by way of example, and modifications of detail can be made within the scope of the invention. Furthermore, as used herein, any "means plus function" features may be expressed alternatively in terms of their corresponding structure.

BRIEF DESCRIPTION OF THE DRAWINGS

Example embodiments of the present invention will now be described, with reference to the accompanying figures, in which:

FIG. 5A shows a cross-section through an example of a flexible tube suitable for use in the automated bioprocessing system;

FIG. 5B shows another example of a portion of flexible tubing suitable for use within the automated bioprocessing system;

FIG. 5C shows a schematic example of a gripping unit and a portion of flexible tubing adapted to be held thereby;

FIG. 7A to 7C show various different consumables suitable for holding media or reagents for use in the automated bioprocessing system, suitable for use within a centrifuge in the automated bioprocessing system, and suitable for use as a cell expansion vessel in the automated bioproces sing system, respectively;

FIGS. 10A to 10D show a second embodiment of an apparatus for forming aseptic connections between tubes in the automated bioprocessing system, at various steps along the connection process;

DETAILED DESCRIPTION

Figure 1:
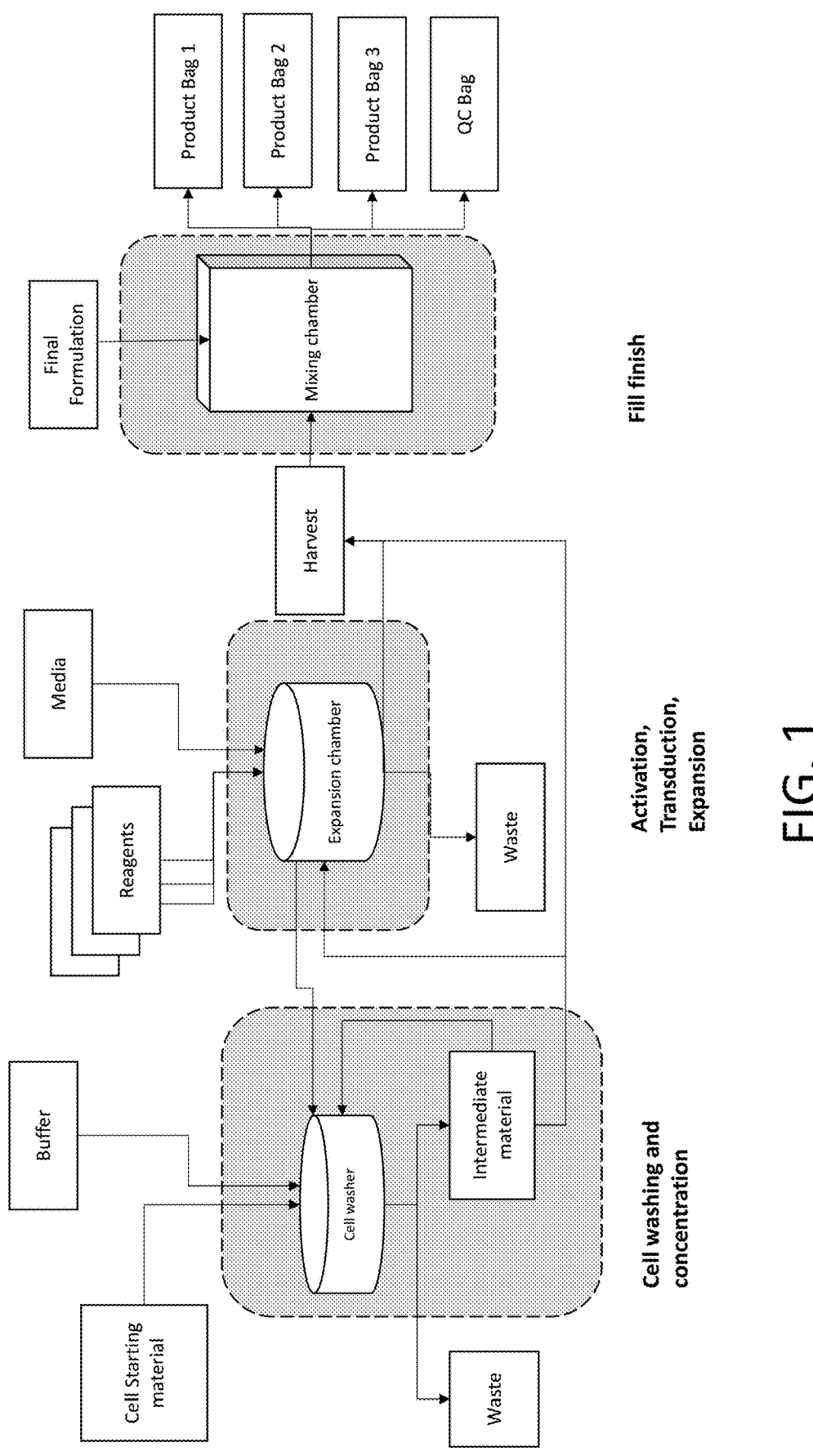
FIG. 1 shows a schematic diagram of a typical bioprocessing workflow.

An example of a typical bioprocessing workflow is shown in FIG. 1. The process contains a large number of containers and reagents, with each arrow indicating a transfer of fluid between containers. Due to the concerns already discussed previously, conventional bioprocessing systems provide all of the containers and fluid pathways within a single consumable. While this may mitigate concerns relating to cross contamination between containers, the complex consumable is very expensive and is not flexible to any modification to the bioprocessing workflow. Due to the large number of integral valves and pumps, the consumable may also be unreliable. Therefore, as will now be discussed in detail, by dividing the workflow into much smaller portions (such as by indicated with the dotted lines), it is possible to achieve the same outcomes with significantly less complex consumables. This also provides much more flexibility if the workflow is modified and allows samples to be extracted throughout the process for quality control.

Figure 2A:
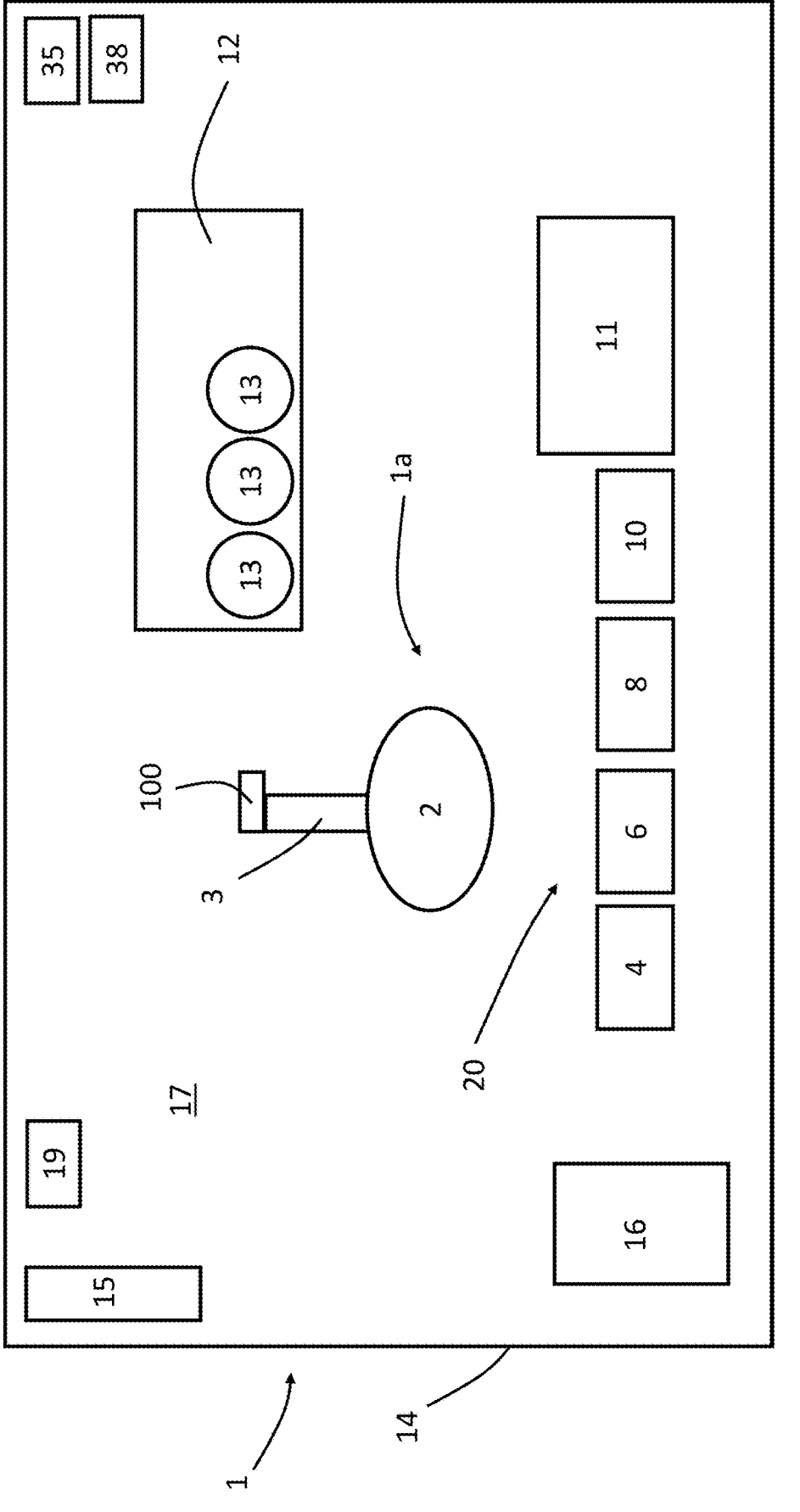
FIG. 2A shows a schematic diagram of an embodiment of an automated bioprocessing system.

An exemplary embodiment of a bioprocessing system 1 according to the present invention is shown in FIG. 2A. The bioprocessing system 1 has a series (e.g. a "plurality") of processing stations 20 configured to perform processing steps for bioprocessing, and an (automated) system 1a for automating (at least part of) the process.

In this exemplary embodiment, the bioprocessing system 1 has processing stations 20 in the form of a thawing station 4, a centrifuge 6, a magnetic cell separator 8, a controller rate freezer 10, and a refrigerator 11, though additional and alternative stations 20 (not shown) for processing can be installed depending on the specific process being performed by the bioprocessing system 1. There may also be multiple instances of any given processing station 20 at separate locations in the bioprocessing system 1.

The processing stations 20 may include any combination of a concentration station, a cryopreservation unit, a washing station, a cell enrichment station, a cell expansion station, a cell selection station, stations for determining cell count, cell viability, cell phenotype or cell type, such as a cytometer station, and/or stations for any other suitable processing or analysis step. The bioprocessing system 1 also has an incubator 12 that is large enough to contain and incubate multiple consumables 13 at a time, including under perfusion. Advantageously, a cytometer station may facilitate automatically taking samples to obtain an intermittent read of cell count and quality. This may be beneficial for keeping the process under control, opening up process improvements through adaptive control, and potentially may allow further predictive elements, as will be discussed later in more detail.

For example, the incubator 12 may be capable of storing twenty consumables 13 and operate at around 37° C., though the number of consumables 13 can be chosen to meet the needs of the particular bioprocessing to be performed. Additional incubators 12 may be provided at separate locations in the bioprocessing system 1 in order to provide additional space for further consumables 13. Each consumable 13 may contain cellular samples, reagents or fluids, and each consumable 13 connects to a first end of a tube (150 not shown) which leads to a second end of the tube 150, which is fluidly sealed when unconnected (or "free"). Thus, as referred to herein, a "consumable" may be in the form of a "container", which may for example hold cell material to be processed in a cell therapy process.

All of the consumables 13 and reagents may be preloaded in the bioprocessing system 1 before a particular bioprocessing begins, though additional reagents can be added throughout the process if required (for example at day 7 of a 10-day therapy process). The additional reagents may be required for reactivation of cells, or to add additional media to the consumables 13, for example.

A particular bioprocessing may be defined by a bioprocessing workflow, and preferably the bioprocessing system 1 can be configured to carry out several bioprocessing workflows. For example, the bioprocessing system 1 can carry out the same bioprocessing workflow in parallel for multiple patient samples, or it can carry out different bioprocessing workflows in parallel for multiple patient samples. Each bioprocessing workflow may use a different subset of the processing stations 20 in the bioprocessing system 1. In a preferred embodiment, the bioprocessing system 1 comprises stations 20 to perform concentrations, washing and incubation processes.

The bioprocessing system 1 comprises an automated system 1a configured to install one or more consumables 13 into each of the series of processing stations 20 and to move the consumables 13 between stations 20. In this embodiment, the automated system 1a includes at least one robotic device 2 that can move the consumables 13 between the various stations 20, and can manipulate the tubes 150 connecting to each of the consumables 13. Alternatively, or additionally, the robotic device 2 may be configured to move the processing stations 20 in order to connect the consumables 13 to the processing stations 20. The bioprocessing system 1 may further comprise an observation system 35 (e.g. a machine vision system) for observing operations of the automated system 1a. The bioprocessing system 1 may further comprise a processing and control unit 38 for controlling a sequence of operations of the automated system 1a; in other words, the processing and control unit 38 may provide a means for controlling an automated sequence of operation of the processing stations 20 and/or the automated system 1a including the robotic device 2. While the processing and control unit 38 is described herein as an individual unit of the bioprocessing system 1, it will be appreciated that multiple units may be present, for example separate units for processing and for control.

Figures 2B, 2C:
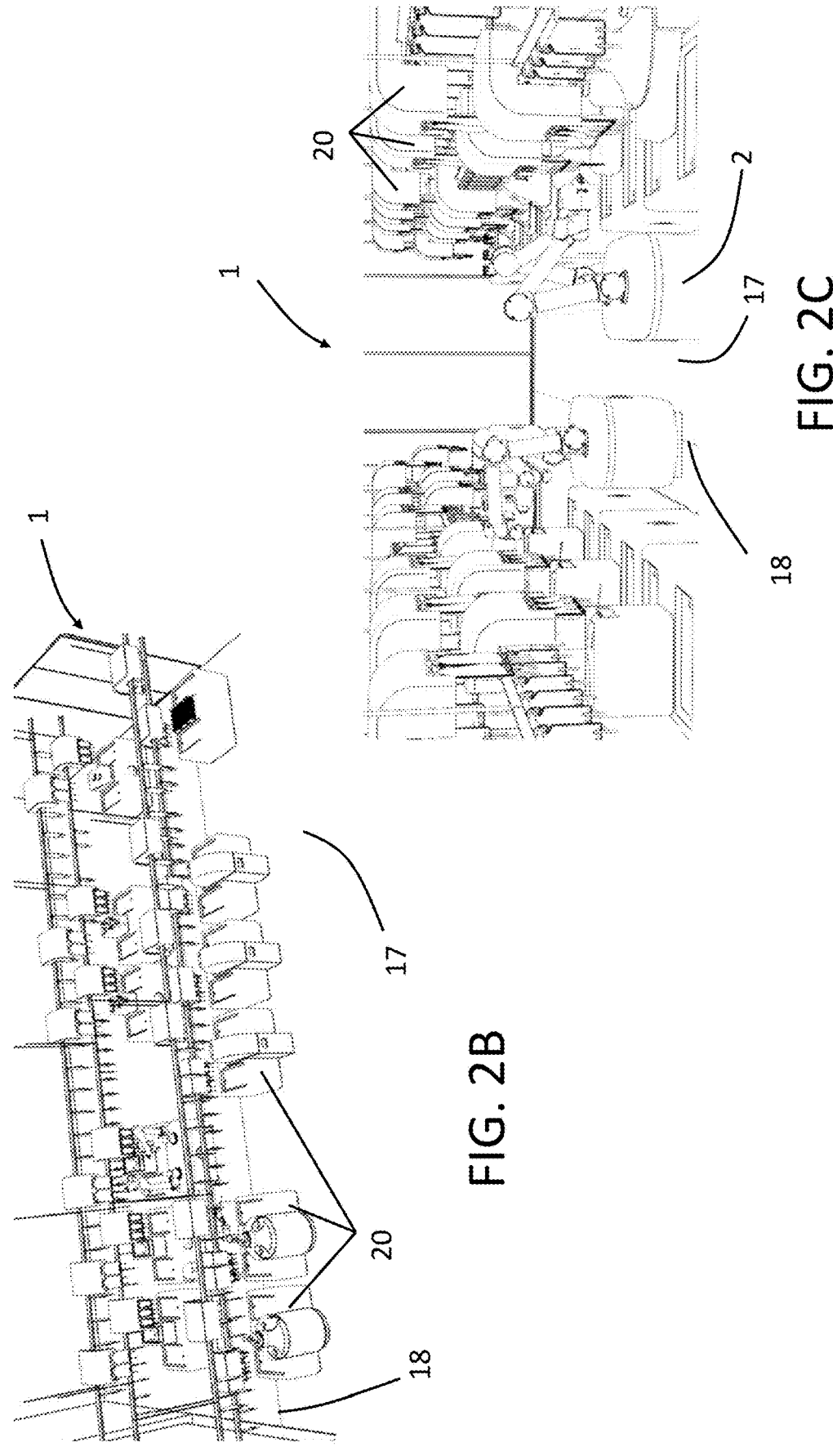
FIGS. 2B and 2C show a particular example of a bioprocessing system configured as an automated factory.

A particular example of a bioprocessing system 1 is shown in FIGS. 2B and 2C, where all the processing stations 20 described above are located at static positions on a factory floor 17. In this configuration, the bioprocessing system 1 may be referred to as an automated factory. Each robotic device 2 is also provided on the factory floor 17, which may be implemented in a number of ways. For example, each robotic device 2 may be located at a fixed location in the bioprocessing system 1, or may be mounted on rails 18, which allows the robotic device 2 to have access to all areas of the bioprocessing system 1 such as the stations 20. The robotic device 2 may be configured as a co-operative robot ("cobot"). The robotic device 2 may have at least one robotic arm 3 for manipulating the consumables 13 and tubes 150, as shown here, or may include a conveyer belt, one or more actuators, or any combination of the above aspects. Preferably, the bioprocessing system 1 comprises a plurality of robotic devices 2, with different processes in the bioprocessing system 1 being performed by different robotic devices 2. For example, there be separate robotic devices for manipulating the tubes 150, forming fluid connections between separate consumables 13 (e.g. by tube welding and sealing), pumping fluid along tubes 150, conveying consumables 13, and/or sampling from consumables 13 for quality control. It will be appreciated that other operations may be performed by the robotic devices 2, and that any of the robotic devices 2 may be configured to perform more than one operation. Preferably, multiple robotic devices 2 may be configured to perform each operation in order to provide some redundancy, and to allow any robotic device 2 to be repaired and/or replaced without interrupting progress of a particular bioprocessing workflow.

Figure 3B:
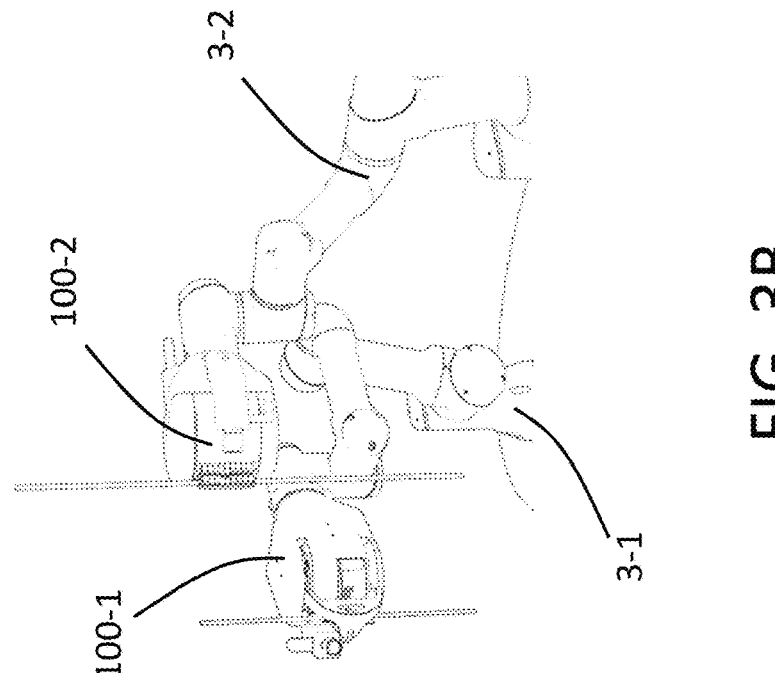
FIGS. 3B to 3D show various configurations of robotic arms and end effectors for the robotic arms.
Figure 3A:
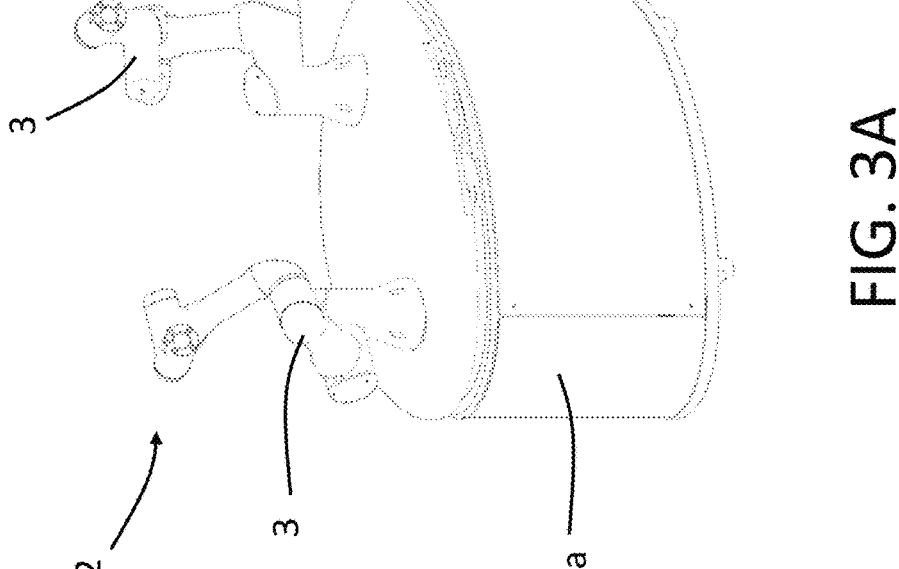
FIG. 3A shows an example of a mobile robotic device having two robotic arms, which may be part of the bioprocessing system shown in FIG. 2.

Each robotic device 2 may be implemented as a mobile manipulation unit 2, such as the one depicted in FIG. 3A. The mobile manipulation unit 2 can be configured to move autonomously across the floor 17 of the bioprocessing system 1 in order to access areas such as the stations 20. Each mobile manipulation unit 2 may comprise a base unit 2a configured for automated movement within or around the bioprocessing system 1. For example the mobile manipulation unit 2 may comprise a wheel-mounted base unit 2a, which may house a motor and other control and communication componentry (not shown) that are together configured to enable the mobile manipulation unit 2 to move within or around the floor 17 of the bioprocessing system 1. For example, the mobile manipulation unit 2 may comprise a communication unit (not shown) that may receive instructions from the processing and control unit 38 and/or may transmit data (such as from sensors or cameras) to the processing and control unit 38, which act to control the motor to drive the wheels whereby to motivate the mobile manipulation unit 2. The use of mobile manipulation units 2, particularly to move consumables around the factory floor 17, is advantageous as they enable asynchronous processes to be carried out simultaneously, unlike a conveyor which requires a precise sequence of operations.

Each mobile manipulation unit 2 may have at least one robotic arm 3 mounted to the base unit 2a and configured to perform one or more operations in the bioprocessing system 1. Preferably, the mobile manipulation unit 2 may have multiple robotic arms 3 (e.g. two robotic arms 3, as shown in the example of FIG. 3A) mounted to a base unit 2a, which are each configured to perform a different operation, such that multiple operations can be performed by the mobile manipulation unit 2 when positioned at a processing station 20, for example, either sequentially or simultaneously. For example, one robotic arm 3 may be configured to manipulate the fluid connections between consumables, and another robotic arm 3 may be configured to pump fluid along tubes 150. There may also be a robotic arm 3 for sealing tubes 150. Each robotic arm 3 may operate at least one end effector 100 configured to perform at least one operation in the bioprocessing system 1.

Figure 3D:
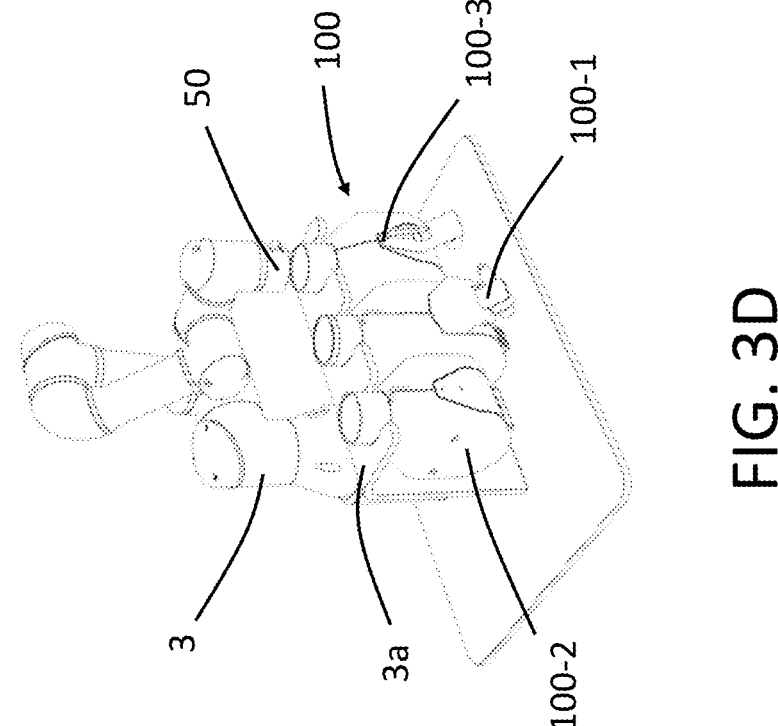

Various exemplary configurations of robotic arms 3 will now be described in relation to FIGS. 3B to 3D. These configurations may be incorporated into a mobile robotic device 2 (such as a mobile manipulation unit 2, described above), or may be incorporated into a static robotic device 2 positioned at a fixed location within the bioprocessing system 1. In the embodiment shown in FIG. 3B, the robotic device 2 comprises a first robotic arm 3-1 having a first end effector 100-1 and a second robotic arm 3-2 having a second end effector 100-2. This arrangement provides flexibility to the mobile manipulation unit 2; both robotic arms 3-1, 3-2 may be operated independently. In this example, the first end effector 100-1 is configured as a sterile tube welder in a manner that will be described later in more detail, and the second end effector 100-2 is configured as a pumping unit 30 for pumping fluid through the tubes 150. An embodiment of the pumping unit 30 will be described further in relation to FIG. 4B. However, when the robotic device 2 is a static robotic device 2, it may be challenging for both arms 3-1, 3-2 to reach all the areas necessary.

Figure 3C:
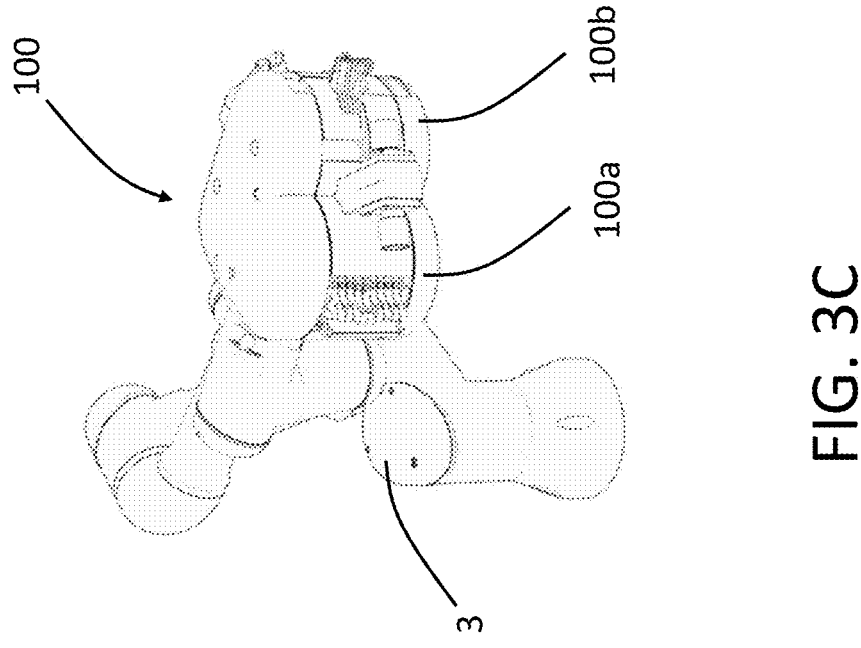
Figure 4B:
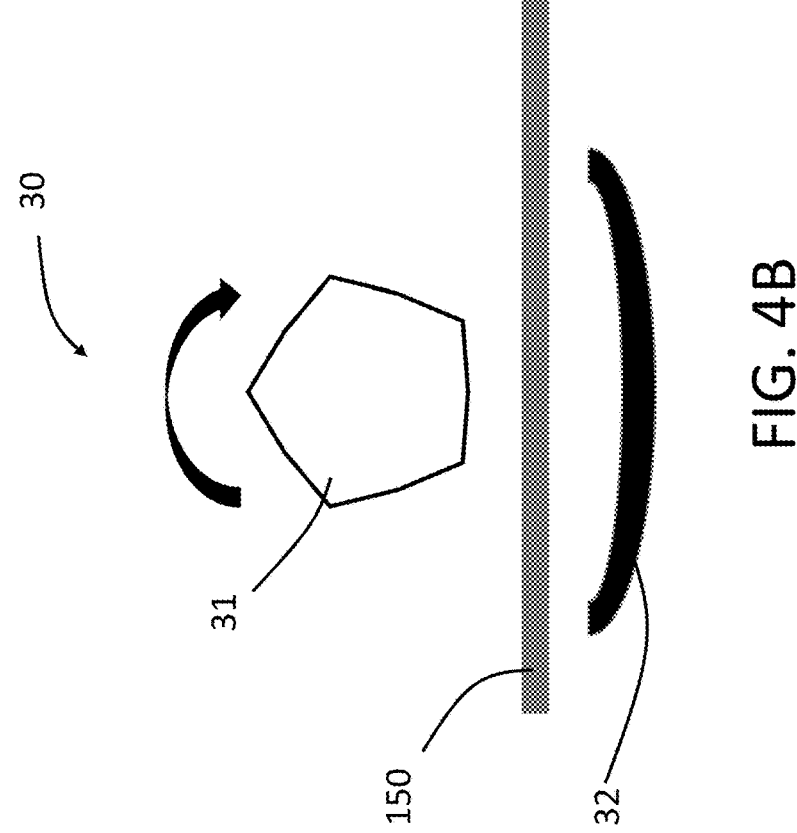
FIG. 4B shows an example of a peristaltic pumping arrangement for pumping fluid along a tube.

In an alternative embodiment, as shown in FIG. 3C, a single robotic arm 3 comprises an end effector 100 with a first portion 100a configured as a sterile tube welder and a second portion 100b configured as a pumping unit 30. In this way, the single robotic arm 3 may simply change position (e.g. rotate) so that each portion 100a, 100b may be operated for its specified purpose. This may improve the reach of the robotic arm 3 and is more space efficient, but may result in the end effector 100 being more heavy.

As a further alternative, the end effector 100 may be interchangeable with the robotic arm(s) 3. As depicted in FIG. 3D, a robotic arm 3 may have a gripping unit 50 configured to engage with a selection of end effectors 100 such as those already described above. The gripping unit 50 may have a pair of jaws to grip the selection of end effectors 100 or may use magnetic coupling to select one of the end effectors 100. The selection of end effectors 100 may include an end effector 100-1 configured as a tube welder, an end effector 100-2 configured as a pumping unit 30, an end effector 100-3 configured as a sealing unit, or may include any combination of end effectors. The selection of end effectors 100 may be located anywhere in the bioprocessing system 1 that is accessible by the robotic device 2. Preferably, the selection of end effectors 100 are always located within reach of the robotic arm 3 such as in a tool holder 3a or "tool belt" 3a next to the robotic arm 3. Advantageously, this allows a single robotic arm 3 to operate a wide range of specialised end effectors 100.

For example, a mobile manipulation unit 2 may have end effectors 100 for both tube welding and pumping. Therefore, the mobile manipulation unit 2 may be able to join two consumables 13 together and transfer fluid between the consumables 13. Alternatively or additionally, the mobile manipulation unit 2 may have an end effector 100 for tube sealing. Alternatively or additionally, the mobile manipulation unit 2 may take sterile samples (for example from bioreactors) by welding and pumping fluid into a sampling consumable 13. Subsequently, the mobile manipulation unit 2 may transport the sampling consumable to a quality control (QC) lab. The mobile manipulation unit 2 may comprise a storage area (not shown) where the sampling consumable 13 may be stored during transportation to the QC lab. Preferably the storage area is temperature controlled.

The automated system 1a is configured to manipulate a fluid connection between a first consumable 13 and a separable second consumable whereby to create an aseptic connection that enables a controlled transfer of fluid or cell material between the first consumable 13 and the second consumable 13. Here, the robotic device 2 is used to form (or manipulate) fluid connections between the tubes 150 so that separate consumables 13 can be connected together.

The connection between tubes 150 may be performed by an end effector 100 located on the robotic arm 3, as already described above. Alternatively, the robotic arm 3 may move and place the tubes within a separate connection unit (not shown) at one of the stations 20 where the tubes 150 are subsequently connected. In either case, the connections between tubes 150 are made aseptically such that the contents of the consumables 13 and tubes 150 are never open or exposed to the surrounding air or atmosphere at any stage, i.e. the connections remain "closed", where no additional sterilant is required in order to prevent contamination. Several ways to form or maintain "closed" aseptic connections between the consumables 13 will be discussed later in more detail. However, preferably sterile tube welding is used to manipulate fluid connections between tubes 150.

The fluid connections are also reversible, such that the tubes 150 can be disconnected and reconnected to different consumables 13 as many times as necessary in order to perform the required bioprocessing method. In other words, the automated system 1a is configured to create an aseptic connection that can be disconnected after the transfer of fluid or cell material is complete to enable a further such fluid connection to be manipulated between the first consumable and a separable third consumable.

As mentioned above, during both the connection and disconnection, the consumables 13 and tubes 150 never have their contents exposed to the surrounding air or atmosphere such that a controlled transfer of fluid and/or cell material occurs only between the consumables 13 that are connected together.

Figure 4A:
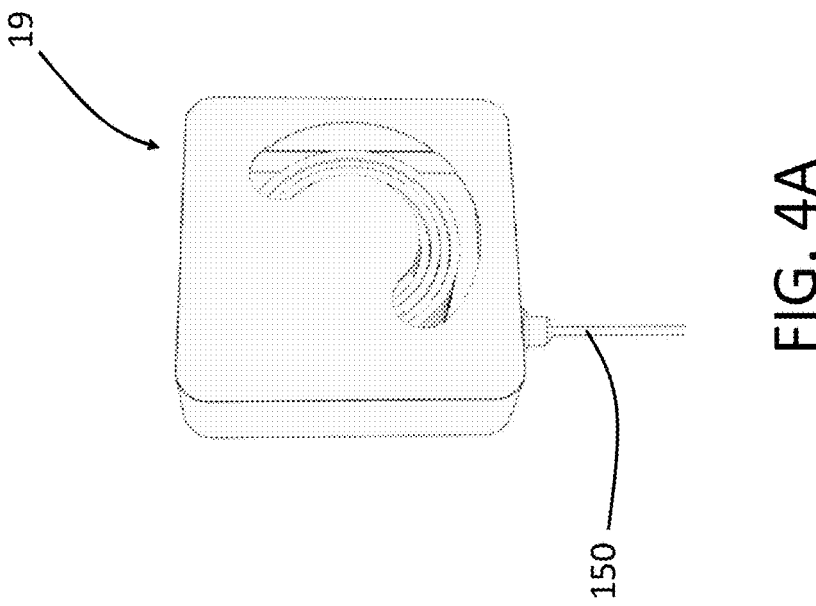
FIG. 4A shows a tube reel that my provide supplementary flexible tubing for connecting containers in the bioprocessing system.

In order to avoid entanglement between different tubes 150 and other parts of the bioprocessing system 1, it is desirable for the lengths of the tubes 150 connecting to each consumable 13 to be kept relatively short. However, it is also important to have a sufficient supply of tubing in order to make many connections and disconnections between several separate consumables throughout a particular cell therapy method. Therefore, a tube supply means 19 such as a tube reel 19 may be provided in the bioprocessing system 1. An example of a tube reel 19 is shown in FIG. 4A. The tube supply means 19 may be provided at a fixed location in the bioprocessing system 1, or may be incorporated into at least one of the robotic devices 2 such as directly on the end effector 100. If the tube 150 connecting to a particular consumable 13 is not long enough to make the required connection in a particular bioprocessing step, the automated system 1*a* may extract a supplementary length of tubing from the tube supply means 19 and use it to extend the tube 150 connecting to the consumable 13. As will be discussed in detail later, the extension of the tube 150 is preferably performed by tube welding, in a manner that ensures that the contents of the tube 150 are not exposed to the environment, or to any of the remaining length of tubing in the tube supply means 19.

Since the contents of the tubes 150 are never exposed to the surroundings, it is not strictly required to have a sterile atmosphere around stations 20, consumables 13, or robotic devices 2. An enclosure 14 may be provided to prevent access by operators and/or to provide a sterile atmosphere or otherwise control the environment for example by controlling the temperature, light levels or other conditions. However, preferably the bioprocessing system 1 does not require a sterile enclosure 14, and the processing stations 20 are instead provided on a factory floor 17 in a space that may be traversed and accessed by both human operators and the one or more robotic devices 2.

The bioprocessing system 1 also has a pumping unit 30 that pumps fluid along the tubes 150 once the robotic device 2 has successfully connected two consumables 13 via their respective tubes 150. As already discussed above, the pumping unit 30 may be located on the robotic arm 3. Alternatively, the pumping unit 30 may be a static component placed at one of the stations 20 into which the tubes 150 are placed by the robotic arm 3 for pumping to occur. The pumping unit 30 may be a peristaltic pumping arrangement 30 such as the one shown in FIG. 4B although a pressure driven flow pump or syringe pump could alternatively or additionally be used. Optionally, different types of pumps may be used for different pumping operations. This pumping arrangement 30 has a rotating wheel 31 driven by a motor on a shaft (not shown). The pumping arrangement 30 also has a clamp 32, and prior to a pumping operation, the tube 150 is positioned by the robotic device 2 between the rotating wheel 31 and the clamp 32. The pumping arrangement 30 subsequently compresses the tube 150 between the rotating wheel 31 and the clamp 32, and when the rotating wheel 31 rotates, it pumps fluid along the tube 150. Furthermore, the pumping arrangement 30 can be used to prevent any flow of fluid through the tube 150 by compressing the tube 150 between the rotating wheel 31 and the clamp 32 without rotating the wheel 31. While a pumping unit 30 is preferred, transfer of fluids and cell material could for example be effected by way of gravity, or by addition of gas via a sterilising filter.

The robotic arm 3 may have at least one gripping unit (50 not shown) to allow the consumables 13 and the tubes 150 to be held and moved by the robotic device 2. The tubes 150 are sufficiently flexible that they can be manipulated into a position to be welded. The tubes 150 preferably have a standardised material, shape and diameter so that connections between tubes 150 can be consistently performed by the robotic device 2. For example, the bioprocessing system 1 may use only one standardised type of tube throughout the system, or a small number of standardised tubes may be used. The type of tube may be selected to optimize weld quality. By using a small number of pre-specified tubes that have been verified to weld very well, reliability can be enhanced.

FIG. 5A shows a cross-section through a tube 150 that has a non-circular profile, which may allow the tube 150 to be easily manufactured by attaching two flat strips of material together. Furthermore, the tube 150 can more easily be flattened by the gripping units 50 or by the pumping unit 30 in order to pump fluid through the tube 150 or to pinch the tube 150 shut to prevent any movement of fluid. The tubes 150 are preferably formed from a thermoplastic, but could be formed with other materials such as a CFLex® (elastomeric) material.

Each tube 150 may have a section that is enclosed by a rigid external casework that can be more easily manipulated by the robotic arm 3. Alternatively, the tube 150 may have a series of protrusions spaced along its external length that are more easily manipulated. For example, FIG. 5B shows a tube 150 with a series of protrusions 40 (e.g. "handling sections") in the form of radially (outwardly) extending flange regions 40 that have been pre-moulded at various positions along its length.

By providing handling sections 40 it may be easier to apply tension to a tube 150. For example, FIG. 5C depicts a gripping unit 50 that has two grippers 55 which can be used to grip onto the handling sections 40. In this way the grippers 55 can apply tension to the tube 150 to straighten it to be placed into the pumping unit 30 or into another piece of apparatus such a pinch valve (not shown) for preventing flow of fluid.

The bioprocessing system 1 may also comprise image capture systems or devices such as sensors and/or cameras to be used during operation of the bioprocessing system 1 or for inspection and quality control. These image capture systems or devices, together with one or more processing units, may be referred to as an observation system or a machine vision system 35, though processing may be performed by the processing and control unit 38. For example, cameras may be distributed throughout the bioprocessing system 1, such as at fixed locations on the factory floor 17. Alternatively or additionally, cameras and sensors may be located on the one or more robotic devices 2, such as on the robotic arm 3 or the end effector 100 of at least one of the robotic devices 2.

Figure 6B:
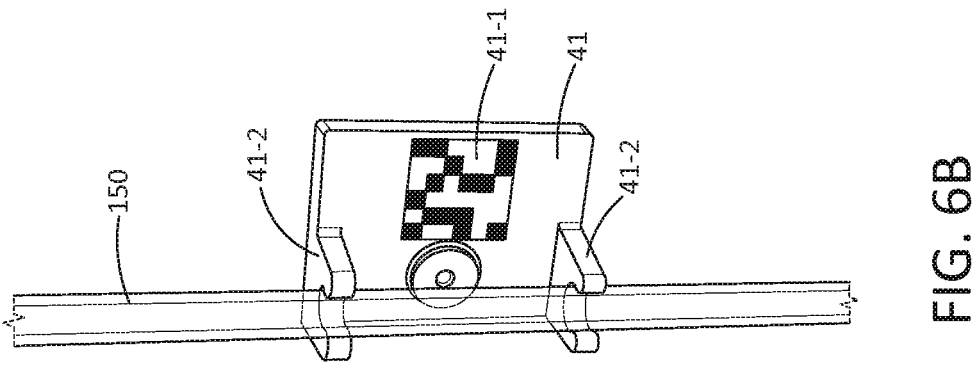
FIG. 6B shows a tube clip securing a tube, where the tube clip includes an identification mark to facilitate location of the tube by a robotic device.
Figure 6A:
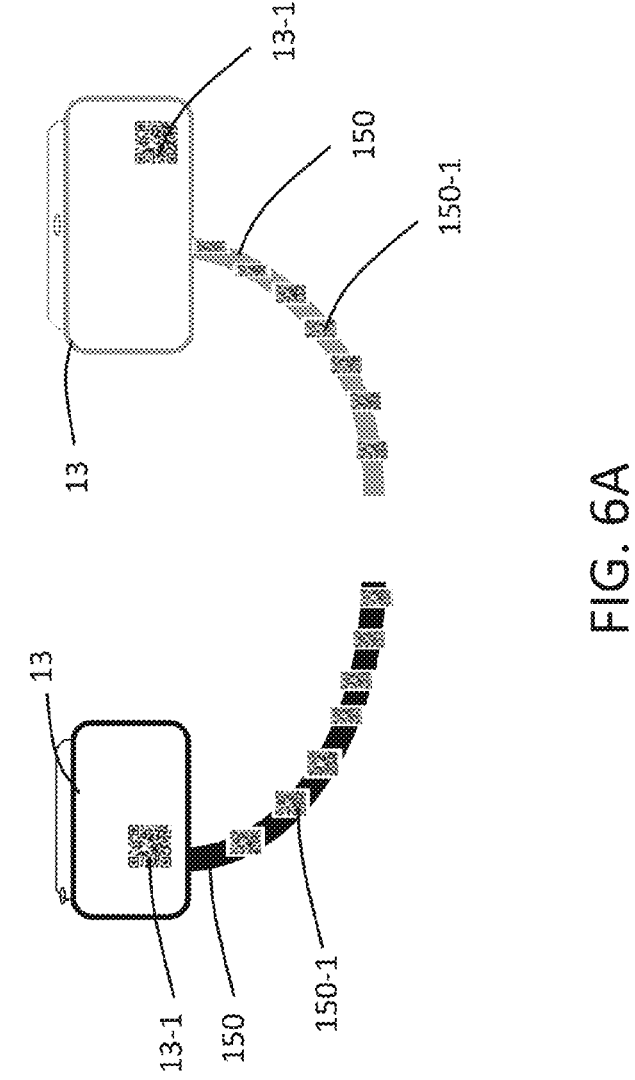
FIG. 6A shows examples of consumables and tubes that have identification marks to facilitate tracking by an observation system.

As shown in FIG. 6A, each consumable 13 may be identified by the camera using an identification mark 13-1 such as by using a unique bar code or QR code on each consumable 13. This allows every consumable 13 and sample to be tracked uniquely and automatically through a cell therapy process, maintaining traceability, facilitating integration with Electronic Batch Records (EBRs) and enabling the processing of multiple batches simultaneously. Other identification methods may be used, such as by using unique radio-frequency identification (RFID) tags. Especially when the bioprocessing system 1 processes several patient samples, it is important to be able to trace the samples accurately and automatically throughout the bioprocessing system 1, in order to reduce risk of mixing up different batches.

Similarly, the tubes 150 may also be identified using identification marks 150-1. For example, the identification mark 150-1 may be a unique bar code or QR code, though other identification methods may be used, such as by using RFID tags. The identification marks 150-1 may be located at regular intervals along the length of the tube 150, with each identification mark 150-1 uniquely providing data about the tube 150, such as its location, orientation, materials, size and/or other properties. For example, the identification mark 150-1 may indicate: a unique reagent ID, a tube size and material (which may affect welding and pumping parameters), a distance between the identification mark 150-1 and the corresponding container 13, and/or the orientation of the tube (such as to indicate which direction leads towards the container 13). The identification marks 150-1 may be printed onto the tube 150 or laser etched into the tube 150 in a similar way to how manufacturer data is marked. Providing identification marks 150-1 along the tube 150 may provide a number of advantages. Firstly, it may be possible to identify reliably which container 13 a particular tube 150 is connected to, simply by examining the identification marks 150-1 on a tube. This ensures that prior to an aseptic connection being made between two containers 13, the tubes 150 may first be brought together, checked by one of the cameras in the bioprocessing system 1, before the connection process even begins, thereby reducing the risk that any containers 13 are connected incorrectly. Furthermore, it may also be possible to determine where along the length of the tube 150 a connection is to be made, so the wastage of the tube may be minimized and the number of cuts can potentially be calculated based on the total remaining length of tube 150. Finally, the identification mark 150-1 may also be used to indicate to the processing and control unit 38 what settings should be used for welding and pumping.

FIG. 6B shows a tube clip 41 into which a tube 150 has been clipped. A number of such tube clips 41 may be distributed throughout the bioprocessing system 1. The tube clip 41 may comprise an identification mark 41-1 that uniquely identifies the location of the tube clip 41 in the bioprocessing system 1. For example, the identification mark 41-1 may be a unique bar code or QR code, though other identification methods may be used, such as by using unique RFID tags. The tube clip 41 comprises a tube retaining element such as at least one pair of clipping jaws 41-2 that retain a tube 150 in place when the tube is inserted between the clipping jaws 41-2. The clipping jaws 41-2 are arranged at a fixed location relative to the identification mark 41-1 so that a tube 150 retained in the clipping jaws 41-2 may reliably be located with reference only to the identification mark 41-1. Advantageously, this simplifies the challenge of autonomously locating and handling flexible tubes 150 and instead allows a gripping unit 50 of a robotic arm 3 or end effector 100 to move to an exactly defined set of coordinates (e.g. XYZ coordinates) in order to locate the tube 150 between the clipping jaws 41-2. The tube clip 41 may further comprise a sensor such as a bubble sensor, which are able to detect the presence of the tube, air in the tube, and/or flow rate of fluid through the tube 150. Furthermore, the tube clip may also contain an actuator to move the clip from an open and closed position, where the movement between the open and closed position is designed to seat the tube in a defined reference point and to prevent the tubing from being pulled out of the clip. The tube clips 41 may be located at fixed locations (e.g. predetermined, known or readily identifiable locations) in the bioprocessing system 1. The tube clips 41 may be movable before/after/ during a bioprocessing operation. For example, the tube clips 41 may be initially installed into the bioprocessing system 1 by a user during a setup phase and may be installed on rails or racks; the user may subsequently clip one or more tubes 150 into corresponding tube clips 41. The machine vision system 35 may scan the tube clips 41 to identify the initial locations of all of the tubes 150, such that a robotic device 2 may correctly engage the tubes 150 during a bioprocessing operation. This provides a setup that is both flexible and robust.

For quality control, the cameras and sensors of the machine vision system 35 may inspect the connections between tubes 150 to verify that a successful connection has been created. The camera may have a microscope lens to allow for a detailed inspection of the connections between tubes 150. During inspection by the cameras and sensors, the connection may be tested in a number of ways. Ultrasound waves may also be used to confirm whether there are cavities in the connection, and/or the gripping unit 50 may be used to apply pressure to the tubes 150 at or near the connection. The gripping unit 50 may be used to apply tension to the connection between the tubes 150 and measure a stress-strain profile of the joined tubes 150. A fluid sensor or atmospheric sniff sensor (e.g. "sniff leak" or "gas-leak" detectors) may be used to detect fluid leakage from the connection. If the measured stress-strain profile, visual inspection by the camera, or parameters measured by the sensors indicate that the connection between tubes 150 is defective, then the tubes 150 may be disconnected and a new fluid connection manipulated until a successful aseptic connection is formed. The quality control may be performed automatically each time a connection is made without input from an operator. The connections between tubes 150 may be isolated from the respective consumables 13 until the quality control has been performed. This may be achieved by pinching the tubes 150 and/or by allowing outflow of fluid only. In this way, even if a defective connection is found, the contents of the consumables 13 still remain isolated from the surrounding air or atmosphere. In the event of a defective connection, the process can be repeated until a satisfactory connection is made before any process materials enter the connection region.

The bioprocessing system 1 may further comprise a processing and control unit 38 that may be configured to run one or more software programs and/or to control various components of the bioprocessing system 1 such as the automated system 1a, the processing stations 20, and/or the machine vision system 35. While the processing and control unit 38 is described herein as a single unit, it will be appreciated that multiple units may be provided to perform the same function, such as separate units for process and for control. The bioprocessing system 1 may have a user interface 15 for a user to input instructions to be executed by the processing and control unit 38. The user interface 15 may also be located remotely to allow for remote monitoring and/or control of the bioprocessing system 1, for example with data stored in the "cloud". The bioprocessing system 1 may have a loading hatch 16, where new consumables 13 can be loaded into the bioprocessing system 1, or equivalently where used consumables 13 can be removed from the bioprocessing system 1 after use. The operator can also use the user interface 15 to program the bioprocessing system 1 to perform a particular automated sequence of operations in a particular bioprocessing workflow, thereby providing a means for controlling an automated sequence of operation of the processing stations of the bioprocessing system 1. An operator can also use the user interface 15 to take regular samples from the process automatically, which can be processes on a cell count processing station or cytometer or removed from the bioprocessing system 1 via the loading hatch 16 without exposing any of the contents of the consumables 13 to the environment. The samples may be run on other third party equipment (which may be referred to as a QC lab), such as to test for cell count, viability or any other parameter to monitor progress of the cell therapy process. By analysing the samples throughout a cell therapy process, the operator can ensure that the process is maintained with specification, and furthermore the resulting data may allow for adaptive control such as adjustment of gas, media and other parameters for each consumable 13 in the process.

An additional problem associated with automated manipulation of tubes 150 is that the free ends of the tubes 150 may be difficult for the automated system 1*a* to identify and may be in an indeterminate position. Particularly when manipulating long lengths of tubing, there is a risk that they become entangled with each other or collide with other parts of the bioprocessing system 1 when the tubes 150 are moved around the bioprocessing system 1. Therefore, the processing and control unit 38 may operate that automated system 1*a* so that tube 150 movements generally follow a well-defined path between set locations. This ensures that the behaviour can be well characterised and validated. In other words, the sequence of operations of the bioprocessing workflow may comprise a list of defined unit operations and connection steps; these steps are repeatable and reversible by the automated system 1*a*, where the tubes 150 are moved from one known position to another known position along a predetermined path. Furthermore, if there is a need to locate the free end of a tube 150, the automated system 1*a* may first locate the corresponding consumable 13, and then follow the tube 150 (either visually or mechanically) until the free end of the tube 150 is located. Where this is performed mechanically, such as by one of the robotic devices 2, the robotic device 2 may straighten the tube 150 as it does so, such that the robotic device 2 still follows a pre-determined path. Similarly, when performing a welding operation, it may be desirable to move the tube 150 and connect the tubes in free space, such as at a location between the two corresponding containers. To enable this, the robotic devices 2, may pull the tubes 150 through the tube clips 41 (such as when the tube clips 41 are in the closed position, as outlined above) such that robotic device 2 still follows a pre-determined path, the robotic device 2 can interact with the tubes 150 where they are well located, and furthermore so that in stress or strain on the tube is taken up by the tube clips 41. In other words, the tube clips 41 may act as pulleys or brackets through which the tubes 150 may be pulled or translated.

The processing and control unit 38 may run an auto-scheduling program that automatically schedules a sequence of operations to be performed by the bioprocessing system 1. One challenge associated with running multiple cell therapy operations in parallel is that each of the operations may start at different times, take different times to run (due to biological variability), and potentially have different programmed workflows. Additionally, the bioprocessing system 1 may have a limited number of resources such as processing stations 20, robotic devices 2, and/or robotic arms 3. As a result, there may be a number of conflicts that arise in scheduling multiple cell therapy operations, and there may be a substantial risk of mechanical collisions between parts of the bioprocessing system 1.

In order to address this, the auto-scheduling program translates the various user-programmed workflows and determines a sequence of actions to be followed by the bioprocessing system 1. The auto-scheduling program may update this sequence of actions based on inputs such as current processing times. Where the auto-scheduling program determines that two conflicting actions must be performed simultaneously, the program may delay one of the tasks within specified limits to avoid the conflict. If this is not possible, the program may instead delay the less critical task, or may flag an error or raise an alarm for human intervention. The importance of tasks may be decided based on a pre-programmed or user-configurable list of priorities.

In addition, the processing and control unit 38 may run a simulation program that can simulate the workflows and corresponding sequence of actions both prior to and during the runs, determine when future events will occur, and determine the likely quality of the output product based on characteristics of the input material. The simulation program may have a means to simulate process variability, and may have a means to update its knowledge of the future variability based on historical data and user input parameters. Process variability may arise from biological variability, human operator variability, and/or machine variability. The simulation program may prevent the start of a run if it predicts that conflicting will occur, and may indicate when manual steps may need to be performed by an operator (for example taking samples to an external QC lab). The user interface 15 may also have a means to alert the user as to the minimum time that must be waited until the next patient run can be commenced and to highlight all of the interdependencies of the operations.

It is possible that the automated system 1*a* will move outside of verified parameters due to human errors during setup, interference on the manufacturing line, unexpected movement of parts, variability in the length of a bioprocess, variability in the arrival of input material, and/or noise in the manufacturing system. Furthermore, the software in the processing and control unit 38 is necessarily complex with many complex functions running simultaneously in parallel. This can make the bioprocessing system 1 difficult to verify and validate, particularly when there is a need to meet certain reliability and safety requirements. In order to address this issue, the processing and control unit 38 may also run a verification program (or "witness system") to validate whether the bioprocessing system 1 is correctly performing as intended. For example, the verification program may confirm that the correct sequence of actions has been performed and may compare the actual locations of robotic devices 2, tubes 150, connections, and fluidics to their intended locations. If the verification program observes that the automated system 1*a* is not performing as intended, then it flags an error and/or raises an alarm. The processing and control unit 38 may use the verification program in combination with the simulation program to determine whether the automated system 1*a* is likely to become out of specification in the future, and/or to predict future performance If the predicted future performance is likely to be outside specification, the processing and control unit 38 may raise an alarm or take action to bring the automated system 1*a* back within specification. Preferably, the verification program receives data inputs from a separate set of sensors to those used in the machine vision system 35 and preferably is run as a separate process, in order to avoid any single point of failure. In other words, the machine vision system 35 may comprise a separate subset of cameras and/or sensors that provide inputs to the verification program.

By enabling reversible fluid connections between the consumables 13, each consumable 13 may have a simpler construction than previous consumables, allowing them to be manufactured at a low cost. Since the automated (robotic) system 1*a* can perform all the steps required to execute a complete cell therapy process without human intervention, human error can be eliminated, and the automated (robotic) system 1*a* can perform the steps very reliably. Furthermore, since all the consumables 13 can be disconnected and reconnected at any time, multiple cell therapy processes can be performed in parallel. Similarly, an operator can instruct the bioprocessing system 1 to begin a new therapy process at any time as long as the bioprocessing system 1 is not full.

Additionally, since any two consumables 13 can be connected by the robotic device 2, the process can easily be adapted to introduce additional steps or to perform an entirely different cell therapy method. To do so, the bioprocessing system 1 could be programmed to included different or additional steps and make use of additional consumables 13 or stations 20. For example, the bioprocessing system 1 could perform cell therapy methods such as CAR-T, NK cells, Treg therapies, HSCs or any other suitable process.

An example of a cell therapy process that can be performed by the bioprocessing system 1 will now be described.

First, an operator loads a set of consumables 13 via the loading hatch 16. These consumables 13 comprise a processed blood sample contained in a patient leukapheresis pack (leukopack), bags for media and reagents, and a bag to receive waste products.

After loading the consumables 13, the operator programs the desired cell therapy process via the user interface 15. Initially, the robotic device 2 places the leukopack into the thawing station 4 to thaw the contents of the leukopack. Subsequently the end effector 100 of the robotic device 2 manipulates an aseptic connection between the leukopack and a consumable 13, and the pumping unit 30 transfers the contents of the leukopack into a consumable 13 via the aseptic connection. The robotic device 2 moves this consumable 13 into the cell washer 6, which may be a centrifuge such as a drum based centrifuge 6, counterflow centrifuge, or spinning membrane type device. The robotic device 2 sequentially makes a number of connections between the consumable 13, the media bag, and the waste bag to wash the sample multiple times with a buffer solution. For example, the consumable 13 may be washed three times in this way. Then the blood sample is moved from the consumable 13 to a temporary holding bag, such that density gradient media are added from one of the reagent bags to the consumable 13, before the blood sample is returned to the consumable 13 where density gradient separation is performed.

Now the blood sample is transferred to a fresh consumable 13, where further aseptic connections are made by the robotic device 2 in order to add activation reagents. The robotic device 2 gently rocks and/or rotates the consumable 13 to mix the activation reagents with the blood sample, before transferring the consumable 13 to the incubator 12 for 24 hours. Then the consumable 13 is removed from the incubator 12, and the blood sample is transferred to a retronectin-containing consumable 13 where a viral vector is subsequently added. This consumable 13 is returned to the incubator 12 for 24 hours. After the robotic device 2 removes the consumable 13 from the incubator 12, the robotic device 2 transfers the blood sample into a consumable 13 suitable for use in the centrifuge 6. After the consumable 13 is removed from the centrifuge 6, the blood sample may be washed again several times by adding buffer solution from the media bag and removing waste to the waste bag.

The blood sample is then moved to an expansion vessel consumable 13 connected to a perfusion system and placed in the incubator 12 for seven days for cell expansion. Finally, the blood sample is removed from this consumable 13, transferred to another consumable 13 so that the blood sample can be concentrated in the centrifuge 6, before being transferred to an infusion bag where cryoprotectant and other formulation additives are added. This infusion bag is then placed in the controlled rate freezer 10 and cryopreserved, before being returned to the operator through the loading hatch 16.

While the above exemplary automated process follows a number of steps and requires the use of multiple consumables 13, each of the consumables 13 can be very simple in its form. For example, the bags for media and reagents may be like the consumable 300 shown in FIG. 7A, which has an inlet/outlet 301 where a tube 150 is connected. FIG. 7B shows a consumable 310 suitable for use in the centrifuge 6, which as well as having an inlet/outlet 311, it also has a sterile air filter 312, and a vacuum actuated bung 313 to pull fluid in a chamber during use of the centrifuge 6. Examples of suitable consumables, centrifuge vessels and centrifuges can be found in EP1144026 and U.S. Pat. No. 10,562,041, and as they are well known, there is no need to described them further herein. FIG. 7C shows a consumable 320 appropriate for use as an expansion vessel for the cell expansion step. It has an inlet 321 for media 326, an outlet 322 for waste, and an inlet/outlet 323 for cell inoculation, sampling, and/or cell harvest. The expansion vessel 320 contains cells 325 and a gas permeable membrane 324. As already discussed, these consumables 13 can be manufactured much more reliably and at a much reduced cost compared to prior art consumables. The bioprocessing system 1 can therefore provide an automated cell therapy process without (substantial) human intervention.

With reference to FIGS. 8A to 8L, a preferred embodiment of a method of manipulating fluidic aseptic connections between tubes 150 is described in detail. Here, the robotic device 2 of the bioprocessing system 1 comprises a robotic arm 3 having an end effector 100. The end effector 100 is attached to the robotic arm 3 and has two gripping units 110a, 110b. The gripping units 110a, 110b may be the grippers 55 of gripping unit 50 described earlier, or could be separate gripping units. The end effector 100 is configured to connect a first tube 150a and a second tube 150b together while maintaining a seal between the inside of the tubes 150a, 150b and the surroundings (i.e. the contents of the tubes and consumables are not exposed to the atmosphere). Each tube 150a, 150b connects to a respective consumable 13 (not shown). As used herein, the term "upstream" refers to a direction along the tubes 150a, 150b towards the first end of the tubes 150a, 150b that attaches to a respective consumable 13. Similarly, the term "downstream" refers to a direction along the tubes 150a, 150b towards the second "free" end of the tubes 150a, 150b. On each tube 150a, 150b, there is mounted a tube holder 130a, 130b, which can easily be gripped by the gripping units 110a, 110b. The tube holders 130a, 130b may equivalently be referred to as "holding devices" or "holders". The tube holders 130a, 130b can be moved along the tubes 150a, 150b via rotation of precession wheels 135a, 135b (i.e. to translate the tube 150 relative to its respective tube holder 130). The end effector 100 comprises a clamping unit 105 with a first jaw 120 and a second jaw 125 each divided into a first part 120a, 125a, and a second part 120b, 125b. The end effector 100 also comprises a blade 140 that can be moved between the parts of each jaw 120, 125 along a cutting plane.

Figure 8A:
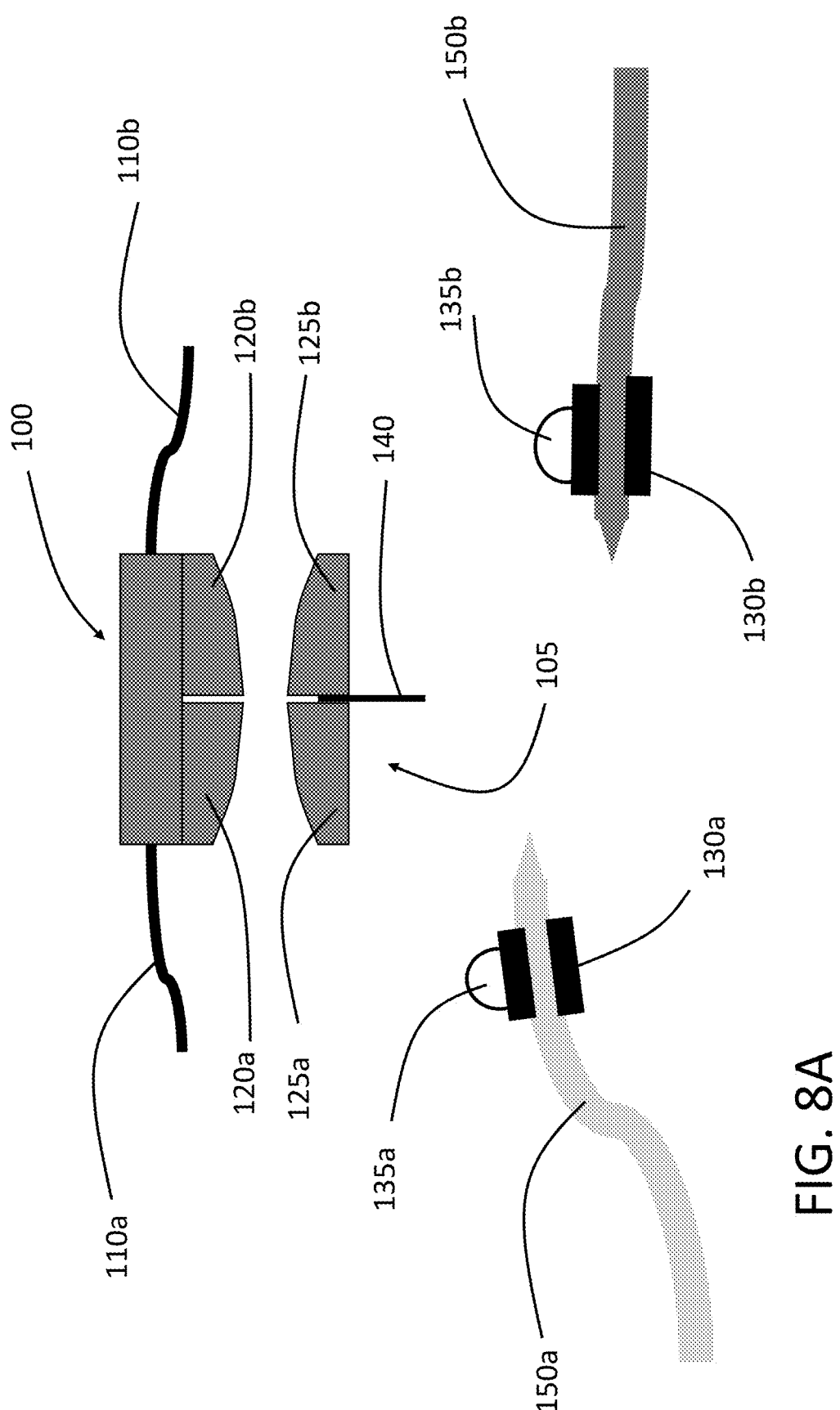
FIGS. 8A to 8L show a first embodiment of an apparatus for forming aseptic connections between tubes in the automated bioprocessing system, at various steps along the connection process.
Figure 8B:
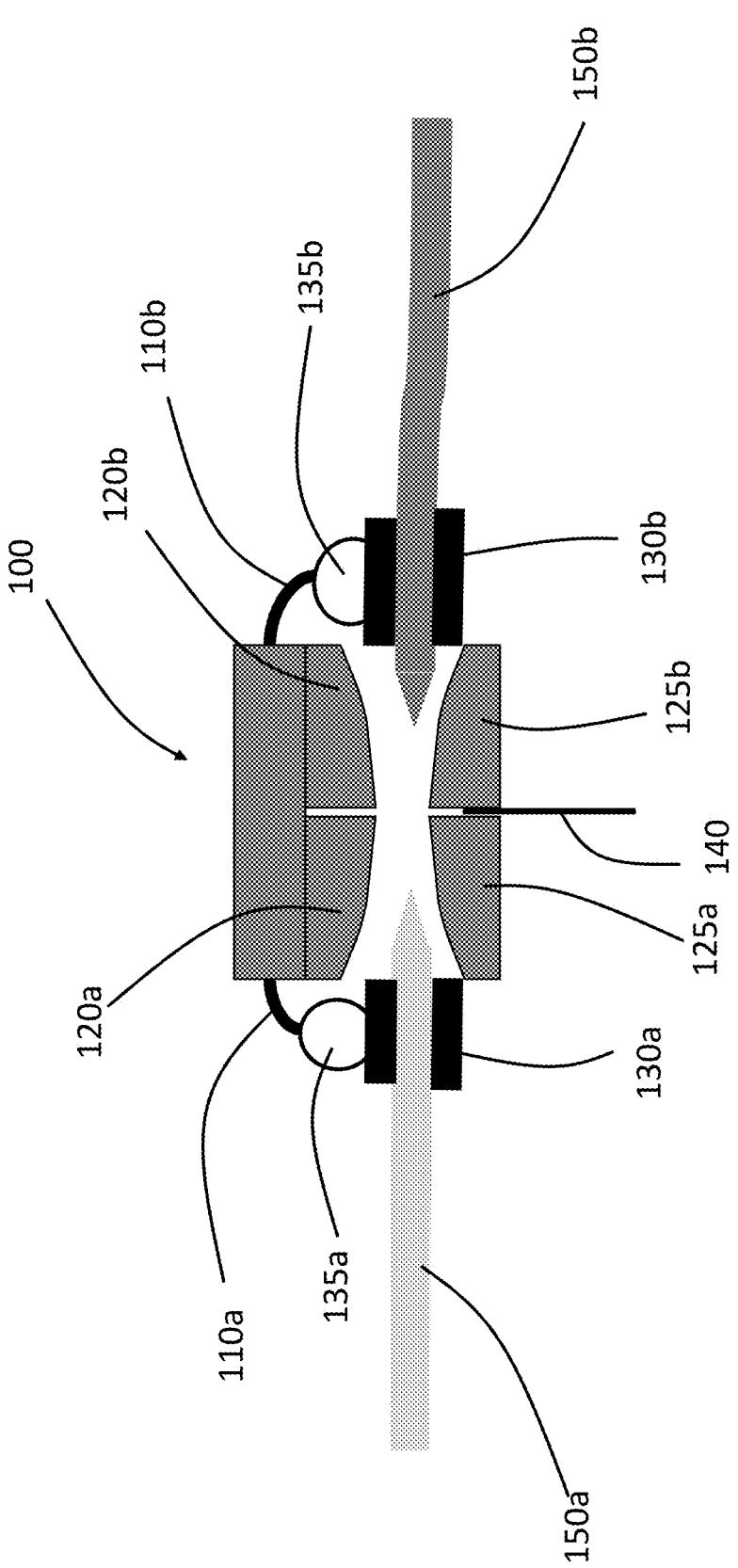

In FIG. 8B, the gripping units 110a, 110b are shown to grip the respective tube holders 130a, 130b on the respective tubes 150a, 150b, and the tubes 150a, 150b have been positioned adjacent the clamping unit 105, with the jaws 120, 125 of the clamping unit 105 in an open position.

Figure 8C:
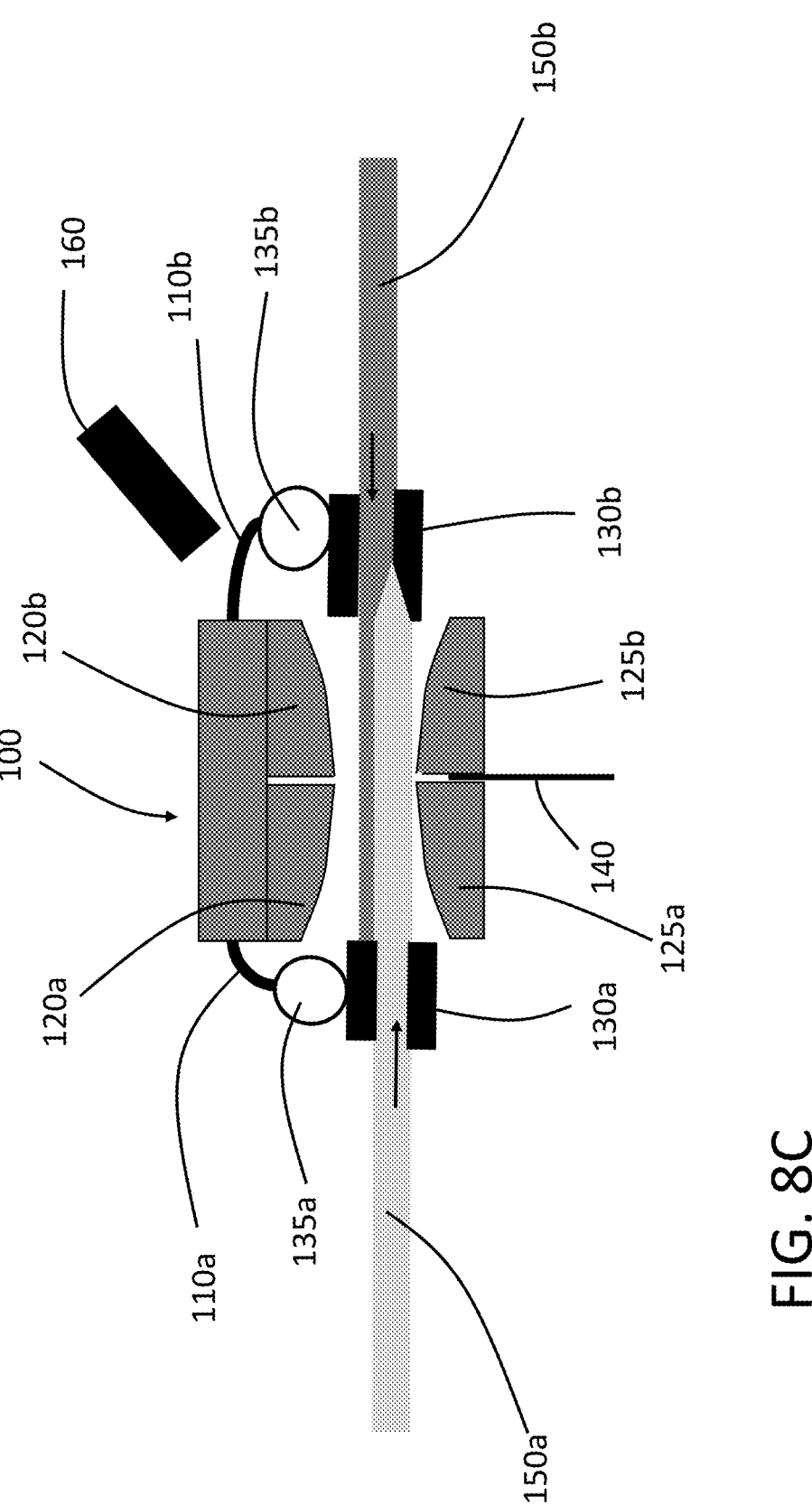

In FIG. 8C, the precession wheels 135a, 135b rotate to advance the tubes 150a, 150b through the jaws 120, 125. A camera 160 is used to confirm that each tube 150a, 150b is correctly positioned in the clamping unit 105, and that both tubes 150a, 150b cross the cutting plane. The tube holders 130a, 130b, may contain magnets to facilitate alignment of the tubes 150a, 150b in the clamping unit 105. The jaws 120, 125 of the clamping unit 105 may be coated with a low friction material, such that the tubes 150a, 150b slide within the clamping unit 105 and Poisson's ratio effects are minimised.

Figure 8D:
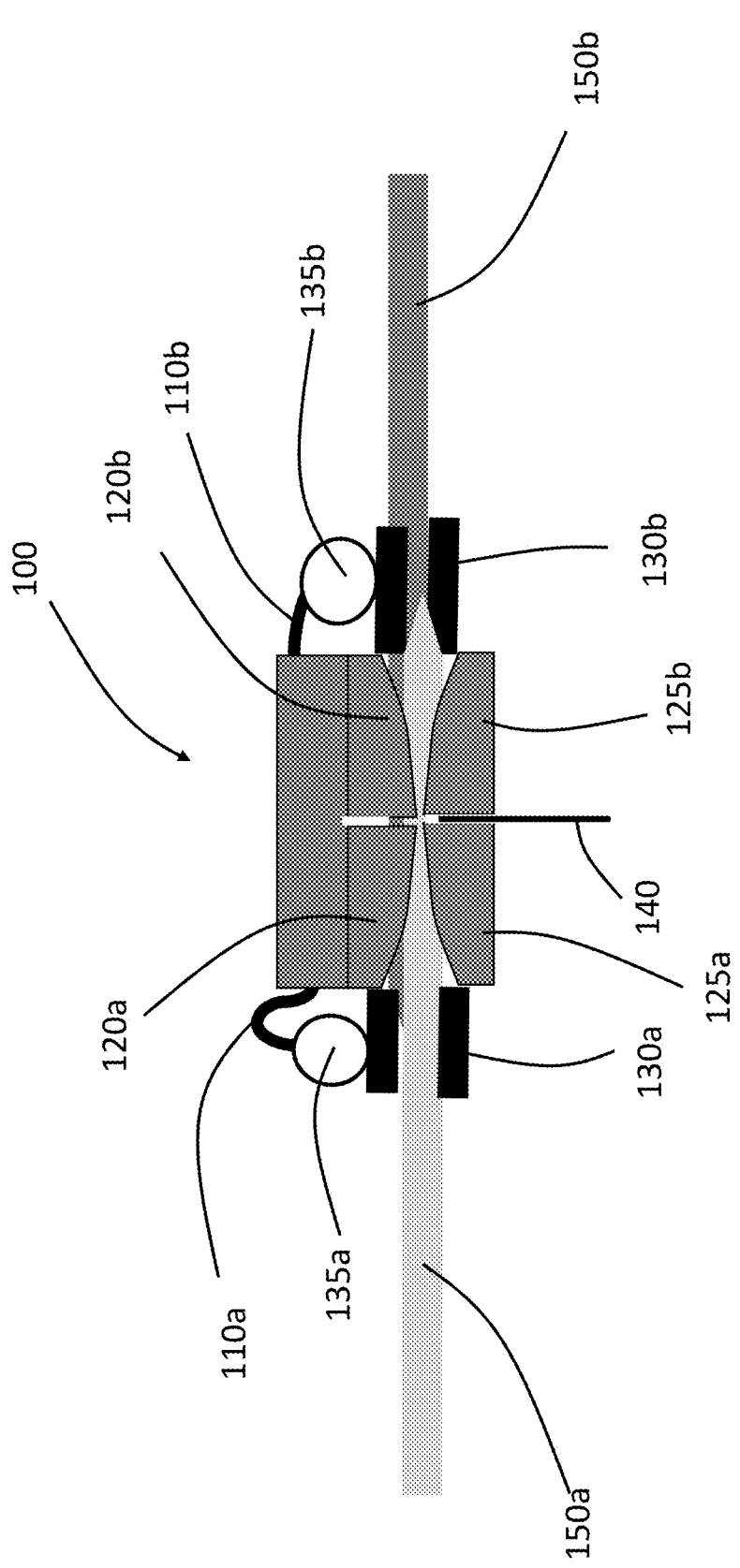

In FIG. 8D, the jaws 120, 125 of the clamping unit 105 are clamped together to pinch the tubes 150a, 150b flat at the cutting plane, thereby preventing any flow of fluid through the tubes 150a, 150b. Since the dimensions of all the tubes 150 in the bioprocessing system 1 are identical, the jaws 120, 125 of the clamping unit 105 are constructed to be stiff so that they fully encase the tubes 150a, 150b when clamped, with controlled tolerances to fully define tube form factor and alignment, irrespective of the tube tolerances. The tubes 150 may have pre-moulded flange regions, such as large flat flange regions to facilitate alignment with the clamping unit 105.

Figure 8E:
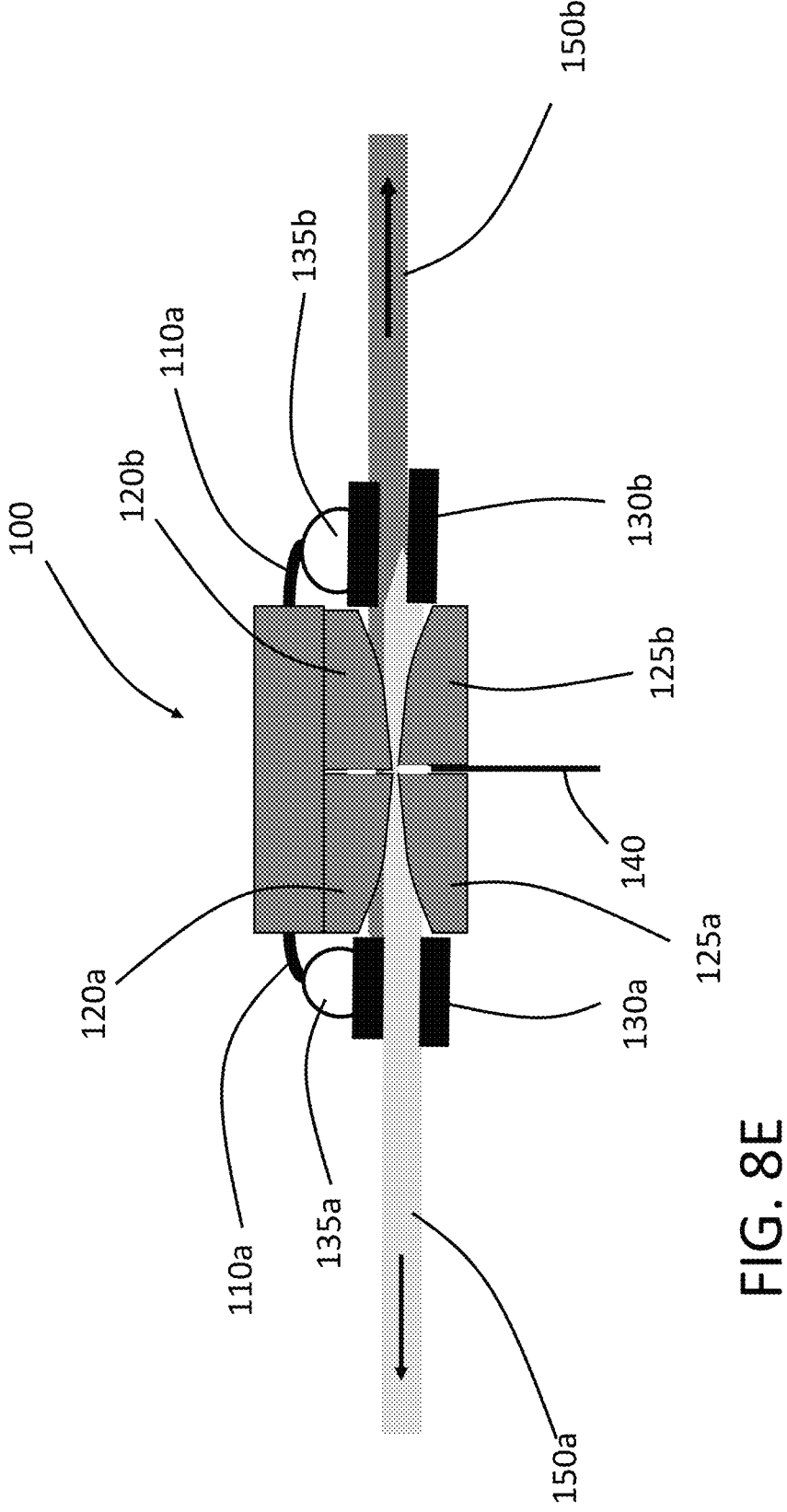

In FIG. 8E, the pumping unit 30 is used to pump fluid away from the clamping unit 105 in the direction of the arrows. This ensures that both the tubes 150a, 150b are fully dry at the cutting plane, and helps to further collapse the tubes 150a, 150b and keep them pinched shut.

Figure 8F:
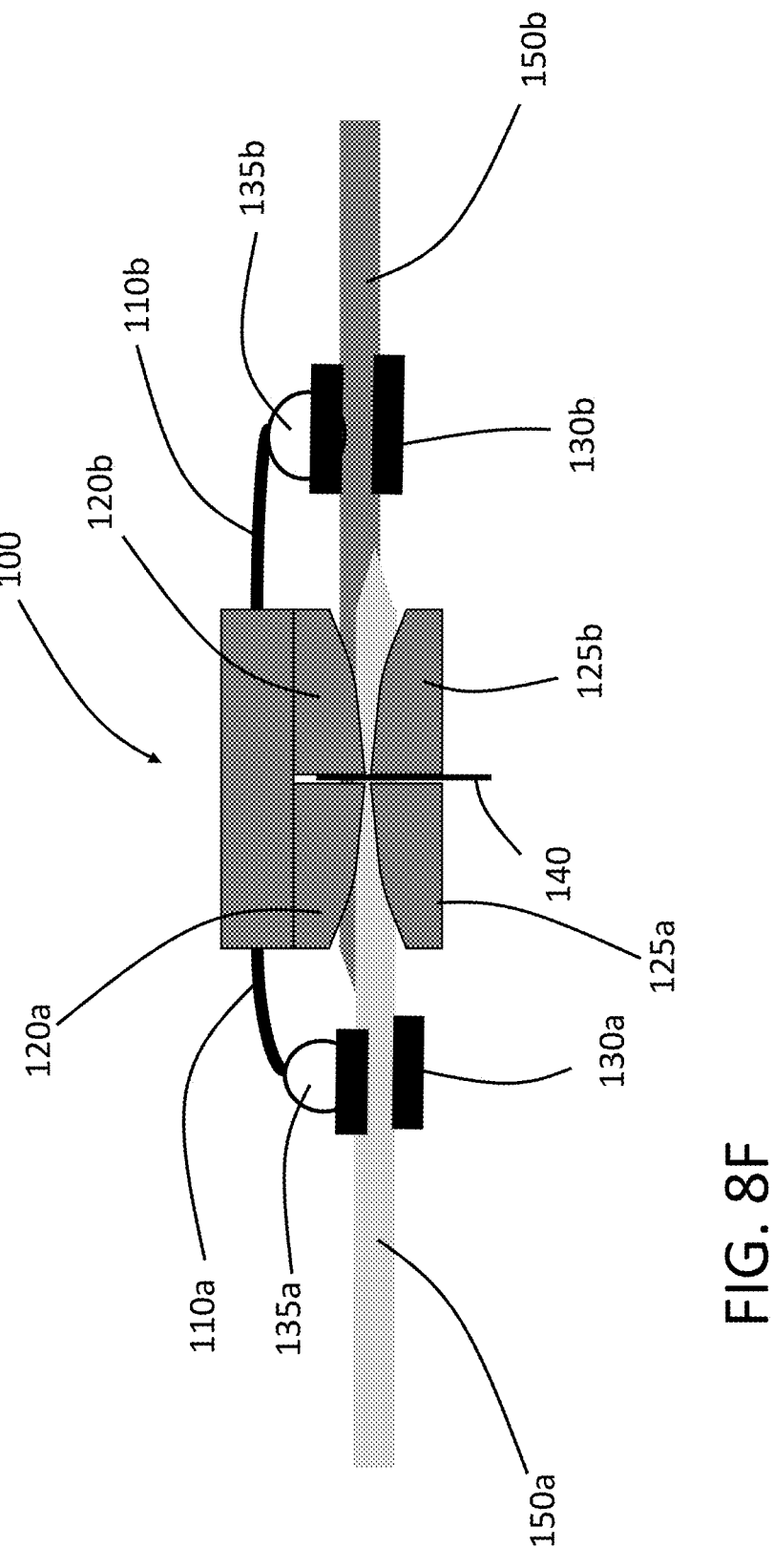

In FIG. 8F, the blade 140 is heated by a heat source (not shown) to between 300° C. and 400° C. to sterilise and depyrogenate the blade 140. The heat source may use resistive heating to heat the blade 140 or a mounting block (not shown) in contact with the blade 140, or the blade 140 may be heated without direct contact such as through a laser heater. The blade 140 is allowed to cool partially before moving the blade 140 along the cutting plane between the first parts 120a, 125a and second parts 120b, 125b of the jaws 120, 125, thereby cutting through the tubes 150a, 150b.

Figure 8G:
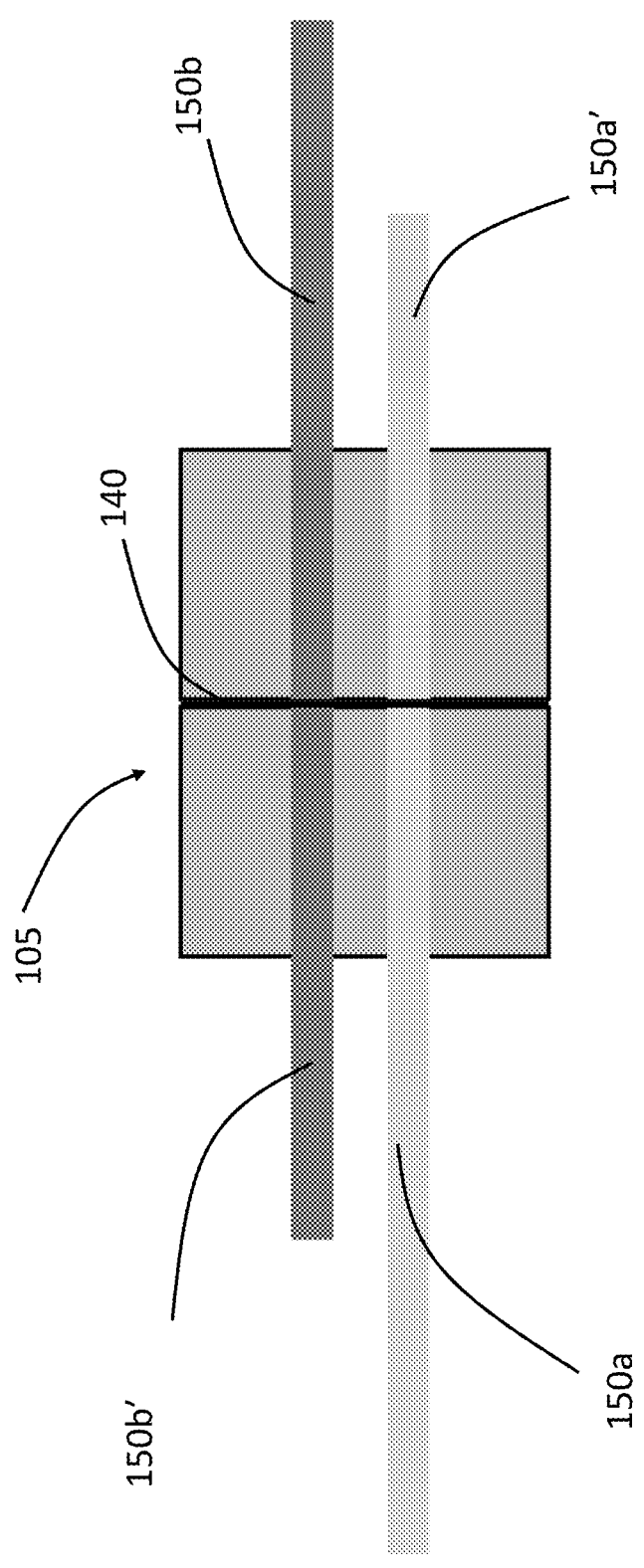

FIG. 8G depicts a cutaway through the clamping unit 105 viewed from above after the blade 140 is moved along the cutting plane to cut the tubes 150a, 150b. As a result, the first tube 150a is cut into a first part 150a connecting to its respective consumable 13, and a second part 150a ' which previously led to the sealed end of the tube 150a. Similarly, the second tube 150b is cut into a first part 150b connecting to its respective consumable 13, and a second part 150b ' which previously led to the sealed end of the tube 150b.

Figure 8H:
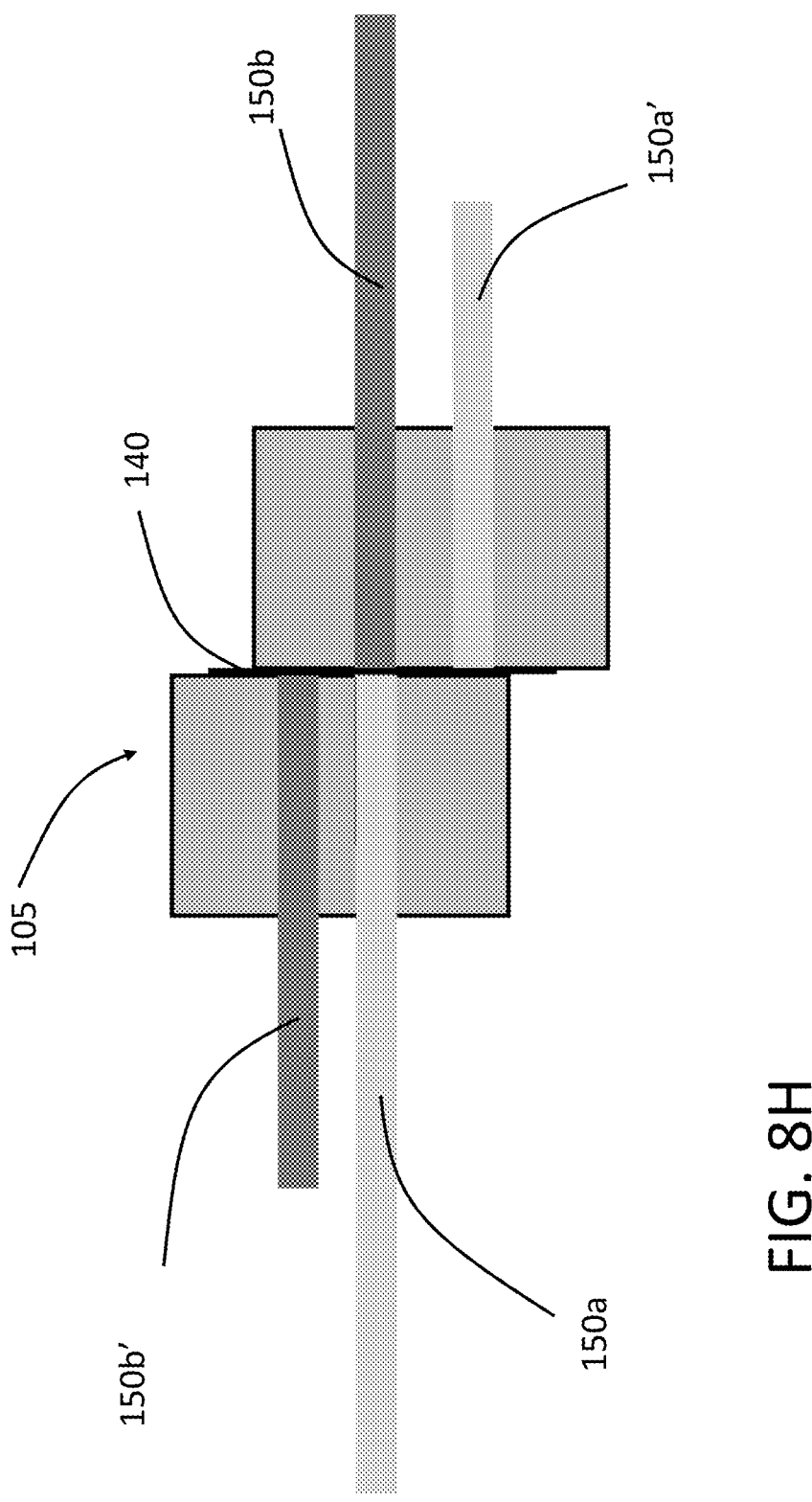

In FIG. 8H, the first parts 120a, 125a of the clamping unit 105 are moved relative to the second parts 120b, 125b of the clamping unit 105 to align the parts of the first tube 150a and second tube 150b that connect to their respective consumables 13. The blade 140 remains between the first tube 150a and the second tube 150b, and transfers the heat from the heat source to melt the ends of the tubes 150a, 150b. The blade 140 may be held between the tubes 150a, 150b for a predetermined time period and may have a predetermined heat profile. In this example, the first parts 120a, 125a translate relative to the second parts 120b, 125b of the clamping unit 105 in order to align the tubes 150a, 150b, but is should be appreciated that the alignment could also be performed in other ways, such as by rotating one of the parts of the clamping unit 105 relative to the other part. An infra-red camera or infra-red laser could be used in a closed loop to confirm that the ends of the tubes 150a, 150b have reached the correct temperature for welding and that a uniform temperature is reached. Alternatively, a thermistor, a thermocouple, or a resistance temperature detector (RTD) may be mounted on a component such as the blade 140, the mounting block or the heat source in order to monitor the temperature.

Figure 8I:
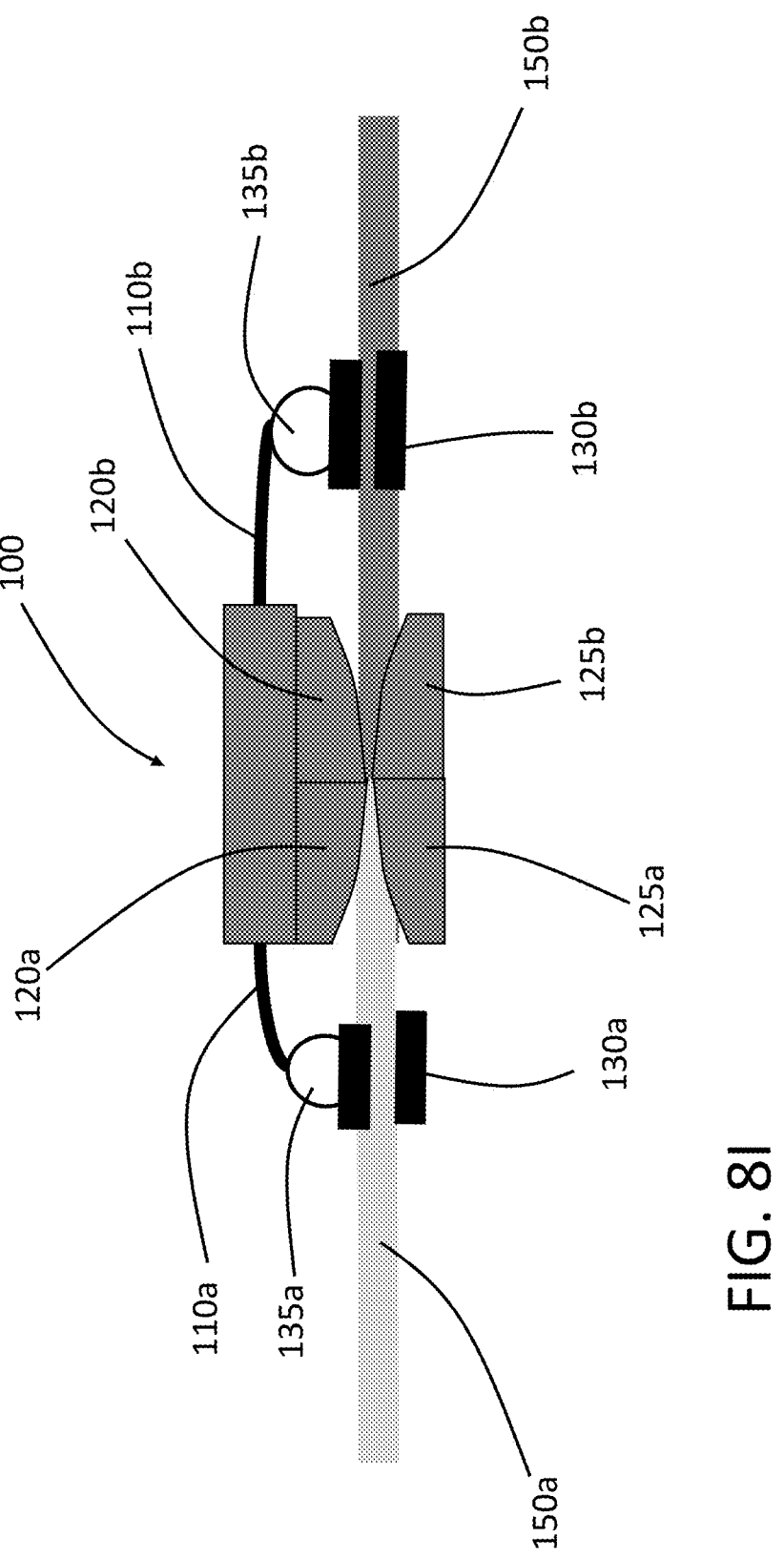

In FIG. 8I, the blade 140 is removed from between the first parts 120a, 125a and second parts 120b, 125b of the jaws 120, 125, and the clamping unit 105 brings the two tubes 150a, 150b into contact by translating the first parts 120a, 125a and second parts 120b, 125b towards each other. The heat that was previously transferred to the tubes 150a, 150b by the blade 140 welds the tubes 150a, 150b together.

Figure 8J:
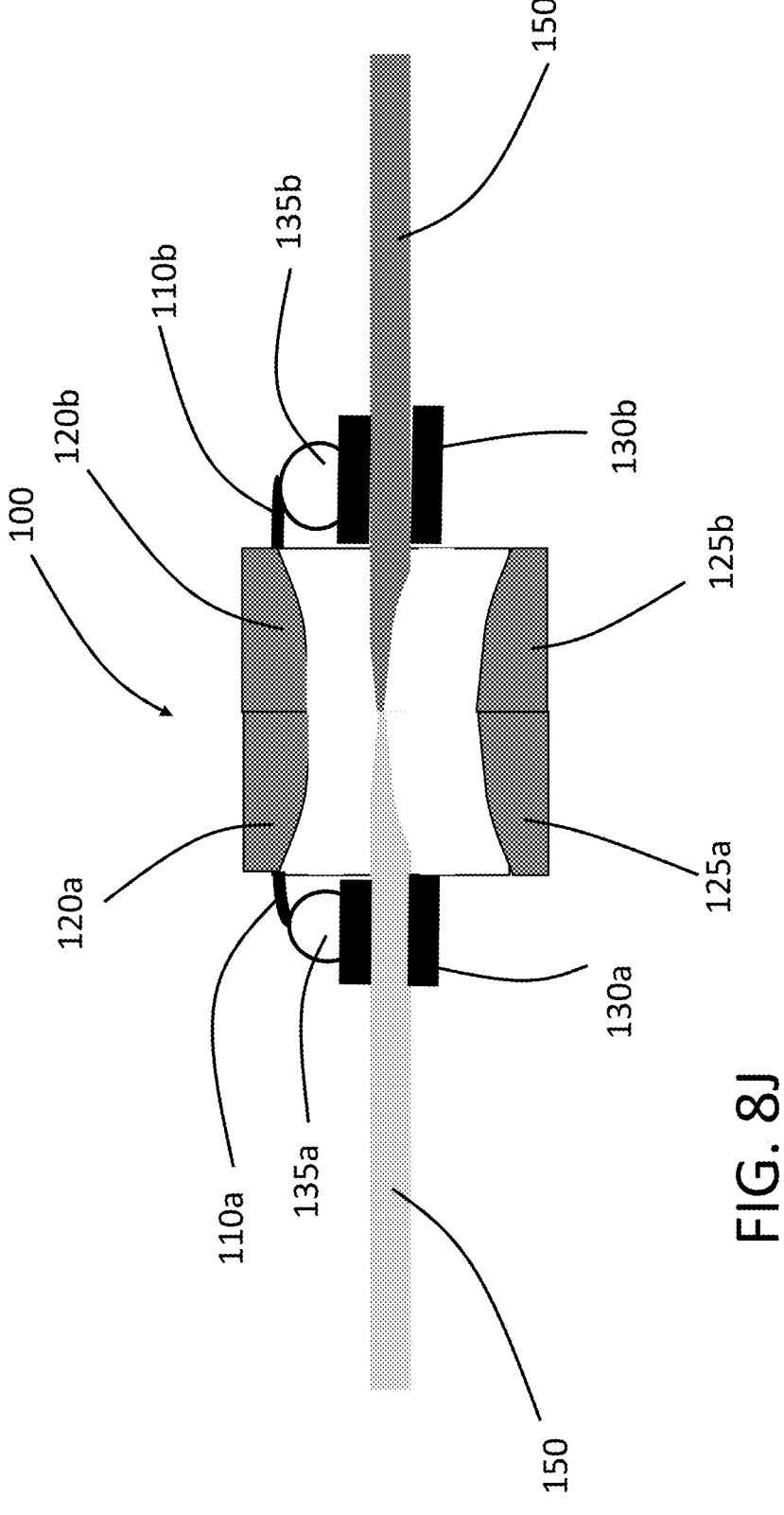

In FIG. 8J, the first jaw 120 and second jaw 125 of the clamping unit 105 are moved apart to unclamp the tubes 150a, 150b, which are now connected together to form a single tube 150.

Figure 8K:
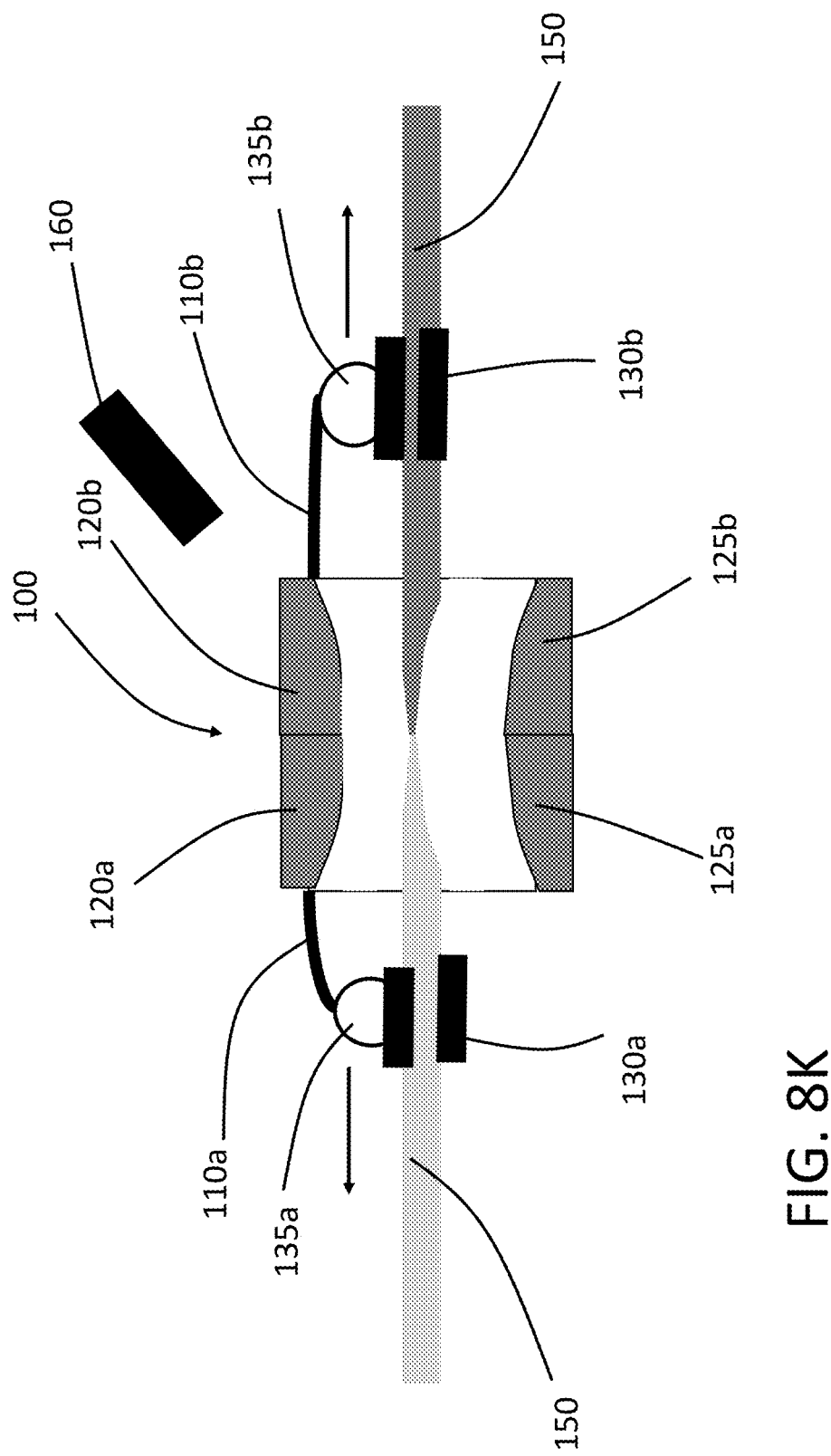

In FIG. 8K, the camera 160 is used to inspect the connection between the two tubes 150a, 150b. The camera 160 has a microscope lens and is connected to a processing unit (not shown) which identifies if a weld is successful, and the camera 160 may be able to detect infra-red (IR) radiation. The precession wheels 135a, 135b may be rotated to apply a tensile force to the tube 150 in the direction of the arrows, and can simultaneously measure a stress-strain profile of the tube 150. The stress-strain profile may also be analysed by the processing unit to confirm whether the weld is successful.

Other mechanical tests may be used, such as a torsion test or a vibration test, for example. An ultrasound source or X-ray source may also be used to test for the presence of cavities in the connection. Fluid may also be pumped through the tube 150, and the camera 160 may be used to detect the presence of a leak. Alternatively, the connection may be located in a sealed container with a pressure sensor that indicates a leak by detecting a pressure change inside the container or alternatively using a sniff detector to measure the change in concentration of water in the air. Alternatively, external air pressure may be supplied to the sealed container and the camera 160 may observe whether air leaks into the connection. Alternatively, air may be pumped into the tubes 150a, 150b prior to welding, and then a vacuum could be applied in the sealed container to see whether air leaks out. A biocompatible die may be added to the outside of the weld. If the processing unit determines that the weld is not successful, the tube 150 may be re-clamped and re-welded. The inspection of the connection may be performed before the tubes 150a, 150b are released by the clamping unit 105. By keeping the tubes 150a, 150b pinched during inspection, even if a leak is present at the connection, the contents of the consumables 13 still remain isolated from the surrounding air and atmosphere.

Figure 8L:
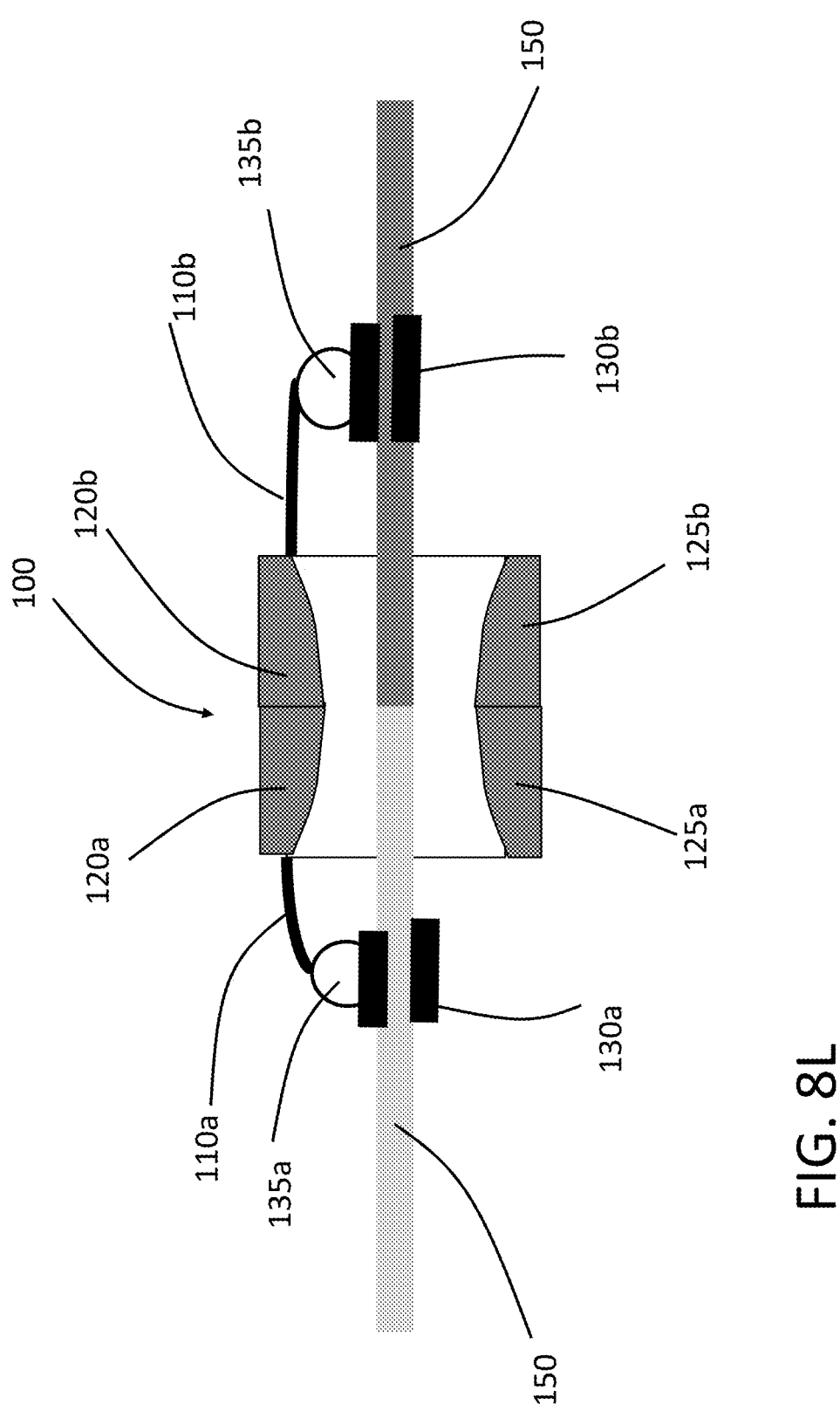

In FIG. 8L, the tube 150 is still pinched at the connection point leading to a kink that prevents flow of fluid through the tube 150. In order to open out the kink, the tube 150 is manipulated perpendicular to the direction in which the tube 150 was pinched by the clamping unit 105 in order to open the tube 150 to allow fluid flow past the connection point. The manipulation may be performed by one of the gripping units 110a, 110b, or by a separate gripping unit attached to the robotic arm 3. Alternatively, the gripping units 110a, 110b may rotate the tube 150 by 90° inside the clamping unit 105 and partially re-clamp the tube 150 to remove the kink. There are other methods to open the tube 150, such as by applying a vacuum outside the tube 150, or by embedding magnets into the tube 150, welding a spring into the tube 150 to open the tube 150 when the clamping unit 105 releases the tube 150, or by embedding a shape memory allow into the tube 150, which can be actuated to change the shape of the tube 150. The inspection step described previously may also be performed after the tubes 150a, 150b are opened, which may provide a better functional test for the tubes 150a, 150b. Preferably the inspection step is performed both before the tubes 150*a*, 150*b* are released by the clamping unit 105, and after the tubes 150*a*, 150*b* are opened to allow fluid flow.

Now that the connection between the original tubes 150*a*, 150*b* is complete, the pumping unit 30 can be operated to pump fluid through the tube 150 between the consumables 13 in order to perform a step in the cell therapy process.

The disconnection process of the two consumables 13 will now be described with reference to FIGS. 9A to 9D.

Figure 9A:
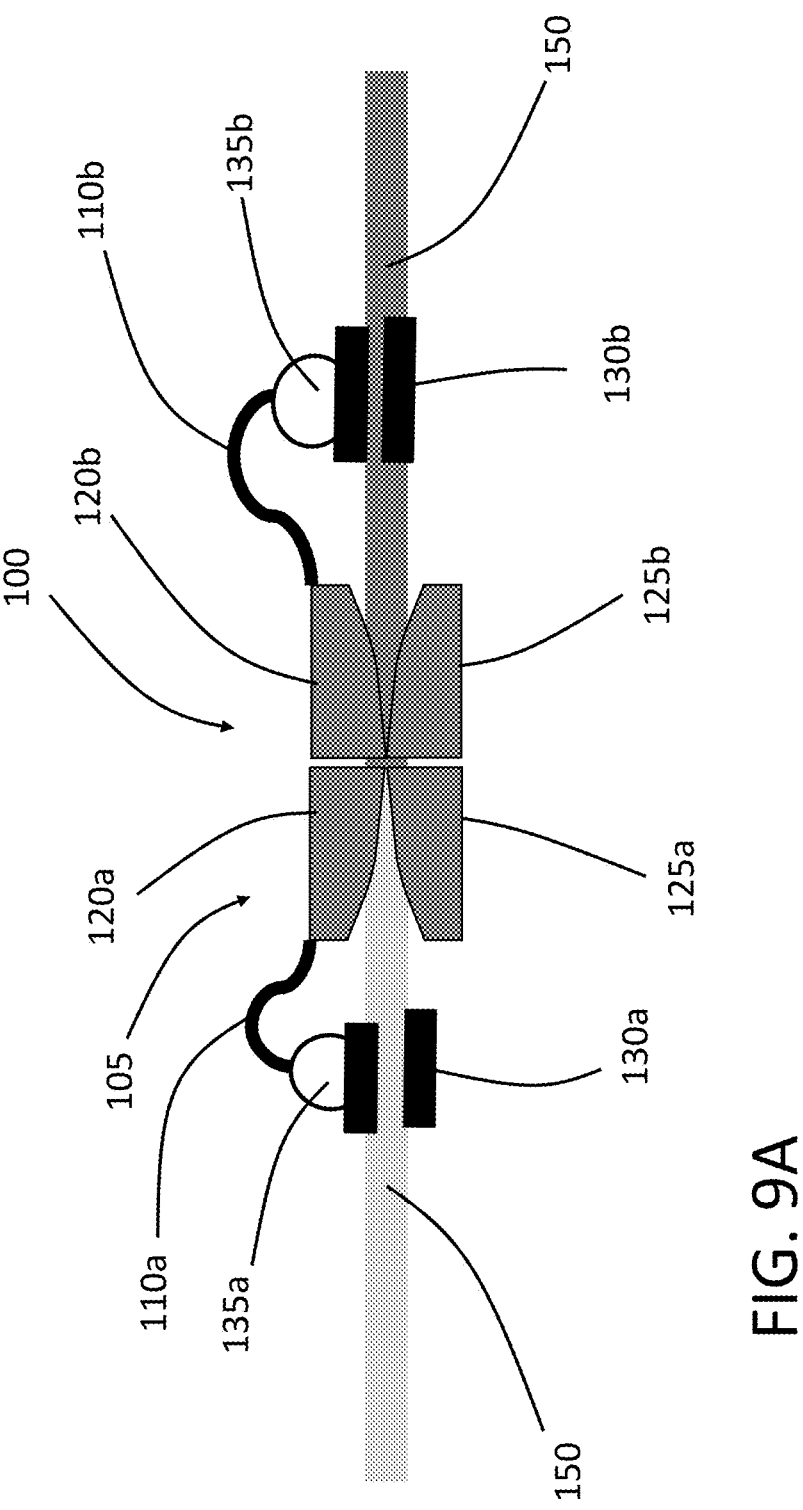
FIGS. 9A to 9D show the first embodiment of the apparatus for forming aseptic connections between tubes in the automated bioprocessing system, at various steps along a disconnection process.
Figure 9B:
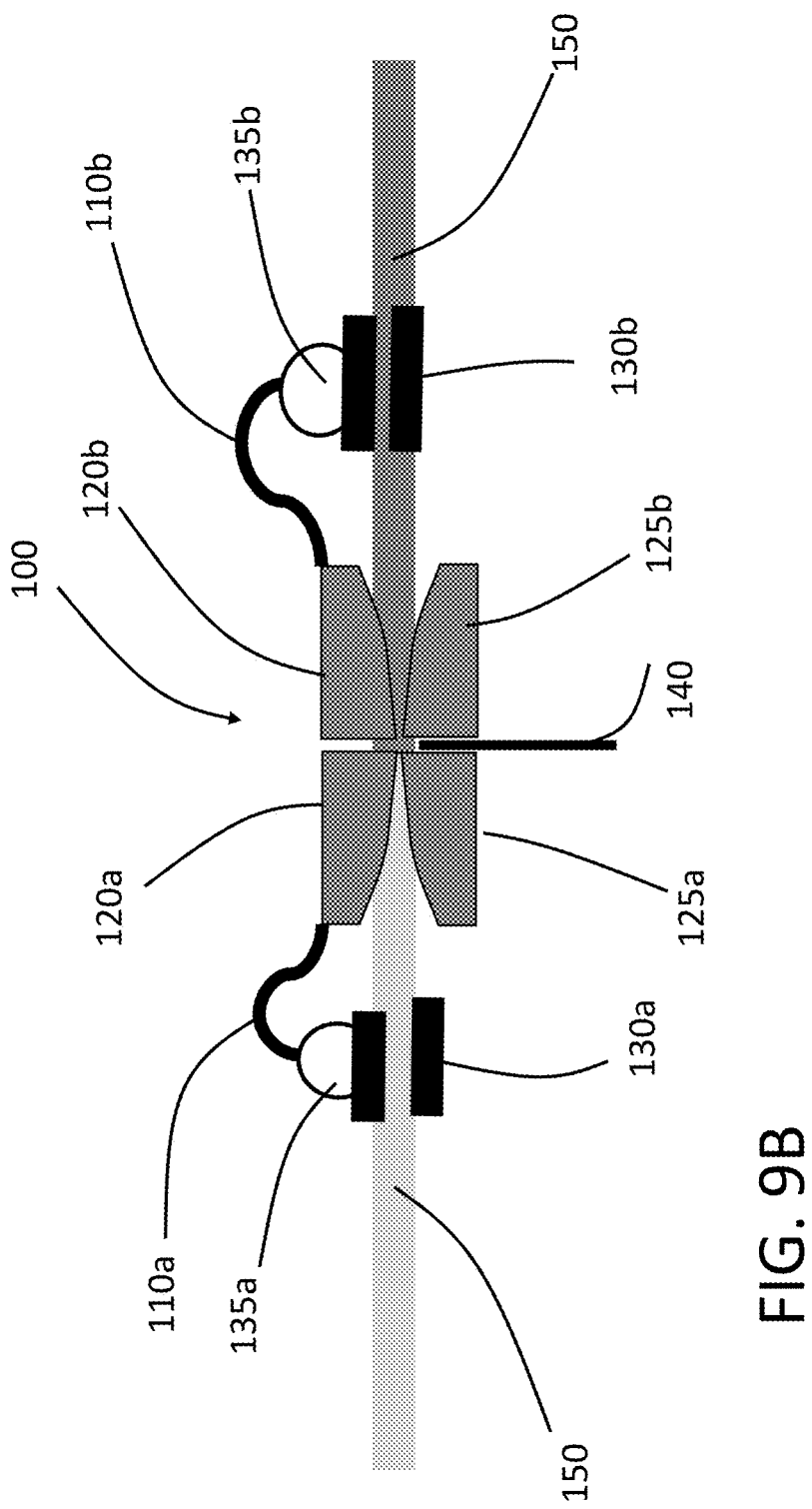
Figure 9C:
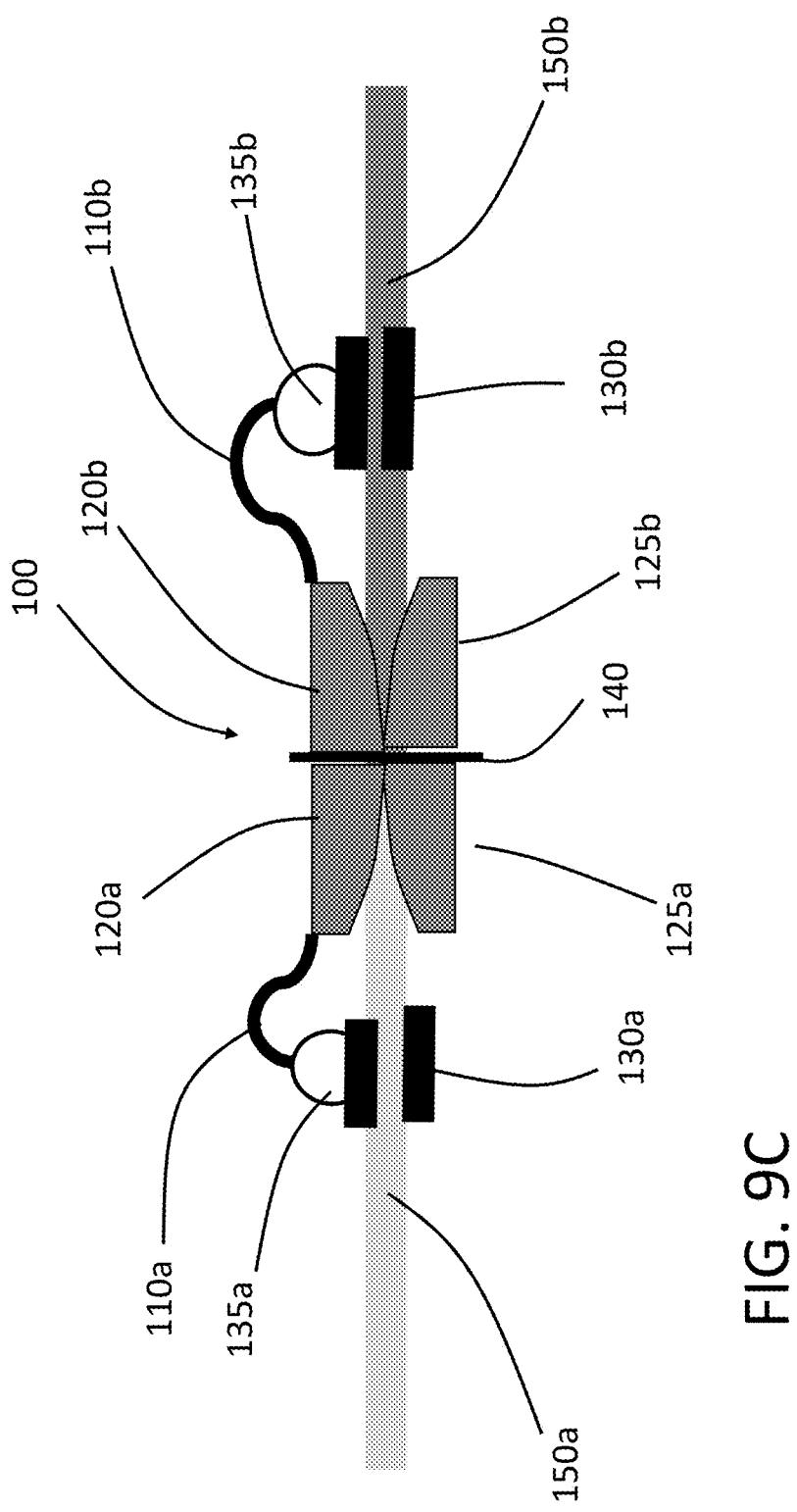
Figure 9D:
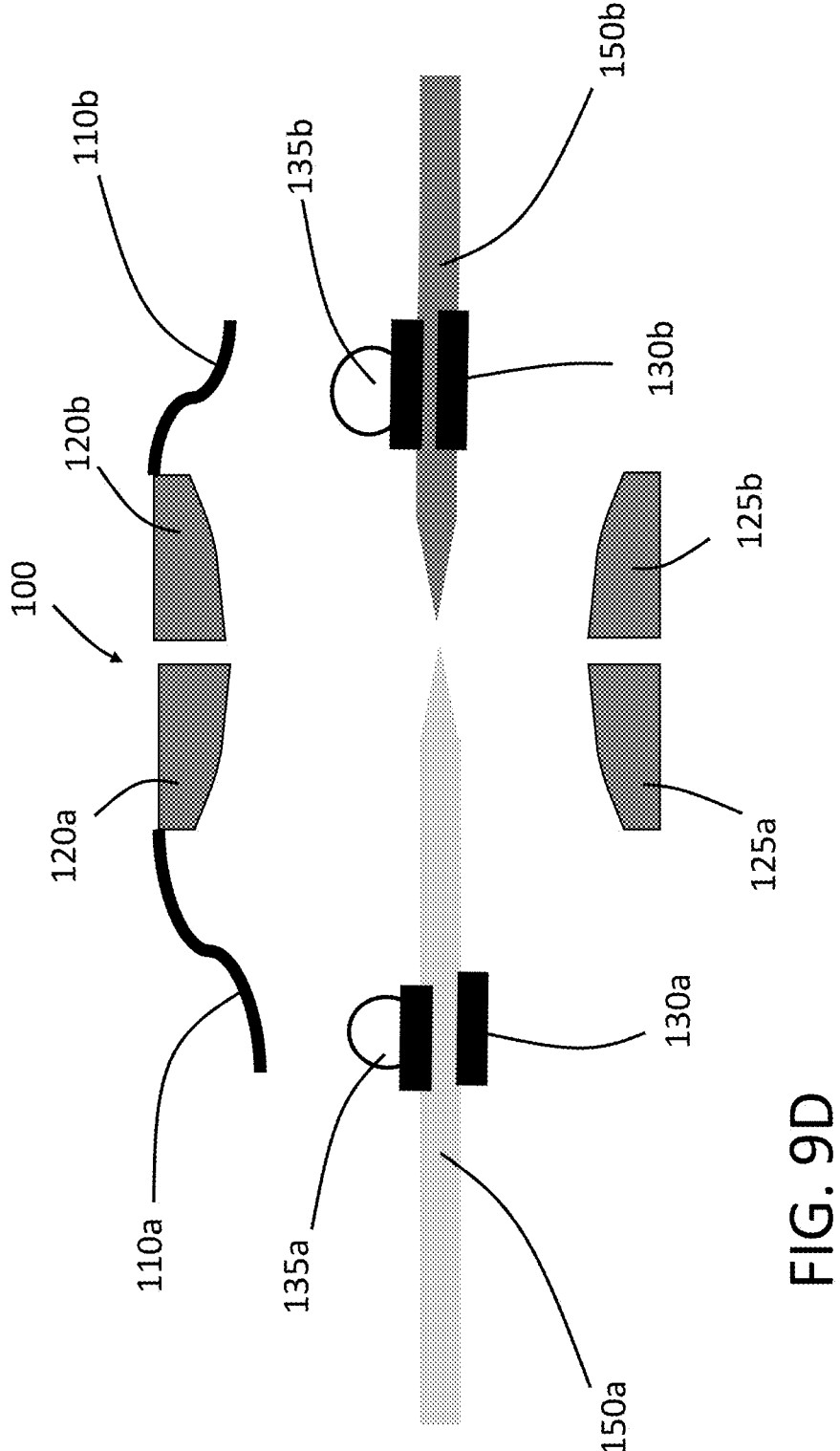

In FIG. 9A, the jaws 120, 125 of the clamping unit 105 are closed to pinch the tube 150 that connects between the two consumables 13 (not shown). The clamping unit 105 for disconnecting the consumables 13 may be located on a different end effector 100 to the clamping unit 105 used to connect the consumables 13. In FIG. 9B, the blade 140 is heated by the heat source (not shown) to between 300° C. and 400° C. to sterilise and/or depyrogenate the blade 140. The heating profile used during disconnection may be different to the heating profile used during connection, in order to better seal the tube. The blade 140 is allowed to cool partially. In FIG. 9C, the blade 140 is moved along the cutting plane between the first parts 120*a*, 125*a* and second parts 120*b*, 125*b* of the jaws 120, 125, thereby cutting the tube 150 into a first tube 150*a* and a second tube 150*b*, each connecting to a respective consumable 13. The blade 140 remains between the tubes 150*a*, 150*b* for a predetermined time period to melt the ends of the tubes 150*a*, 150*b*. The predetermined time period used to melt the ends of the tubes 150*a*, 150*b* during disconnection may be different to the predetermined time period used to melt the ends of the tubes 150*a*, 150*b* during connection. In FIG. 9D, the blade 140 is removed from between the first parts 120*a*, 125*a*, and the second parts 120*b*, 125*b* of the jaws 120, 125 of the clamping unit 105. The jaws 120, 125 of the clamping unit 105 are opened to release the tubes 150*a*, 150*b* from the clamping unit 105. The gripping units 110*a*, 110*b* can now release the tube holders 130*a*, 130*b*, or manipulate the tube holders 130*a*, 130*b* to attach one or both of the tubes 150*a*, 150*b* to a different tube 150 connecting to a separate consumable 13 for a subsequent step in the cell therapy process.

If the end effector 100 for disconnecting the consumables 13 is a different end effector 100 to the one for connecting the consumables 13, different heat sources and/or cutting methods may be used. For example, an electromagnetic (EM) source such as an RF source may be used to seal the tubes 150*a*, 150*b* during the disconnection process. The EM source may be located on a separate robotic arm 3 and may be located on a different robotic device 2. In this way, a tube 150 may be clamped and fluidly sealed by an end effector 100 on a first robotic arm 3, and the EM source may be used to melt through the clamped portion of the tube 150. The EM source may have electrodes that are driven with an alternating current in a MHz or GHz frequency range, preferably at 40.68 MHz. This melts the interior of the tube 150 and seals the tube over a wide area. A blade 140 may subsequently be used to cut through the heat-affected zone and separate the tube 150 into two tubes 150*a*, 150*b*.

Various alternative "non-contact" methods for aseptically connecting and disconnecting two tubes 150*a*, 150*b* will now be described with reference to FIGS. 10 to 14.

FIG. 10A shows two tubes 150*a*, 150*b* to be connected together, each tube 150*a*, 150*b* terminating in a closed end. In FIG. 10B, the heat source directly applies heat to the closed ends of the tubes 150*a*, 150*b* as indicated by the arrows. The heat source may be a source of electromagnetic radiation such as a laser that delivers light at infra-red or radio frequencies. The material that forms the tube 150 may contain additives to improve absorption of laser energy, or the tube 150 may be painted in a material that absorbs laser light. Preferably, the additives enable two-photon polymerisation, which requires a high laser intensity for any activation, and would enable laser light to be non-linearly concentrated on the welding end of each tube 150, even when shown from the outside. Alternatively, the heat source may be a source of ultrasound waves, or the tubes 150 may contain additives that cause them to heat up during use of an induction heater. Any of the above heating methods, including the use of a wire or blade 140 can be used in combination.

In FIG. 10C, the heated ends of the tubes 150*a*, 150*b* are pressed together so that the tubes 150*a*, 150*b* weld together to form a single tube 150. This may be performed by using the precession wheels 135*a*, 135*b* described previously, or by directly manipulating the tubes 150*a*, 150*b* with the gripping units 110*a*, 110*b*. In FIG. 10D, the kink at the connection of the tube 150 is removed using a similar method to those described previously. Inspection and quality control steps like the ones already discussed may also be applied using this process.

Figures 11A, 11B, 11C, 11D:
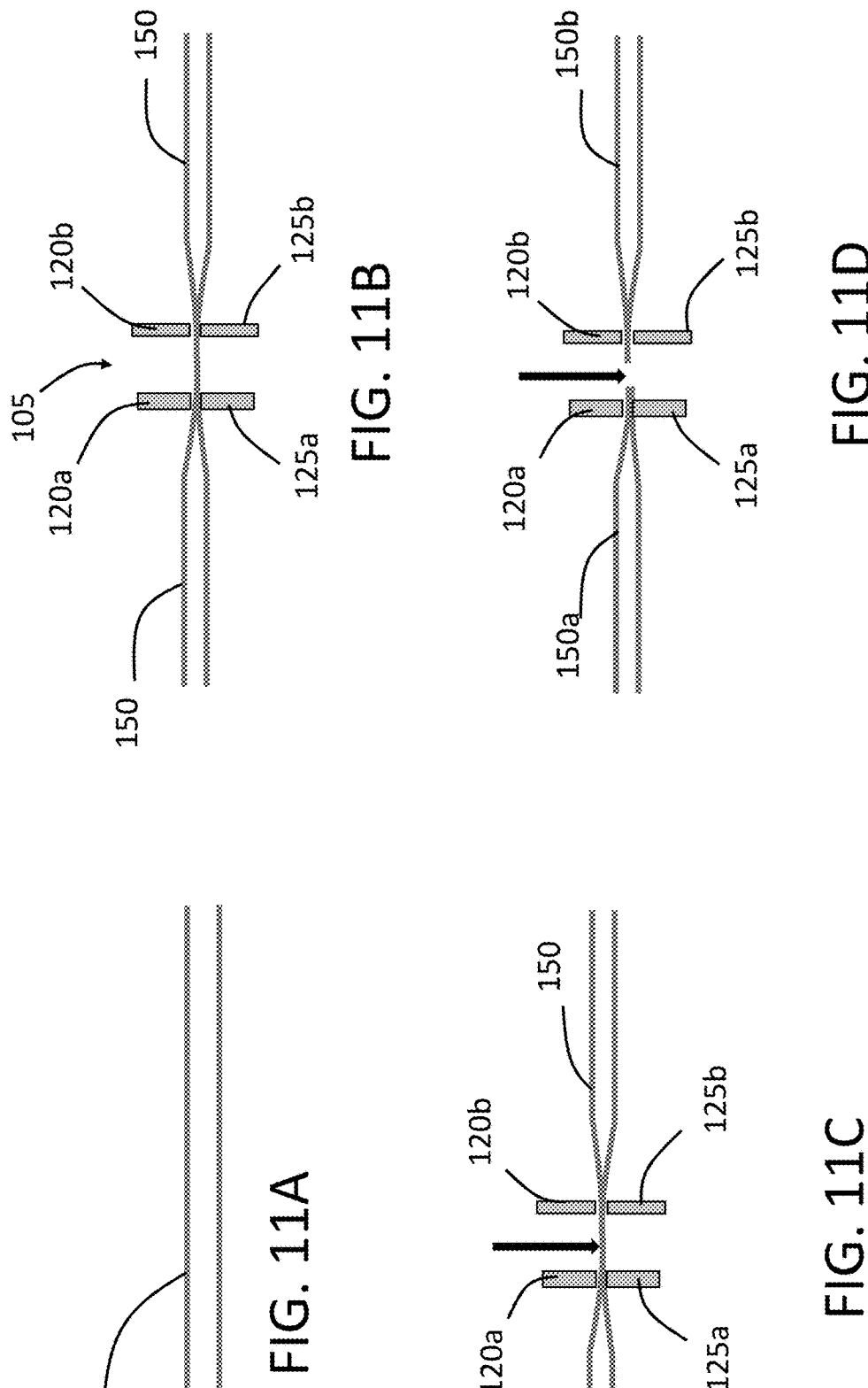
FIGS. 11A to 11D show the second embodiment of the apparatus for forming aseptic connections between tubes in the automated bioprocessing system, at various steps along the disconnection process.

FIG. 11A shows a tube 150 to be disconnected into two parts. In FIG. 11B, the tube is pinched inside a clamping unit 105 like the one previously described, where a first jaw 120 of the clamping unit 105 is divided into a first part 120*a* and a second part 120*b*, and a second jaw 125 of the clamping unit 105 is divided into a first part 125*a*, and a second part 125*b*. A space remains between the first parts 120*a*, 125*a* and the second parts 120*b*, 125*b* of the jaws 120, 125 when the tube 150 is clamped between the first jaw 120 and the second jaw 125. In FIG. 11C, the heat source directly applies heat to the tube 150 between the first parts 120*a*, 125*a* and the second parts 120*b*, 125*b* of the clamping unit 105, as shown by the arrow. As a result, the heat source cuts through the tube 150 into a first part 150*a* and a second part 150*b*. In FIG. 11D, the heat source continues to apply heat to the tubes to ensure that the cut ends of the tubes 150*a*, 150*b* are closed to the surrounding air.

Figures 12A, 12B:
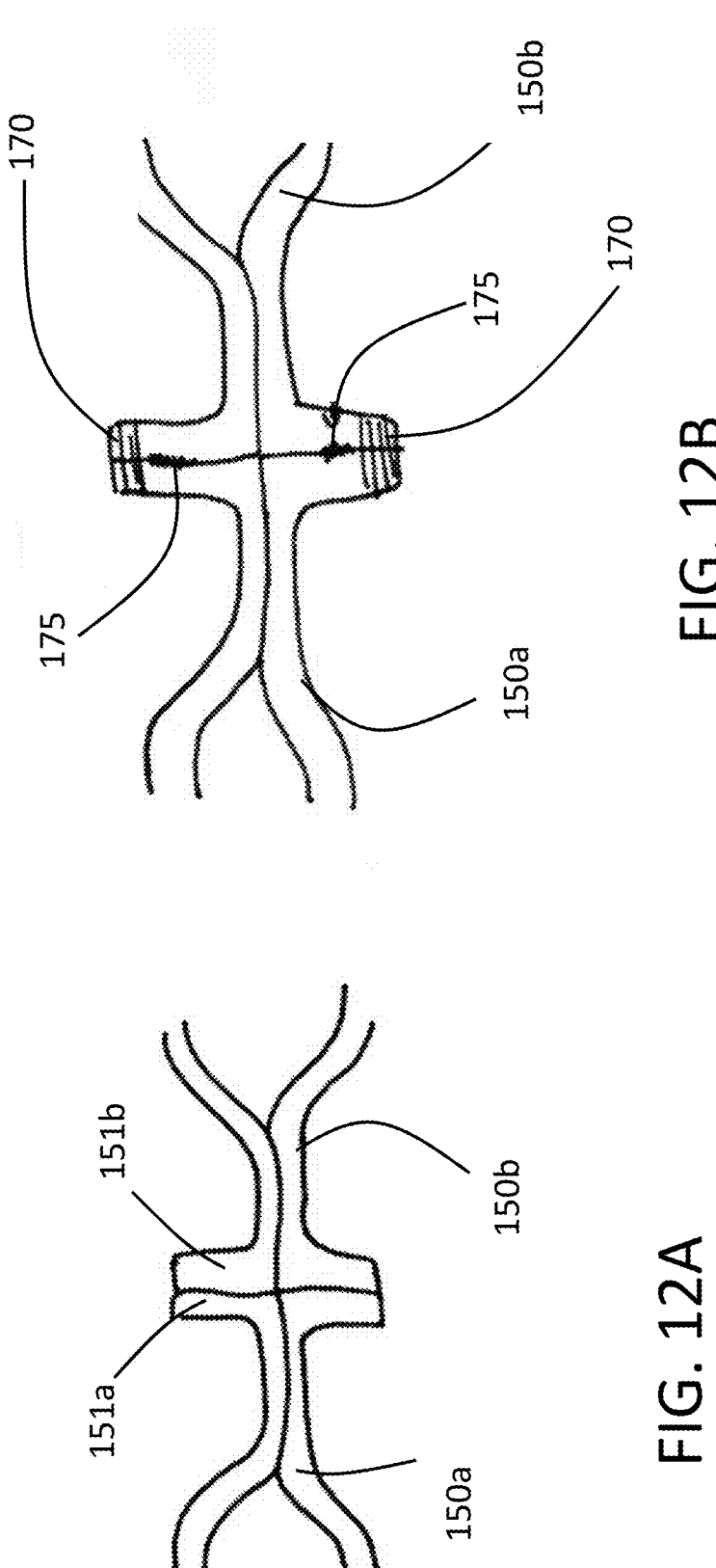
FIG. 12A shows two tubes each with a flange at an end.
FIG. 12B shows the tubes of FIG. 12A after the tubes have been connected using the flanges.

FIG. 12A shows two tubes 150*a*, 150*b* to be connected together via flanges 151*a*, 151*b* formed at their respective ends. In the depicted configuration, the two tubes 150*a*, 150*b* have been brought together using methods previously discussed. In FIG. 12B, the tubes are joined, welded or clamped together at the positions marked 170 such that a seal is present at the positions marked 175. The tubes 150*a*, 150*b* may be heated using any of the methods described previously in order to weld them together. A method for forming the flanges will now be described.

Figure 13A:
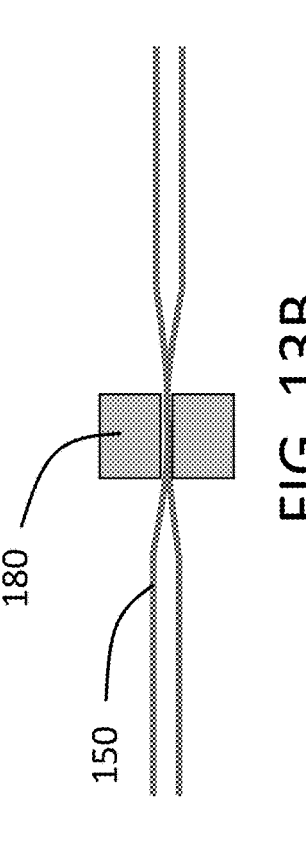
FIGS. 13A to 13D show an apparatus for forming the flanges of FIGS. 12A and 12B.
Figure 13B:
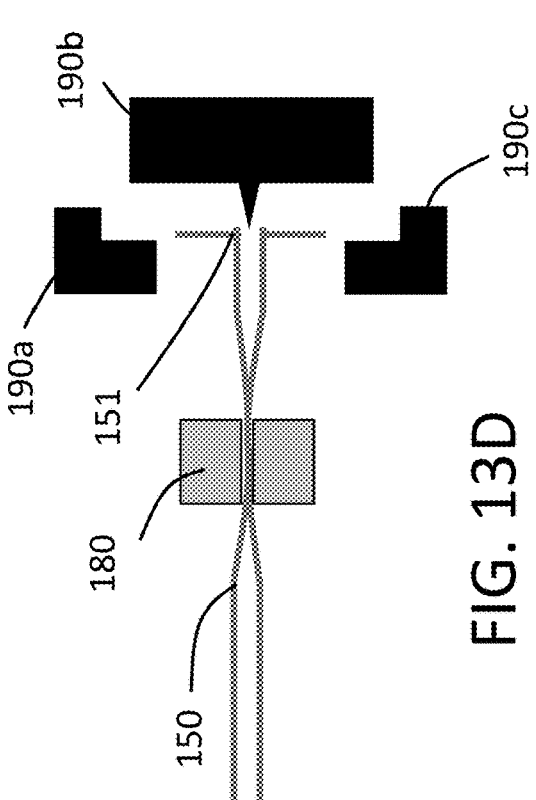
Figure 13C:
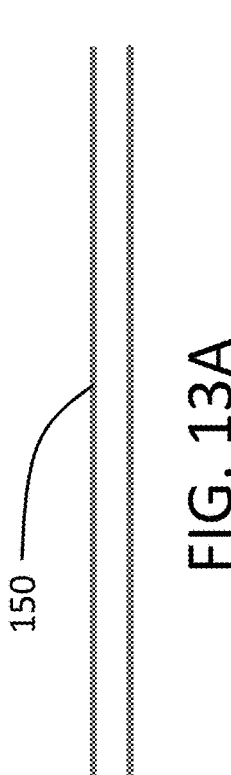
Figure 13D:
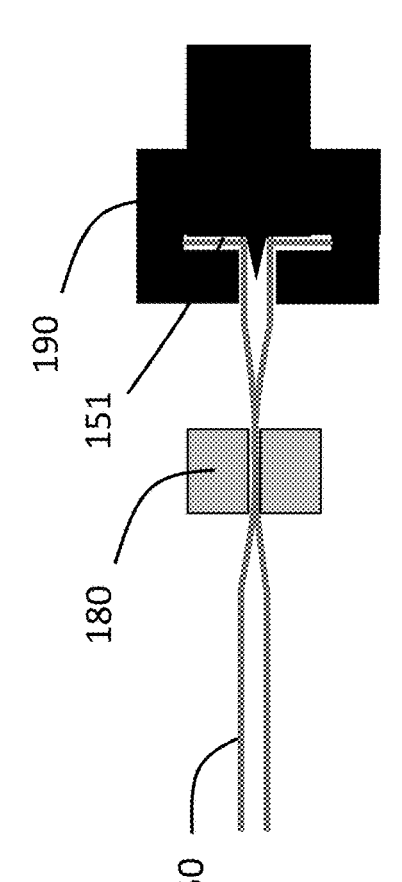

FIG. 13A shows a tube 150. In FIG. 13B, the tube 150 is mechanically pinched using a clamp 180 in order to prevent fluid flow through the tube 150. The pumping unit 30 may pump fluid away from the clamp. In FIG. 13C, the tube 150 is pushed into a heated die 190 to reform the tube 150 into a desired flange 151. In FIG. 13D, the die 190 is allowed to cool, and separated into a plurality of parts 190*a*, 190*b*, 190*c*, in order to free the flange 151 of the tube 150 from the die 190. The die 190 may be sterilised between each flange-forming operation by an autoclave or by heating the die to a high temperature such as a temperature above 400° C.

Figure 14:
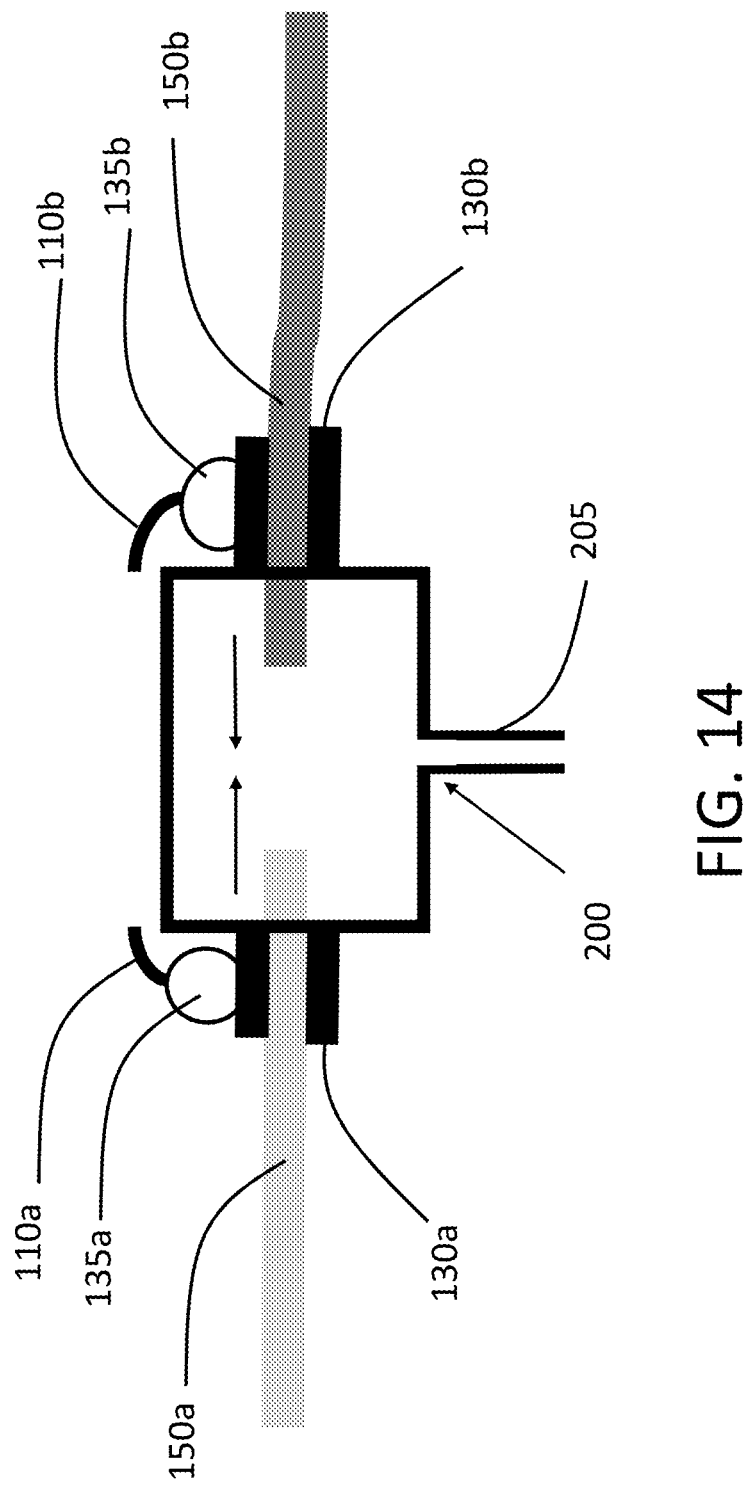
FIG. 14 shows a third embodiment of an apparatus for forming aseptic connections between tubes in the automated bioprocessing system.

FIG. 14 shows another apparatus for forming aseptic welds using steam sterilisation and heat welding. As well as a number of components already described in detail, the apparatus comprises a steam chamber 200 with a steam inlet 205. The tubes 150*a*, 150*b* to be welded together extend into the steam chamber 200 and may be open ended, but are pinched shut upstream such as using clamps or pumps like those already described. Steam is injected into the steam inlet 205, which sterilises the tubes 150*a*, 150*b* and the inside of the steam chamber. The heat from the steam also melts the ends of the tubes 150*a*, 150*b* that extend into the steam chamber 200. Then, the precession wheels 135*a*, 135*b* rotate to press and weld the ends of the tubes 150*a*, 150*b* together. Once welded, the tubes 150*a*, 150*b* can be unpinched upstream and the pumping unit 30 can pump fluid through the connected tubes 150*a*, 150*b*.

Figure 15B:
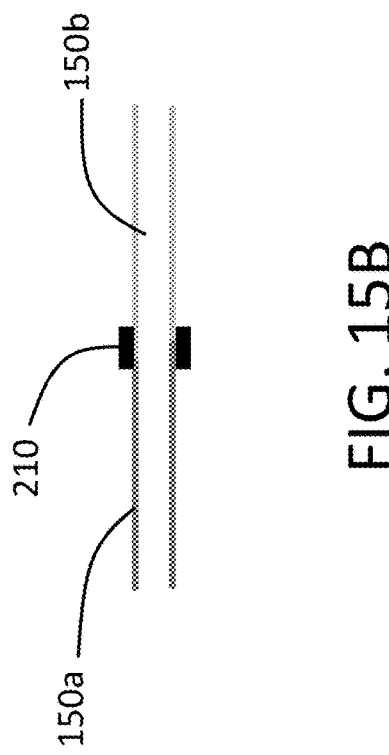
FIGS. 15A and 15B show a fourth embodiment of an apparatus for forming aseptic connections between tubes in the automated bioprocessing system, at two steps along the connection process.
Figure 15A:
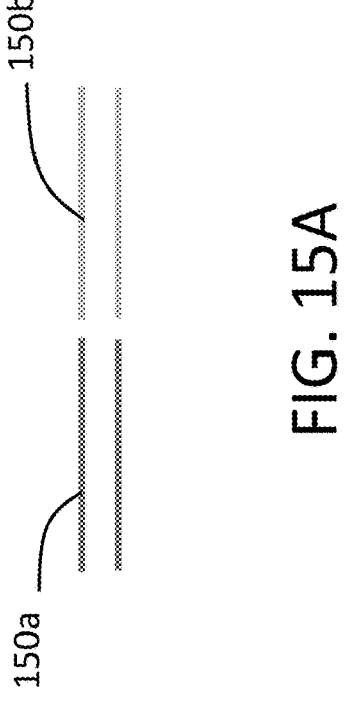

FIG. 15A shows two tubes 150*a*, 150*b* to be connected together with an alternative method for forming aseptic welds, in which material is added to the tubes 150*a*, 150*b*. The tubes 150*a*, 150*b* may be cut using any above method, and may be pinched upstream to prevent fluid flow. In FIG. 15B, material 210 at a high temperature is injected around the ends of the two tubes 150*a*, 150*b*, once the tubes 150*a*, 150*b* are brought together. The material 210 is applied using an injection mould (overmould) around the outside of the joint between the two tubes 150*a*, 150*b*. This may be performed using UV cured glue, or a heat shrink adhesive.

Figure 16B:
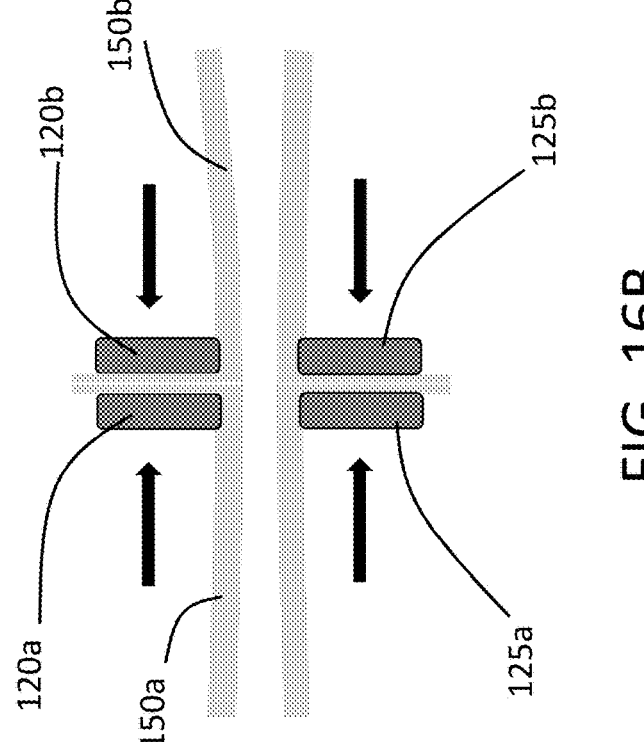
FIGS. 16A and 16B show a fifth embodiment of an apparatus for forming aseptic connections between tubes with flanges in the automated bioprocessing system, at two steps along the connection process.
Figure 16A:
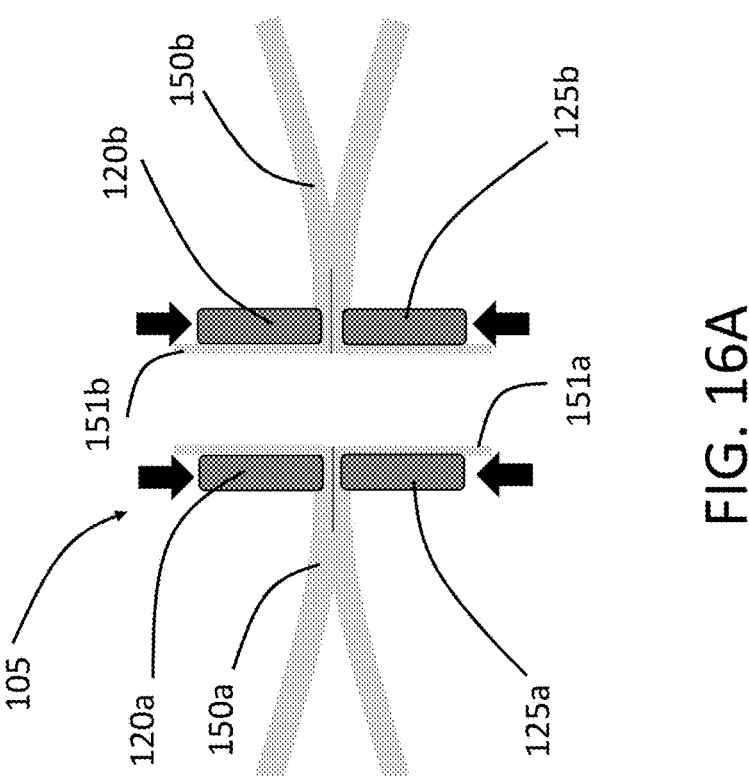

FIG. 16A shows two tubes 150*a*, 150*b* with flanges 151*a*, 151*b* like those described in relation to FIGS. 12A, 12B and 13A to 13D. Here the tubes 150*a*, 150*b*, can be aseptically clamped together using the clamping unit 105 without the need for heat sources or welding. Heat may be used to sterilise the flanges 151*a*, 151*b*, or to provide additional welding. In FIG. 16A, the first parts 120*a*, 125*a* of the clamping unit 105 clamp the first tube 150*a* to pinch the tube 150*a* adjacent to the flange 151*a*. Similarly, the second parts 120*b*, 125*b* of the clamping unit 105 clamp the second tube 150*b* to pinch the tube 150*b* adjacent to the flange 151*b*. In FIG. 16B, the first parts 120*a*, 125*a* of the clamping unit 105 are moved towards the second parts 120*b*, 125*b* of the clamping unit 105 to pinch the flanges 151*a*, 151*b* of the respective tubes 150*a*, 150*b* together. Then, both parts 120*a*, 120*b* of the first jaw 120 can move apart from both parts 125*a*, 125*b* of the second jaw 125, thereby unpinching the tubes 150*a*, 150*b* and providing a continuous tube 150 through which fluid can be pumped by the pumping unit 30.

Figure 17A:
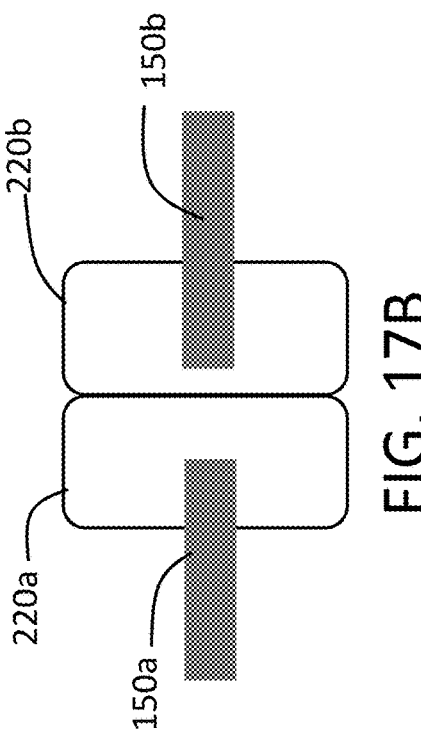
FIGS. 17A to 17D show a sixth embodiment of an apparatus for forming aseptic connections between tubes in the automated bioprocessing system, at various steps along the connection process.
Figure 17B:
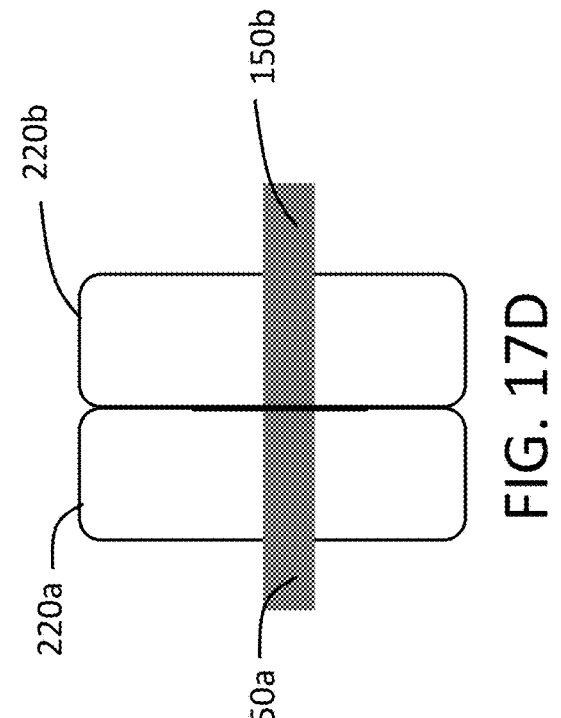
Figure 17C:
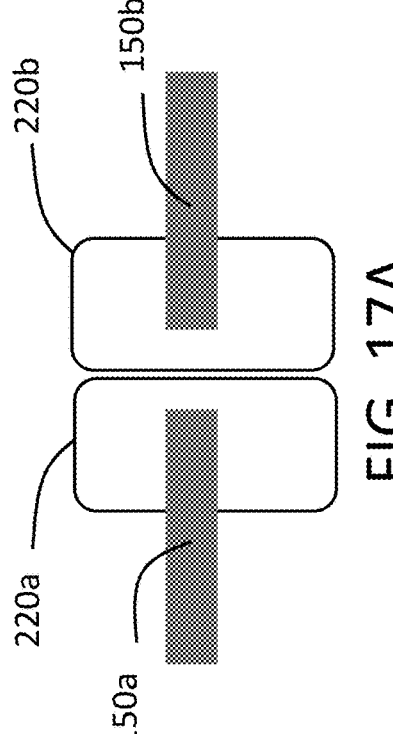
Figure 17D:
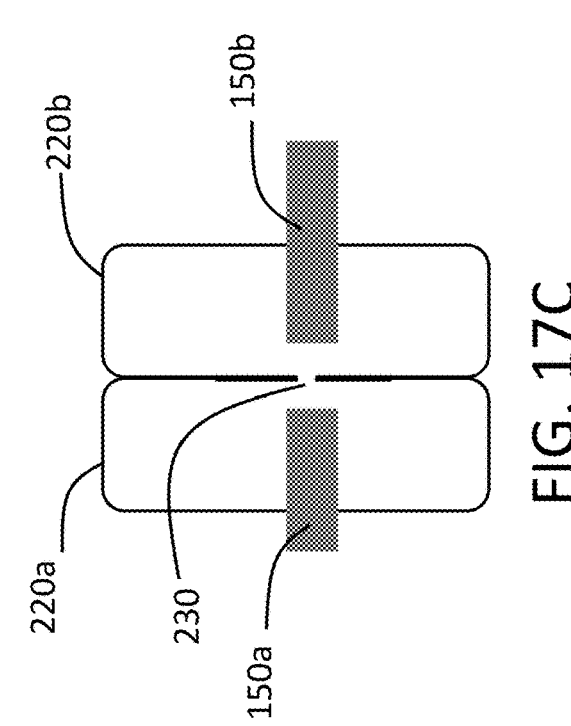
Figure 17F:
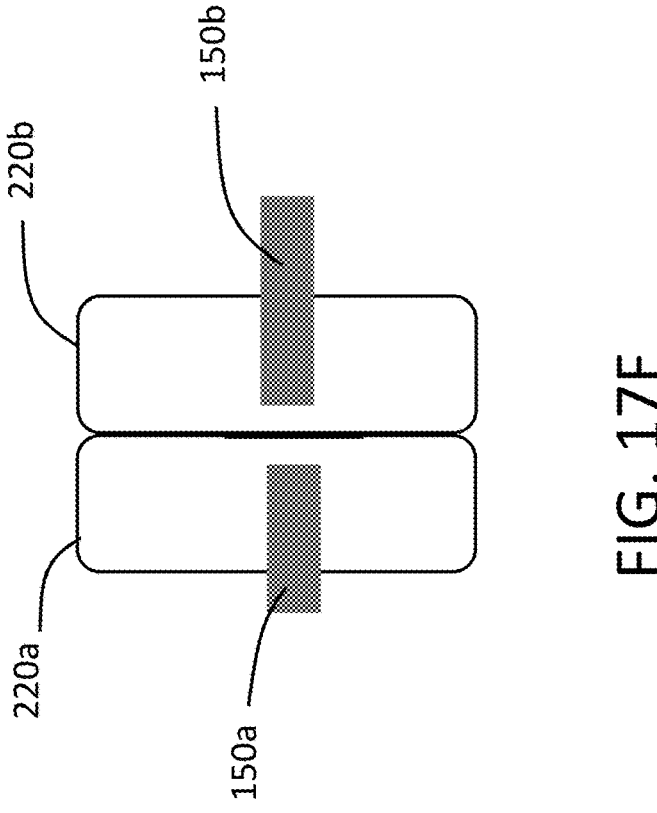
FIGS. 17E and 17F show the sixth embodiment of the apparatus for forming aseptic connections between tubes in the automated bioprocessing system, at two steps along the disconnection process.
Figure 17E:
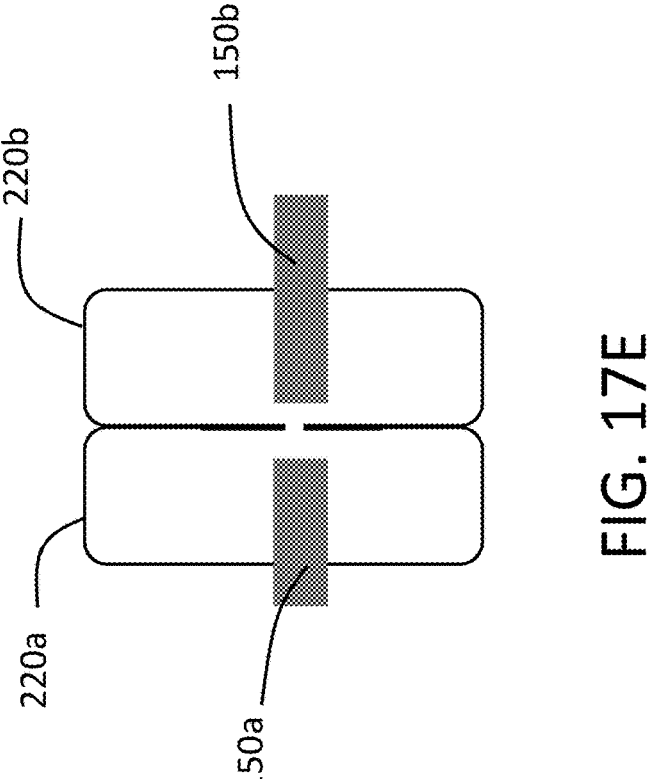

FIG. 17A shows two tubes 150*a*, 150*b* to be connected together, where the end of each tube 150*a*, 150*b* is located in a respective bag 220*a*, 220*b*. In FIG. 17B, the bags 220*a*, 220*b* are brought together, and heat is applied to weld and melt the bags 220*a*, 220*b* together. The heat can be applied using any of the methods previously described. In FIG. 17C, a laser is used to cut a slot 230 linking the two bags 220*a*, 220*b*, and in FIG. 17D, the tubes 150*a*, 150*b* within the bags 220*a*, 220*b* are brought together to form a connection. The laser may also be used here to weld the tubes 150*a*, 150*b* together. In FIG. 17E, the reverse process occurs, where the tubes 150*a*, 150*b* are moved apart after the tubes 150*a*, 150*b* are disconnected, and in FIG. 17F, the slot 230 between bags 220*a*, 220*b* is welded together again. Now, the two bags 220*a*, 220*b* can be disconnected.

Figure 18B:
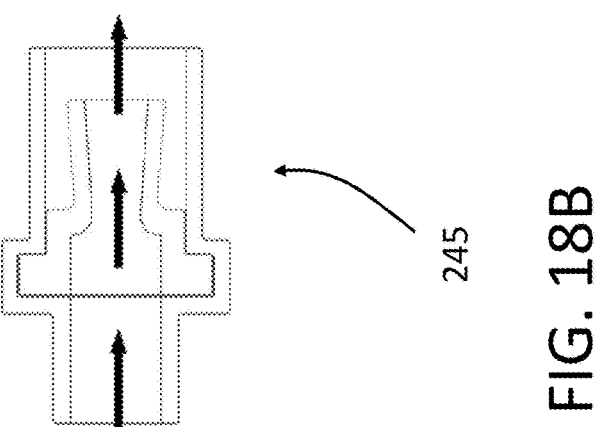
FIG. 18B shows the connector used to form the connection of FIG. 18A.
Figure 18A:
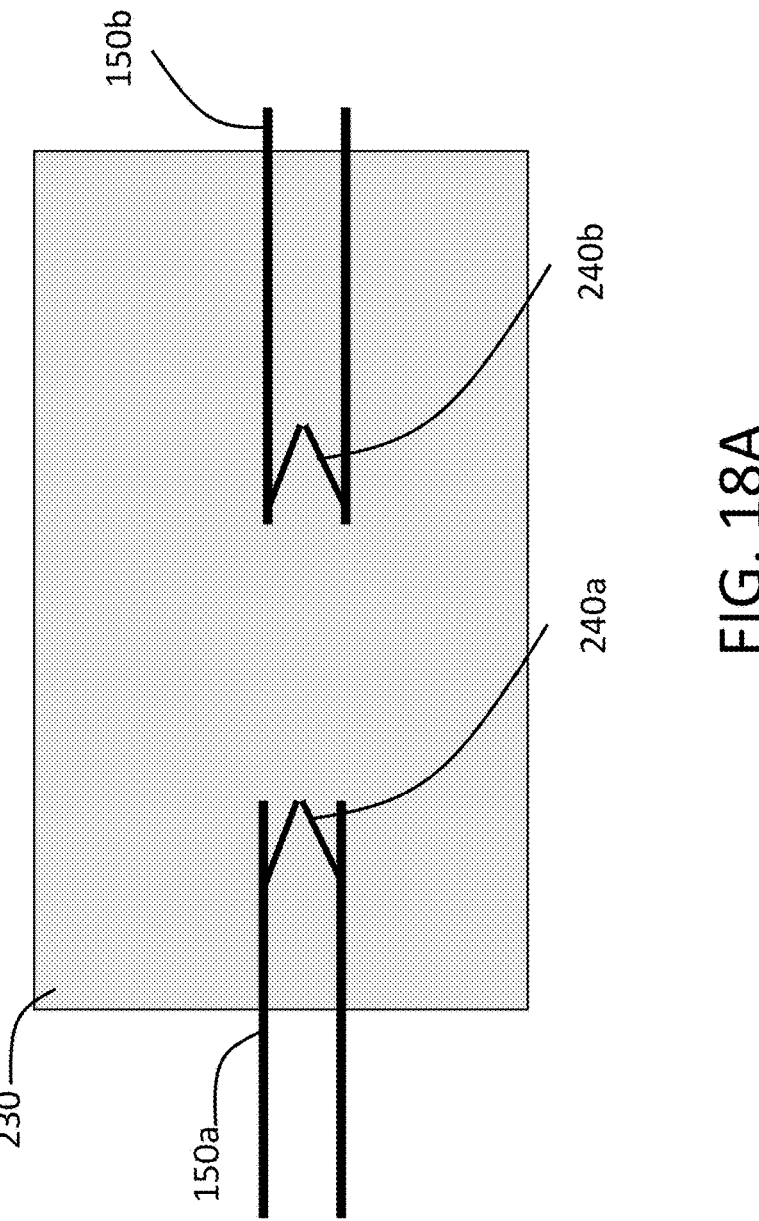
FIG. 18A shows a seventh embodiment of an apparatus for forming aseptic connections between tubes in the automated bioprocessing system.

FIG. 18A shows an alternative apparatus for making aseptic connections, comprising a sterilisation box 230. The sterilisation box 230 provides a locally aseptic environment which means that the tubes 150*a*, 150*b* may be connected together using standard connections such as the connector 245 shown in FIG. 18B. The tubes 150*a*, 150*b* each have a respective duckbill valve 240*a*, 240*b* that are closed unless fluid is pumped by the pumping unit 30. To operate this apparatus, the tubes 150*a*, 150*b* are inserted into the sterilisation box 230, which sterilises the tubes 150*a*, 150*b*. Then the tubes 150*a*, 150*b* are connected together using the connector 245 immediately after the sterilisation is performed by the sterilisation box 230. The sterilisation box 230 may be an autoclave box that sterilises the tubes 150*a*, 150*b* using steam. Alternatively, the sterilisation box 230 may use other methods such as Ethanol sterilisation (EtOH) Ethylene Oxide sterilisation (EtO), gamma radiation, UV sterilisation, electron beam sterilisation, or any combination of the above.

Figure 19:
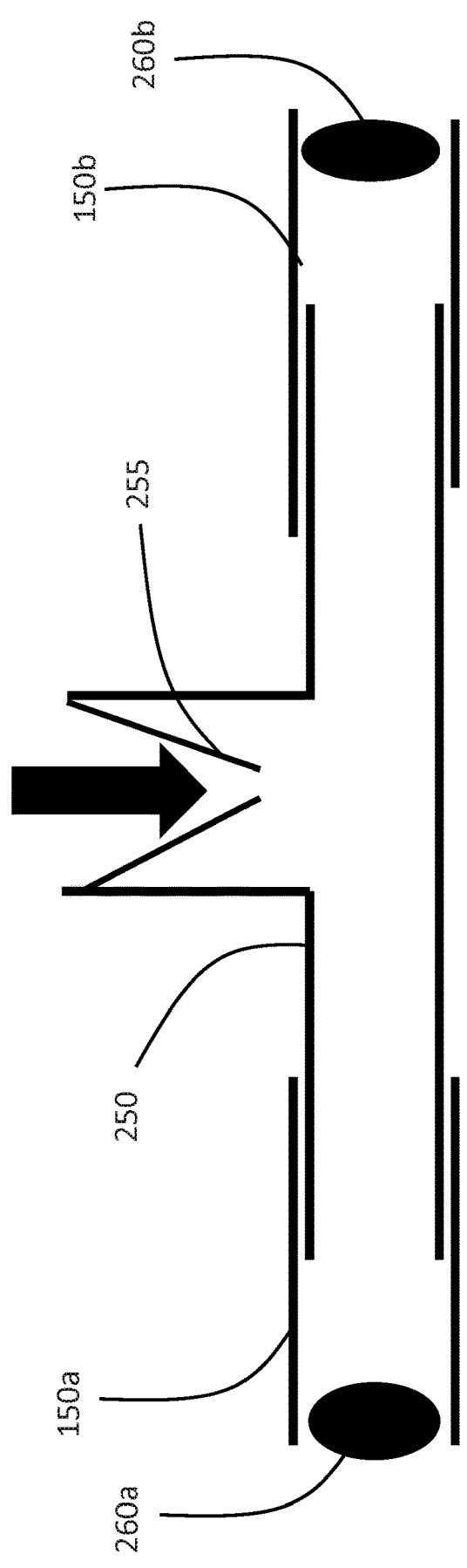
FIG. 19 shows an eighth embodiment of an apparatus for forming aseptic connections between tubes in the automated bioprocessing system.

FIG. 19 depicts an alternative apparatus for making aseptic connections, comprising a "T"-piece connector 250 with a valved inlet 255 for steam. The tubes 150*a*, 150*b* to be connected together each have a valve 260*a*, 260*b*, which remains closed unless fluid is pumped by the pumping unit 30. After the tubes 150*a*, 150*b* are connected to the T-piece connector 250 while the valves 260*a*, 260*b* are closed, steam is pumped through the inlet 255 to sterilise the surfaces before the valves 260*a*, 260*b* are opened to allow fluid to flow through the tubes 150*a*, 150*b*.

Figure 20:
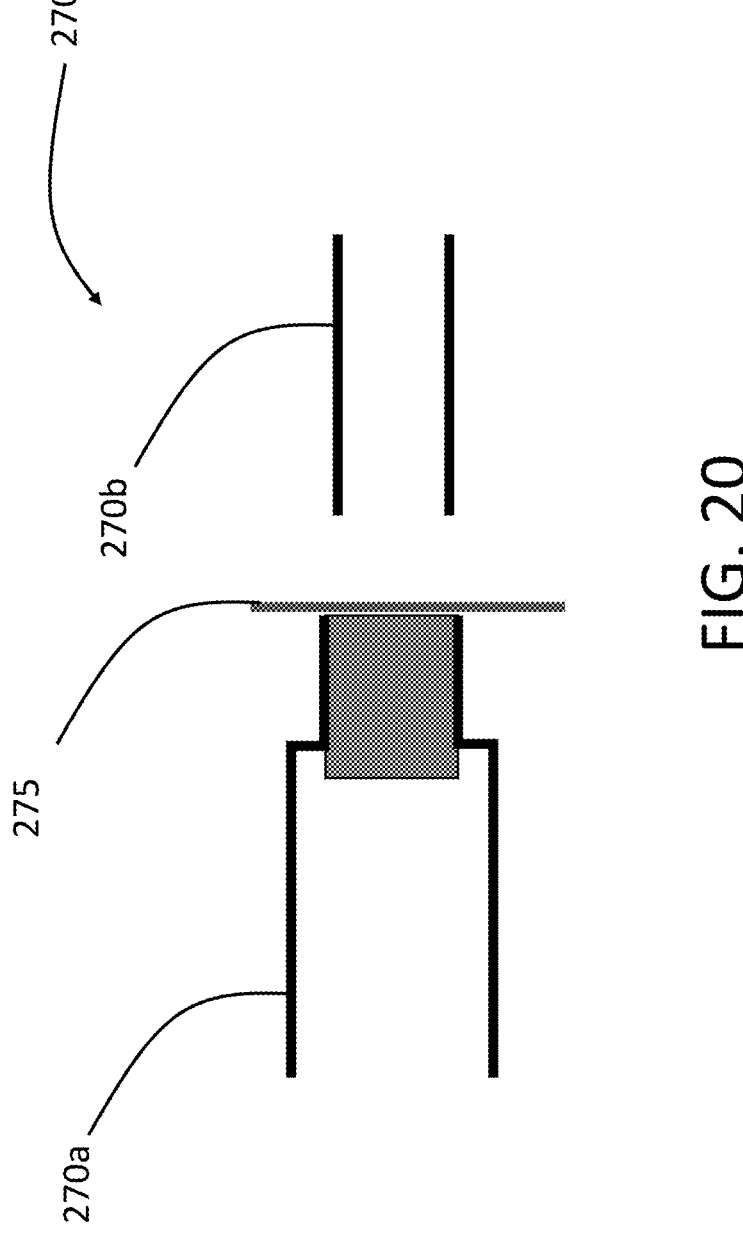
FIG. 20 shows a ninth embodiment of an apparatus for forming aseptic connections between tubes in the automated bioprocessing system.

FIG. 20 shows a needle free connector 270 with a first part 270*a* and a second part 270*b*, than can be fixed together to form a reversible connection. Prior to attachment, the first part 270*a* and the second part 270*b* of the needle free connector are sterilised such as by using an autoclave or a laser, or by using a hot blade 275 as shown here.

Figure 21:
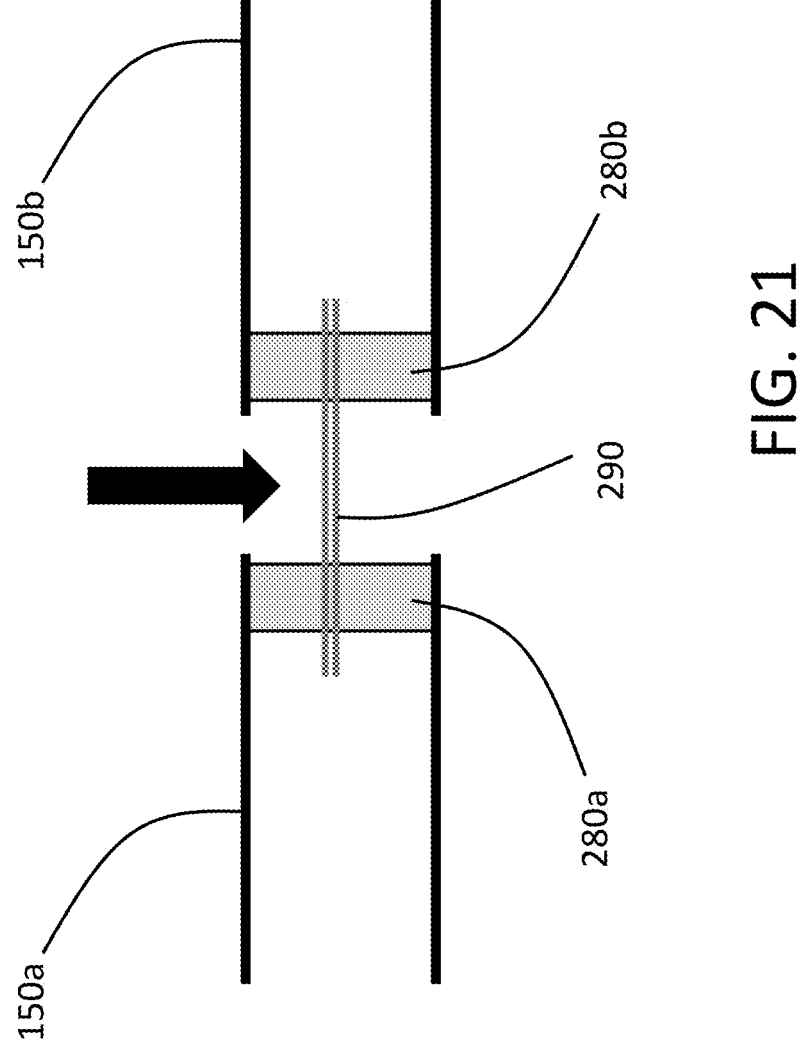
FIG. 21 shows a tenth embodiment of an apparatus for forming aseptic connections between tubes in the automated bioprocessing system.

FIG. 21 shows two tubes 150*a*, 150*b* each with a respective septum seal 280*a*, 280*b*. The tubes 150*a*, 150*b* can be connected together with a needle 290 which is first heated for sterilisation, and then inserted through the septum seals 280*a*, 280*b*.

Figure 22A:
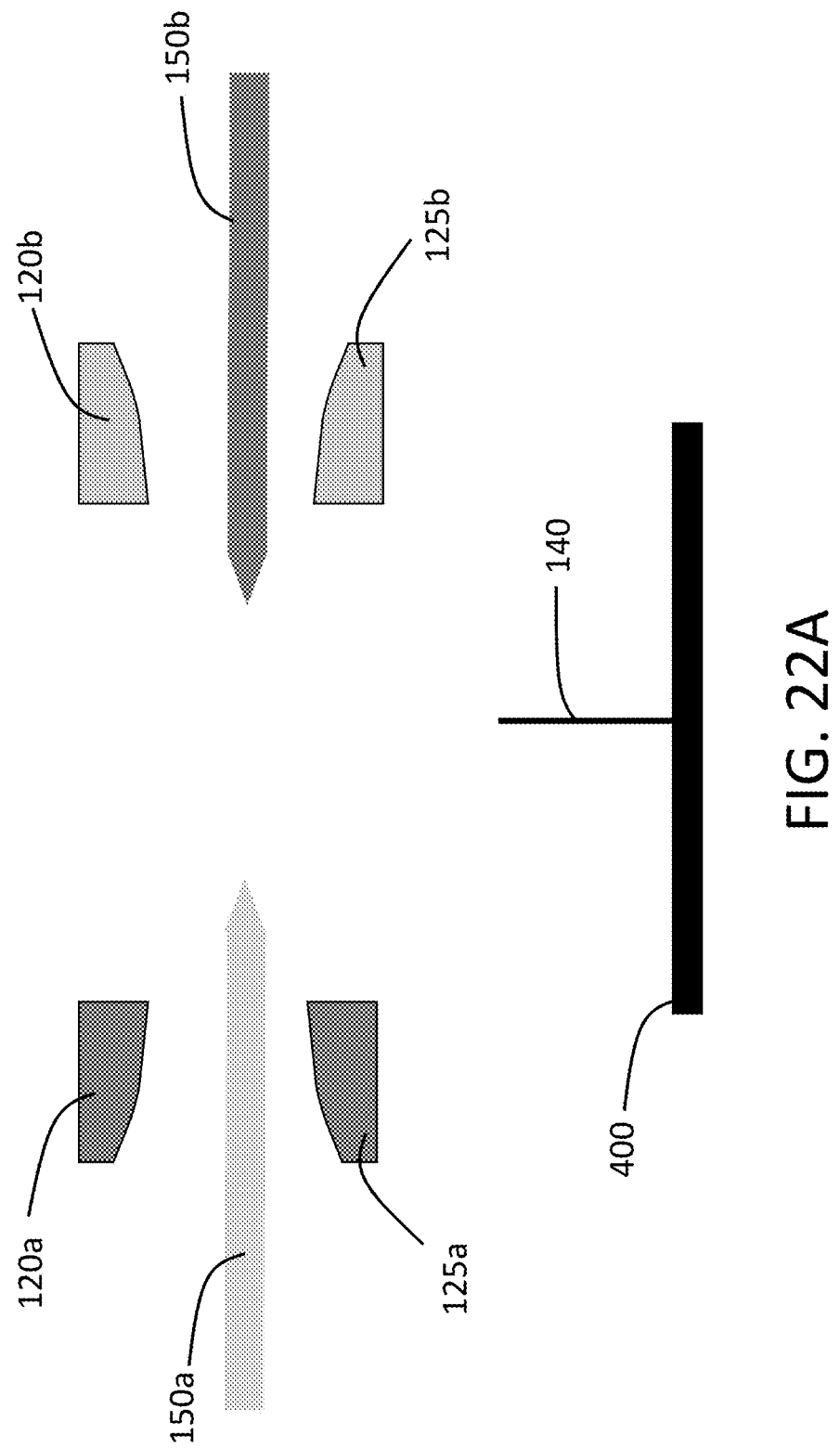
FIGS. 22A to 22G show an eleventh embodiment of an apparatus for forming aseptic connections between tubes in the automated bioprocessing system.
Figure 22B:
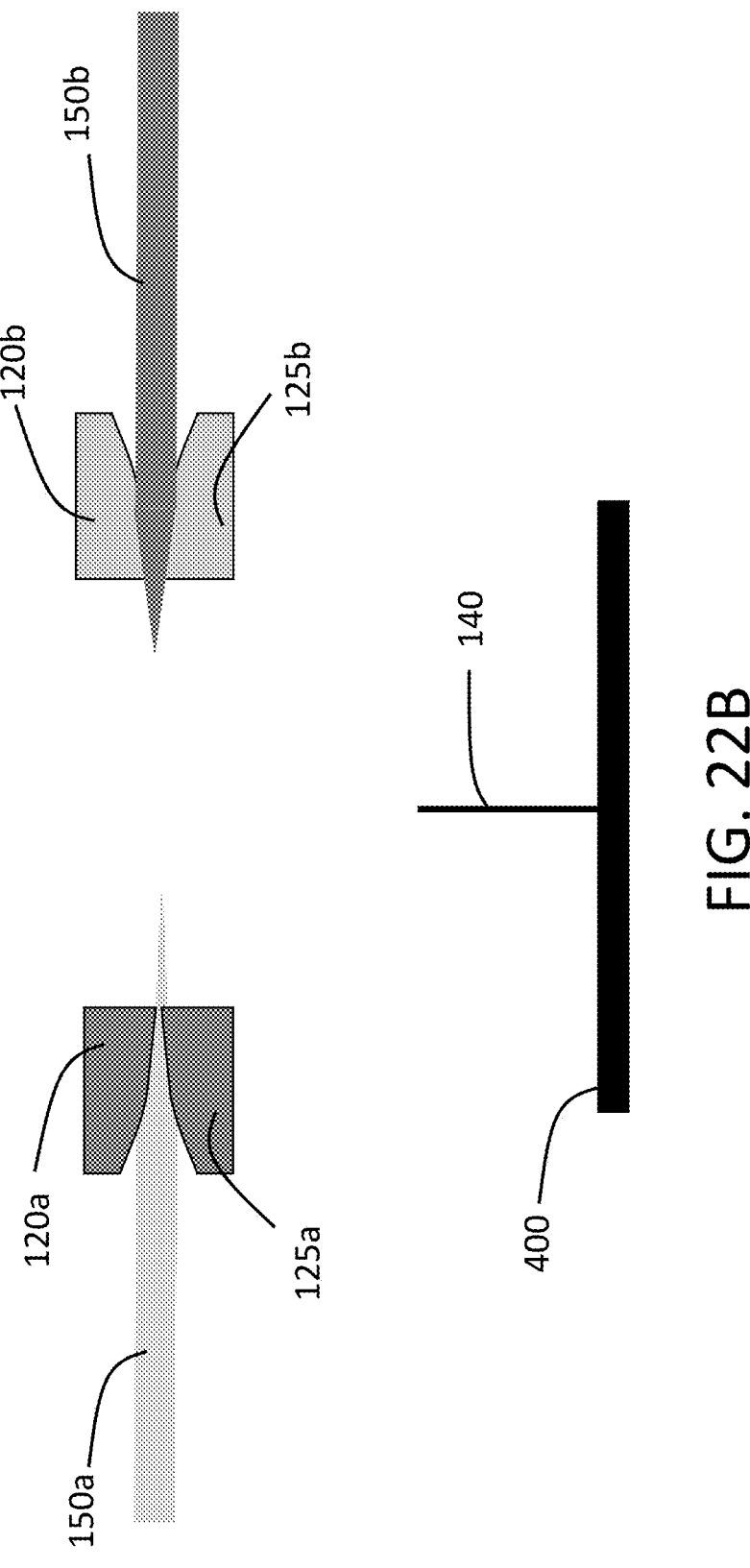
Figure 22C:
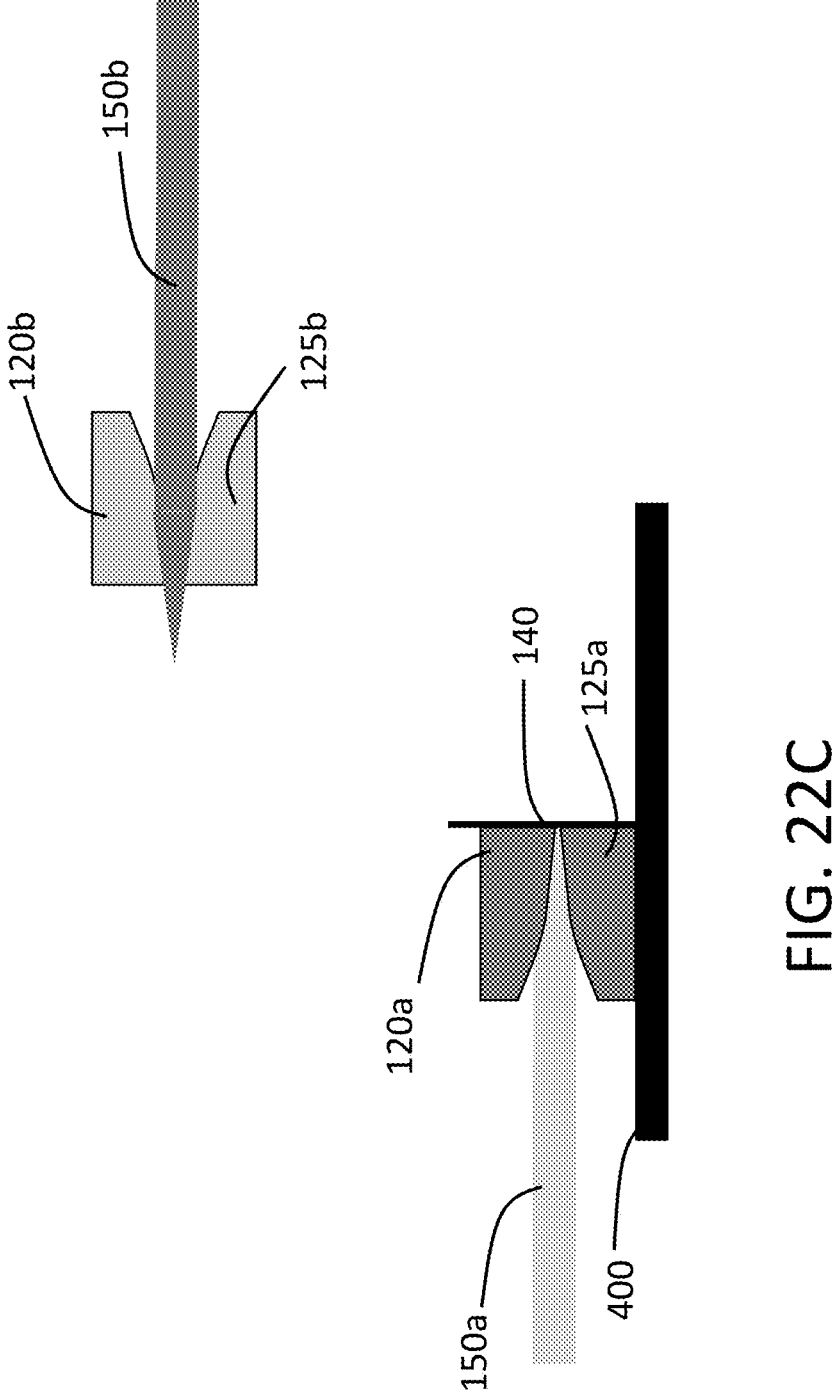
Figure 22D:
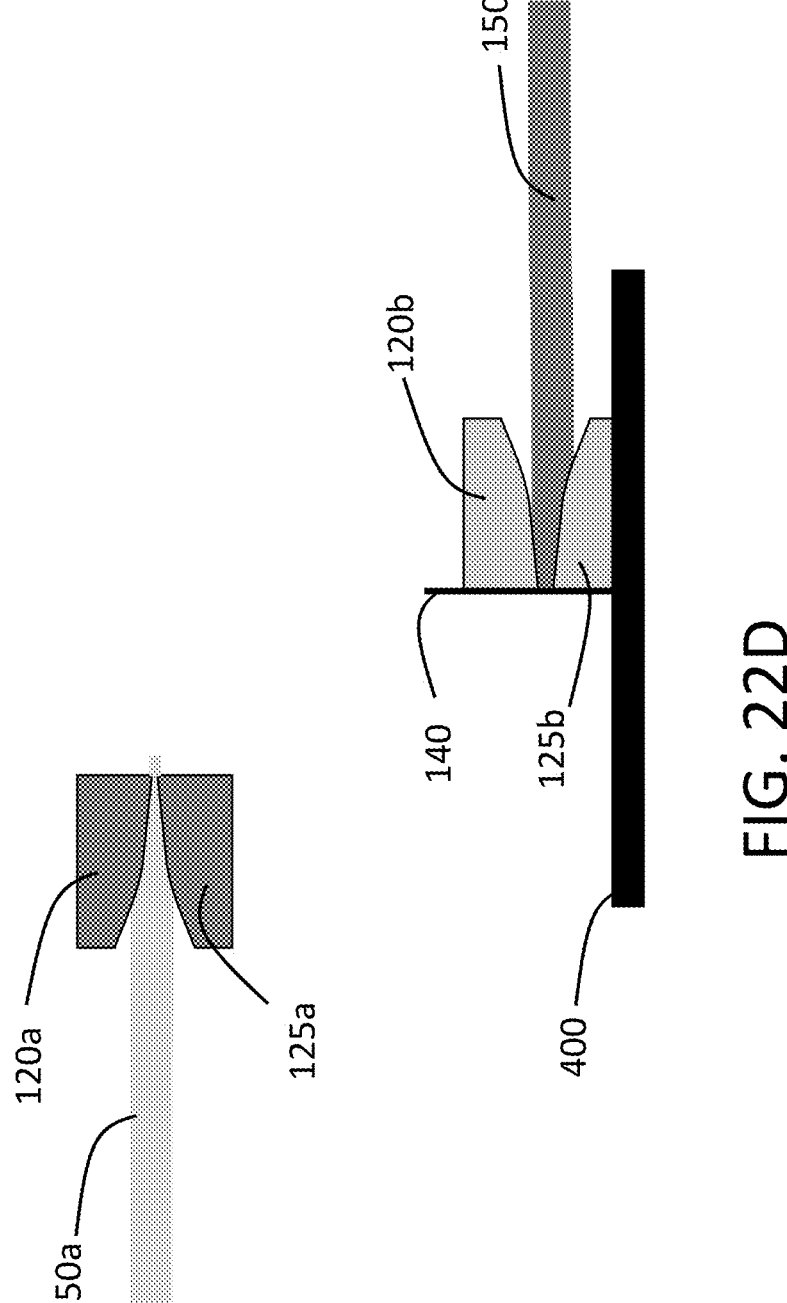
Figure 22E:
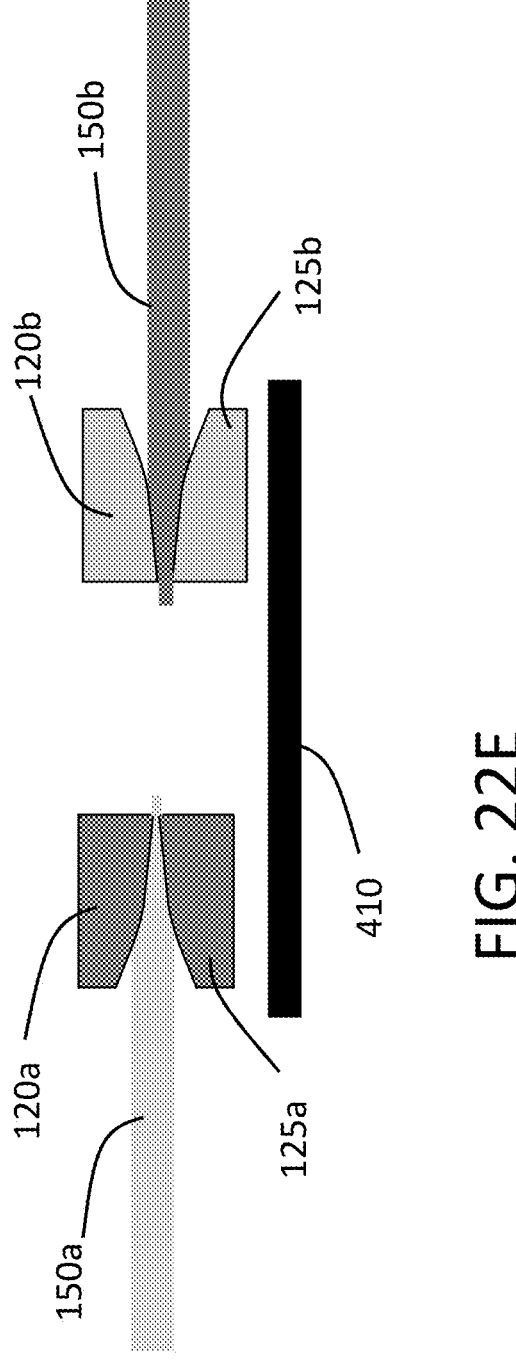
Figure 22F:
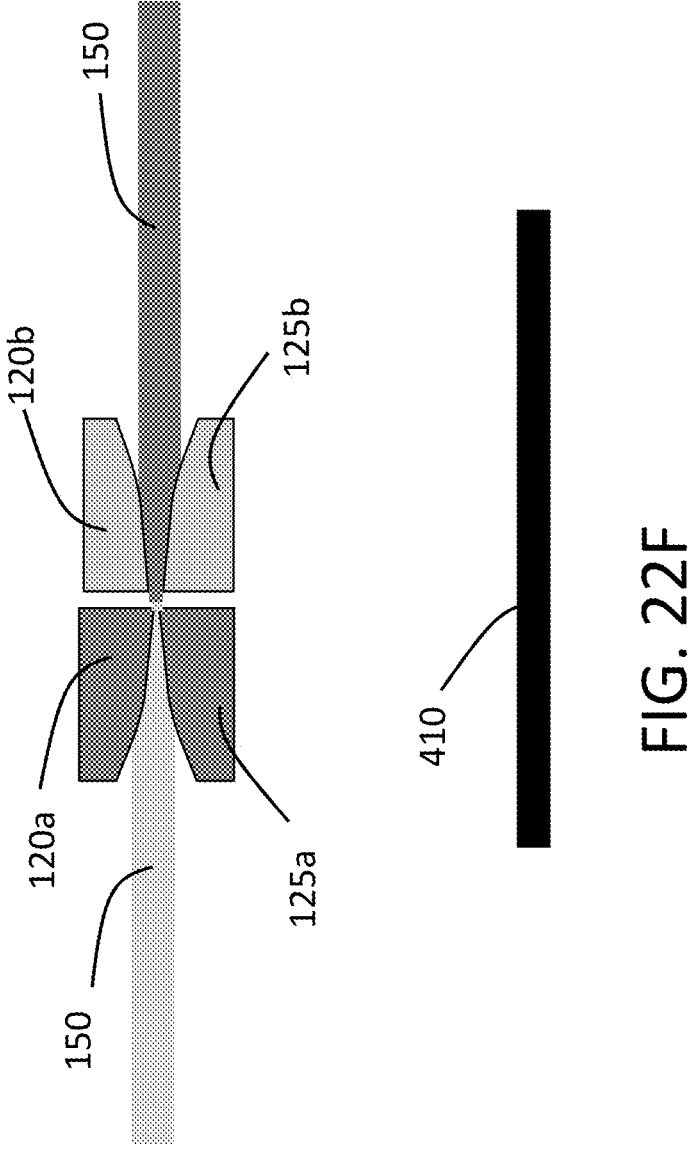
Figure 22G:
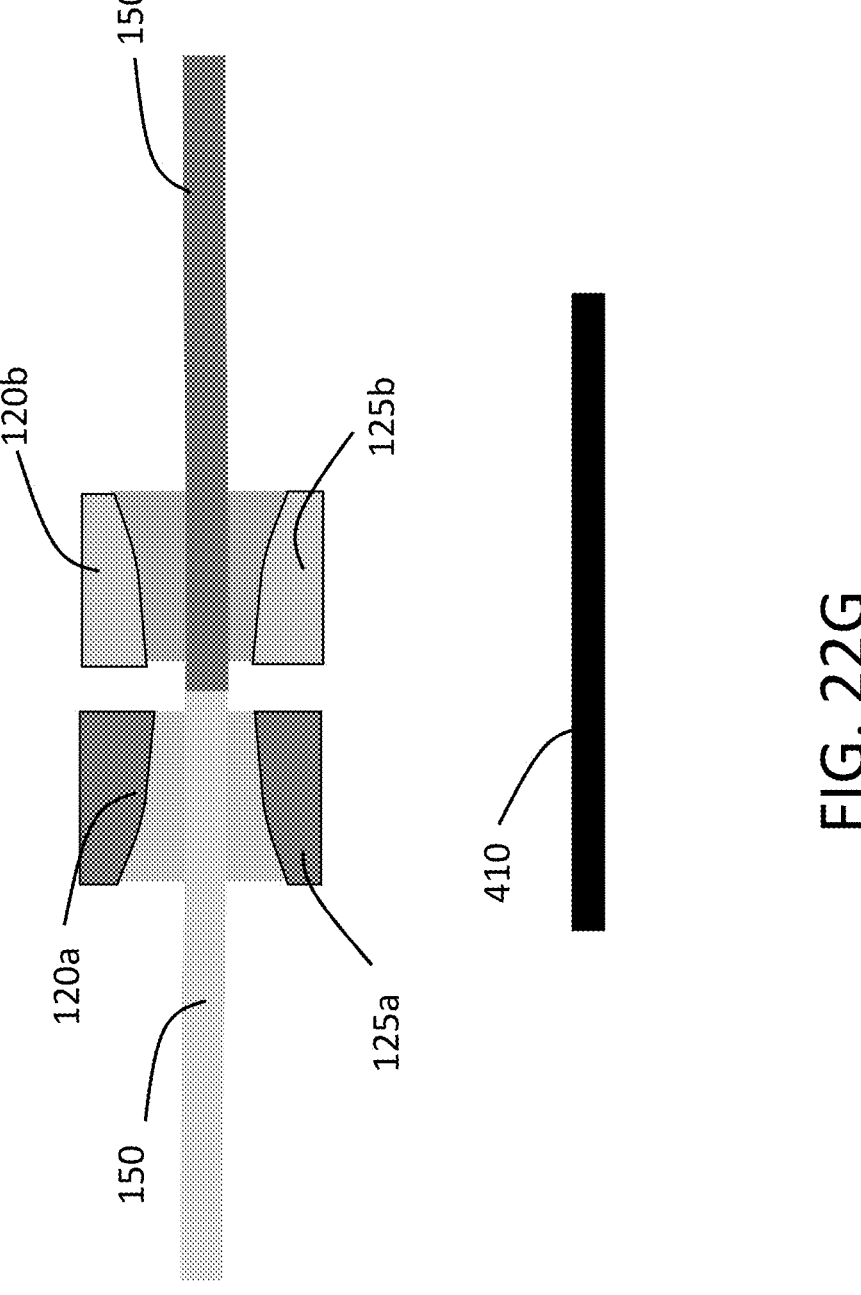

FIG. 22A depicts an alternative apparatus for making aseptic connections, where the blade 140 is attached to a surface 400. The surface 400 may be located at one of the processing stations 20. The apparatus has a first jaw 120 split into a first and second part 120*a*, 120*b*, and a second jaw 125 divided into a first and second part 125*a*, 125*b*. The first parts 120*a*, 125*a* of the jaws are movable independently to the second parts 120*b*, 125*b* of the jaws, such as by use of one or more robotic arms 3 on the robotic device 2. In FIG. 22B, the first tube 150*a* is pinched by the first parts 120*a*, 125*a* of the jaws, and the second tube 150*b* is pinched by the second parts 120*b*, 125*b* of the jaws. In FIG. 22C, the first tube 150*a* is cut by moving the first parts 120*a*, 125*a* of the jaws to the blade 140 on the surface 400. In FIG. 22D, the second tube 150*b* is cut by moving the second parts 120*b*, 125*b* of the jaws to the blade 140 on the surface 400. In FIG. 22E, the tubes 150*a*, 150*b* are moved to a heat source 410, which may be located at a separate processing station 20 to the blade 140 or may be located at the same processing station 20 to the blade 140. The heat source 410 melts the ends of the tubes 150*a*, 150*b* that were cut by the blade 140. In FIG. 22F, the first parts 120*a*, 125*a* and the second parts 120*b*, 125*b* of the jaws are moved together to bring into contact the ends of the tubes 150*a*, 150*b* that were cut by the blade 140, thereby welding the tubes 150*a*, 150*b* together to form a single tube 150. In FIG. 22G, the tube 150 is released by moving the first and second parts 120*a*, 120*b* of the first jaw 120 away from the first and second parts 125*a*, 125*b* of the second jaw 125.

Figure 23A:
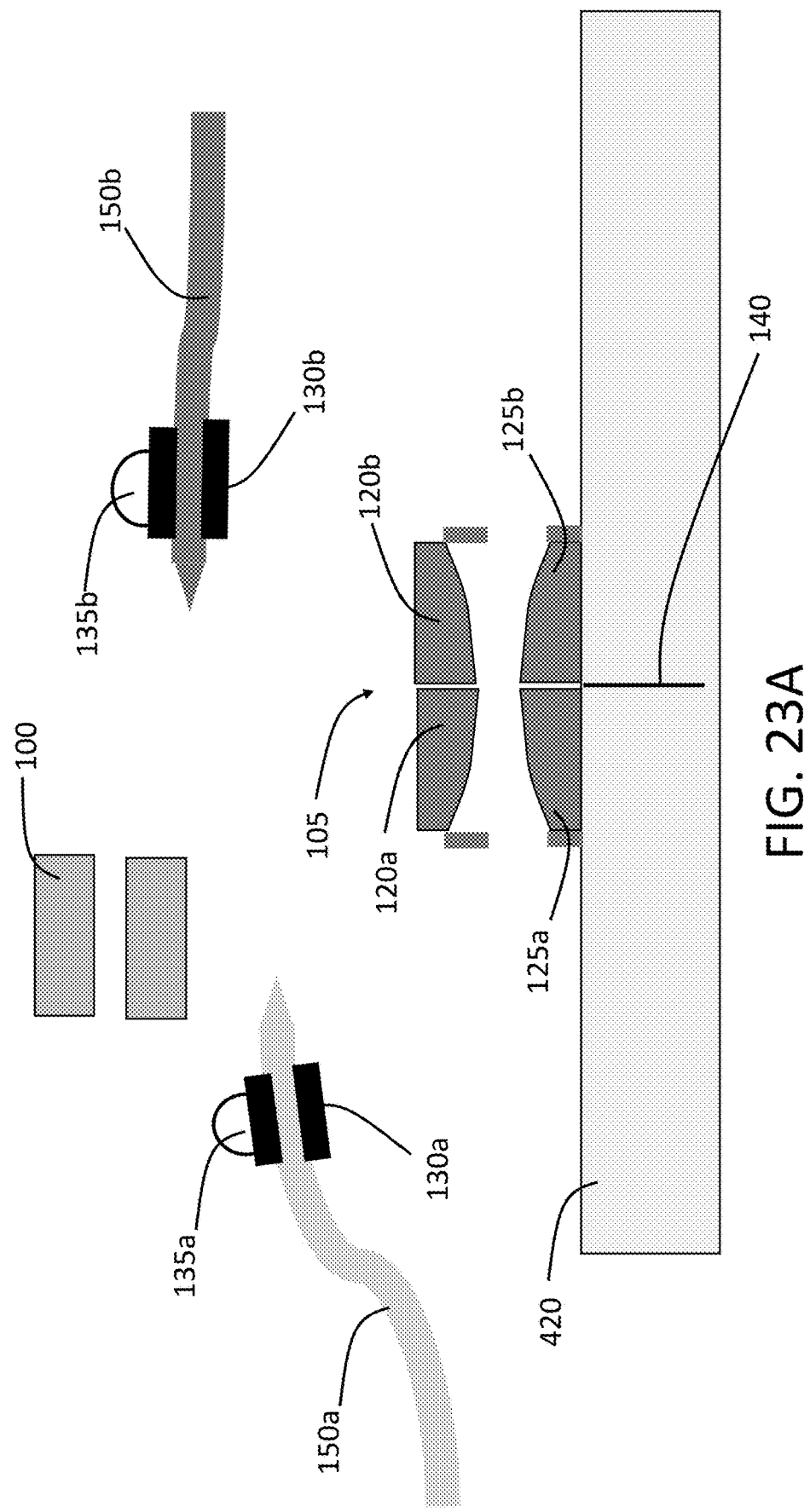
FIGS. 23A to 23H show a twelfth embodiment of an apparatus for forming aseptic connections between tubes in the automated bioprocessing system.
Figure 23B:
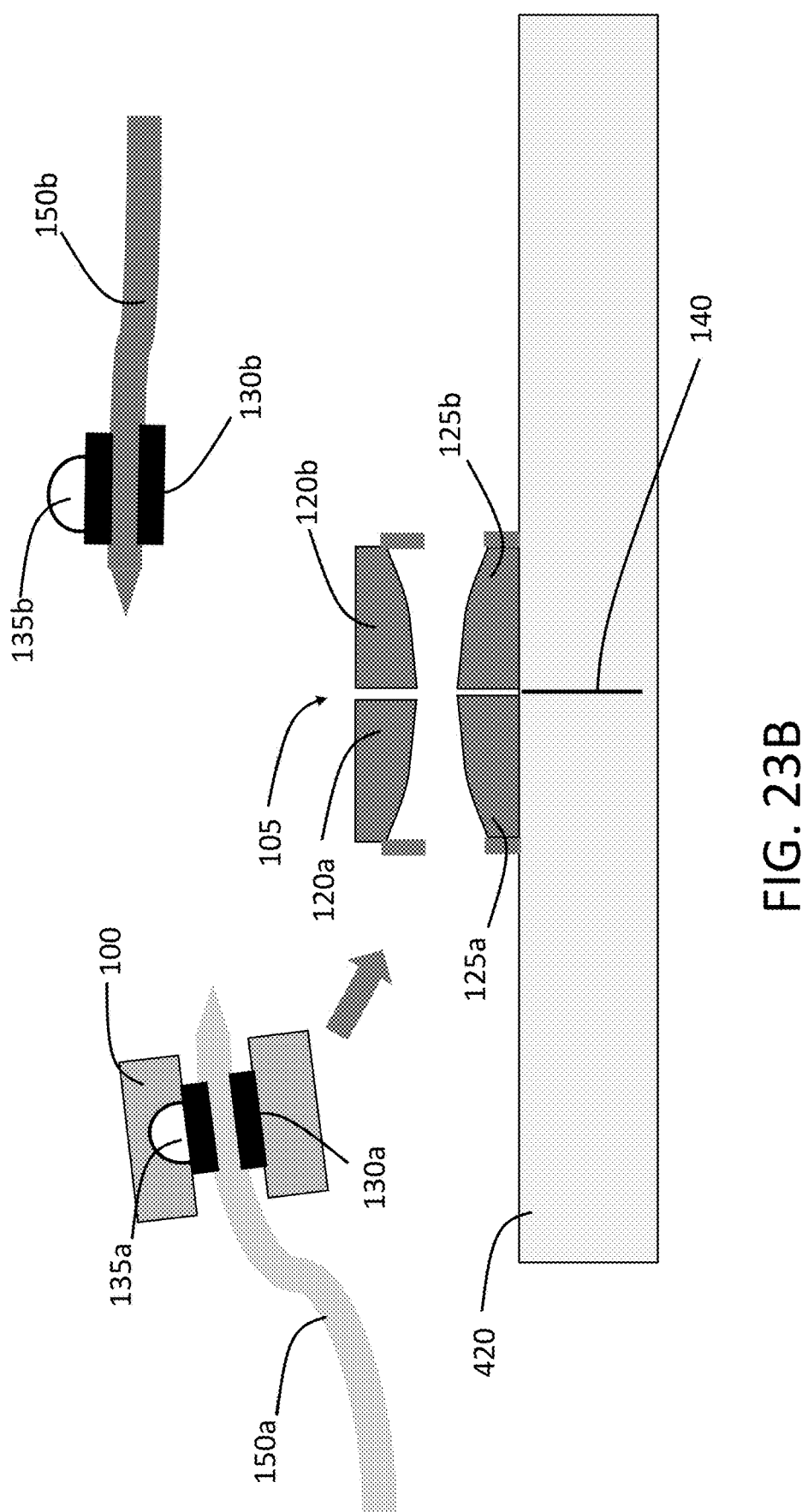
Figure 23C:
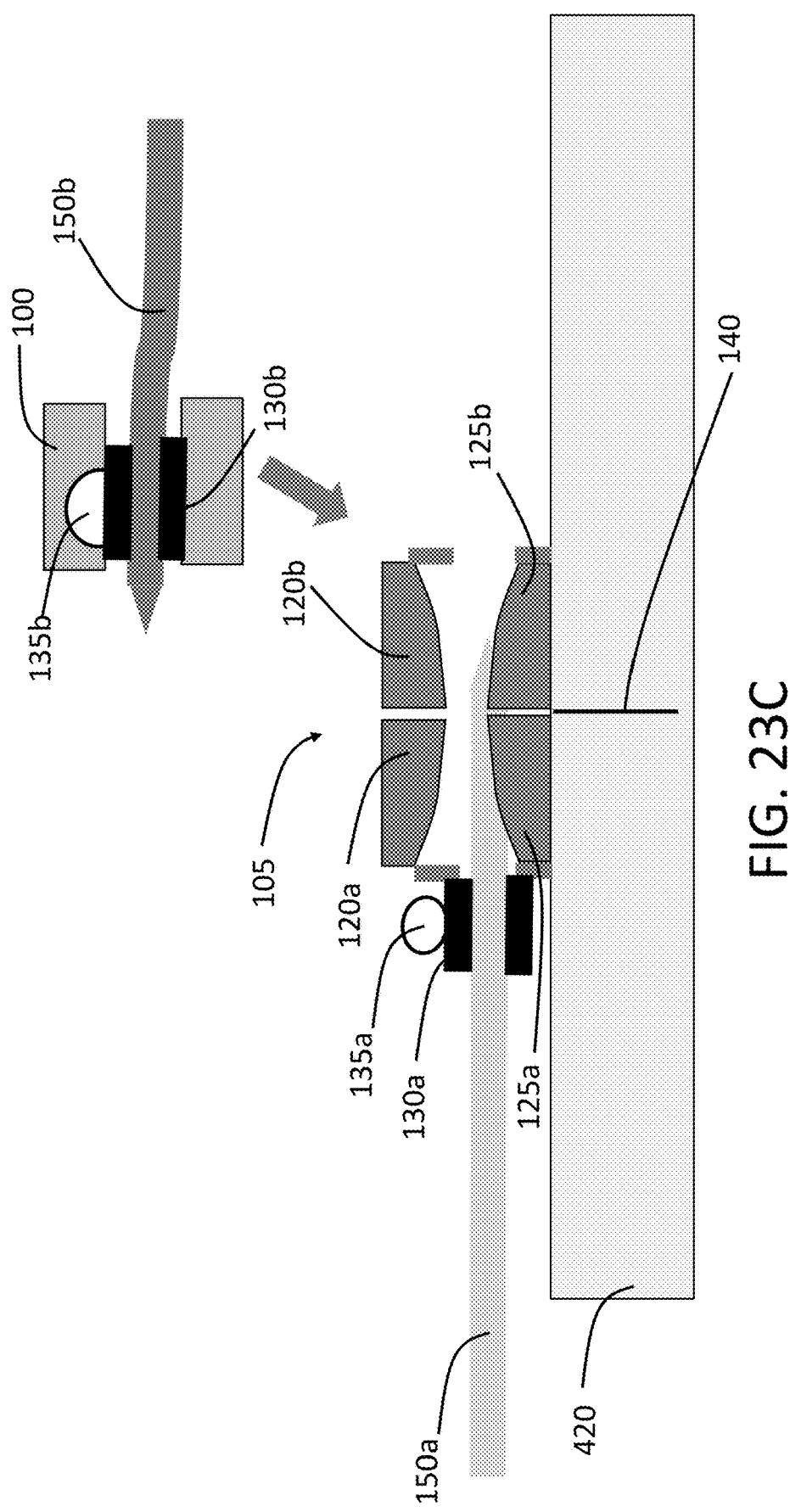

FIG. 23A shows an alternative apparatus for making aseptic connections. The apparatus is similar to the one shown in FIGS. 8A to 8L, except that the clamping unit 105 is attached to a surface 420, such as a surface at one of the processing stations 20. The apparatus also has an end effector 100 for manipulating the tubes 150*a*, 150*b* via the holders 130*a*, 130*b*. In FIG. 23B, the end effector 100 moves the first tube 150*a* into the clamping unit 105, and in FIG. 23C, the end effector 100 moves the second tube 150*b* into the clamping unit 105.

Figure 23D:
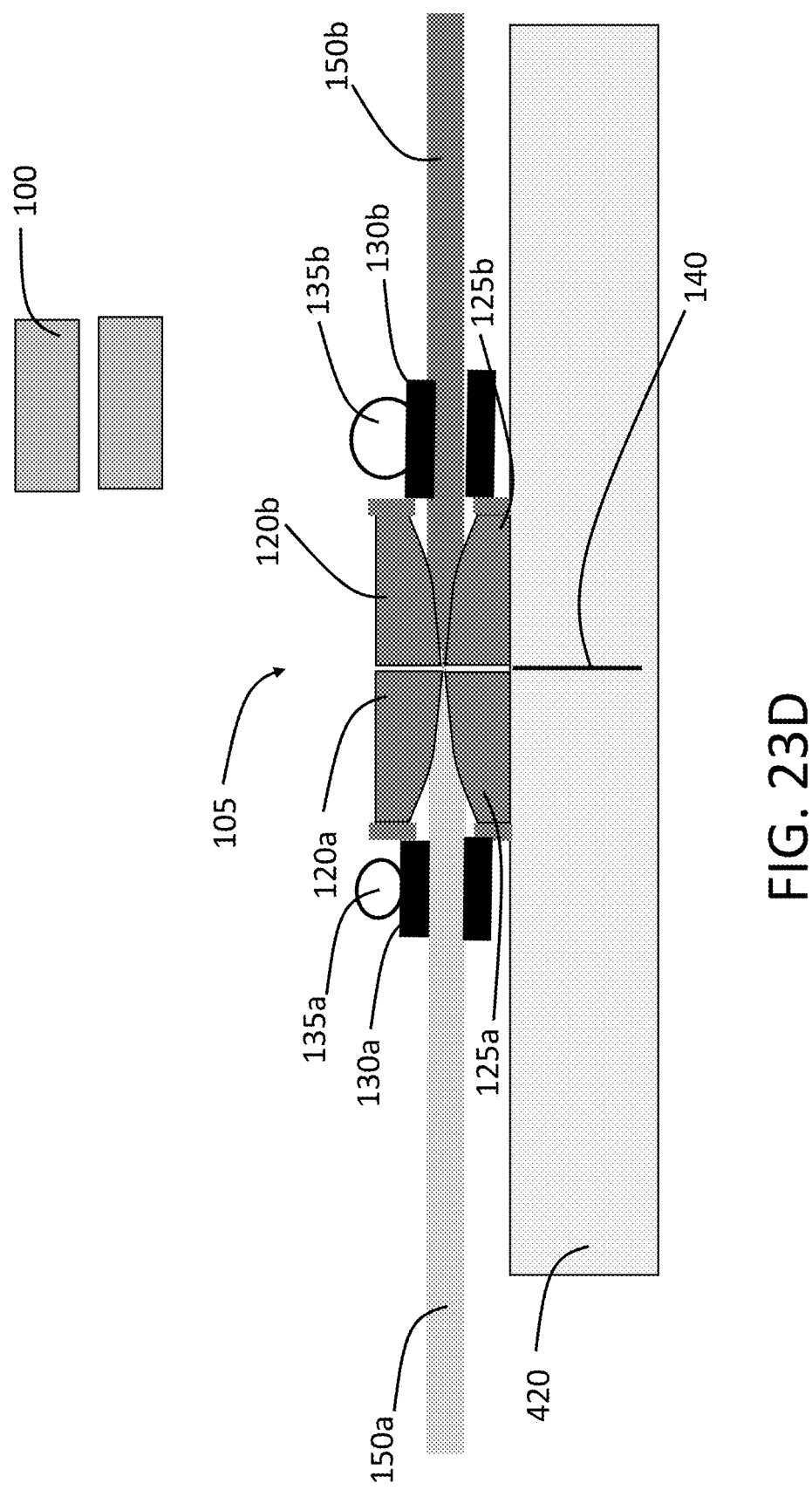
Figure 23E:
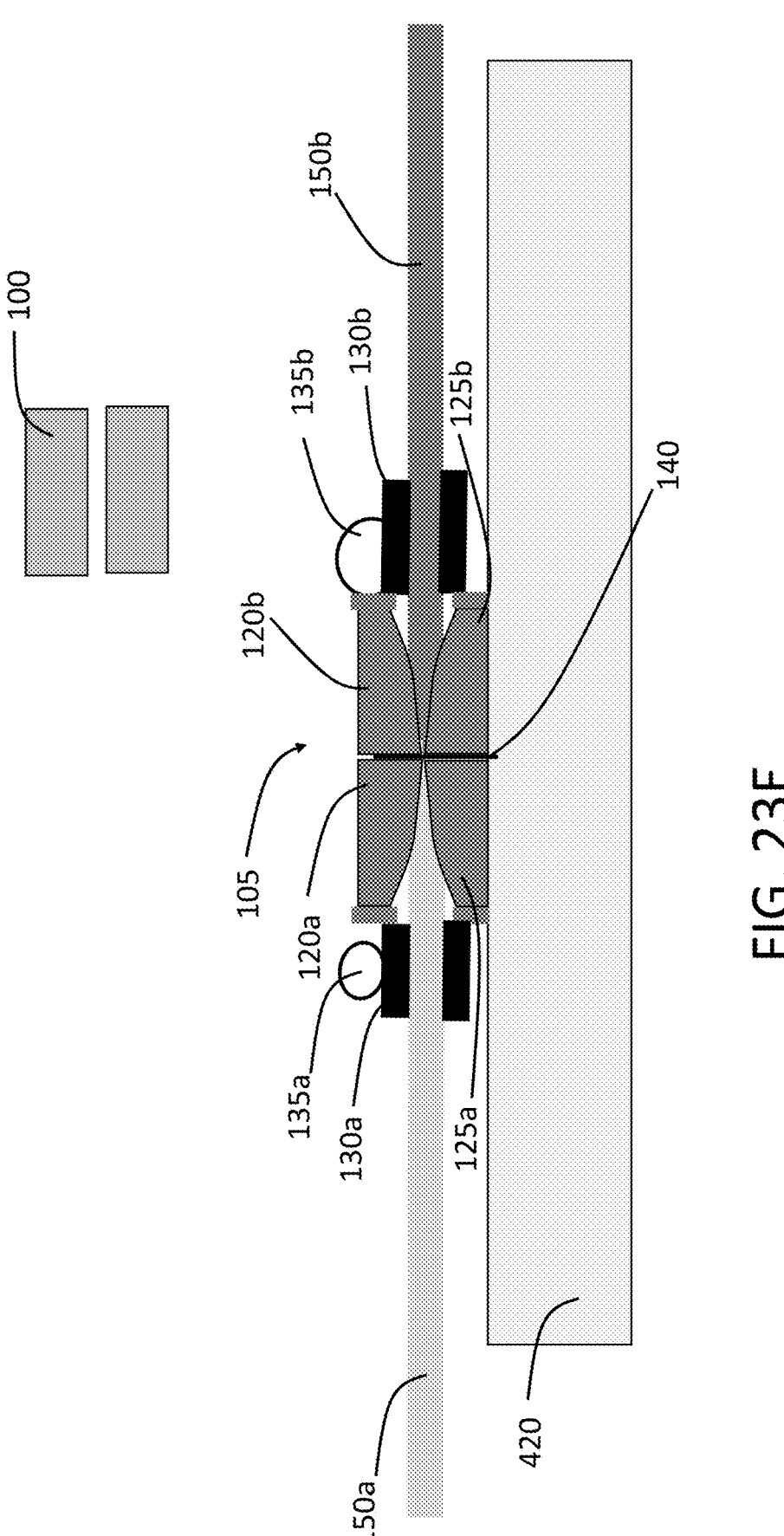
Figure 23F:
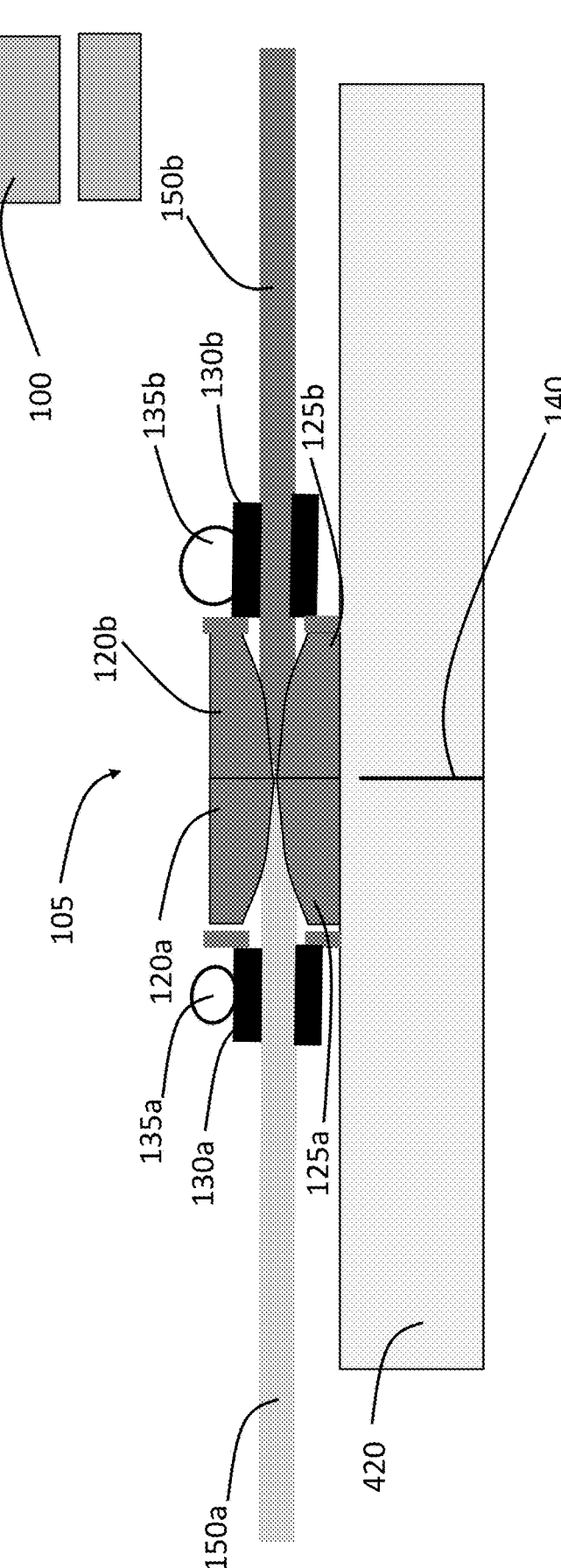
Figure 23G:
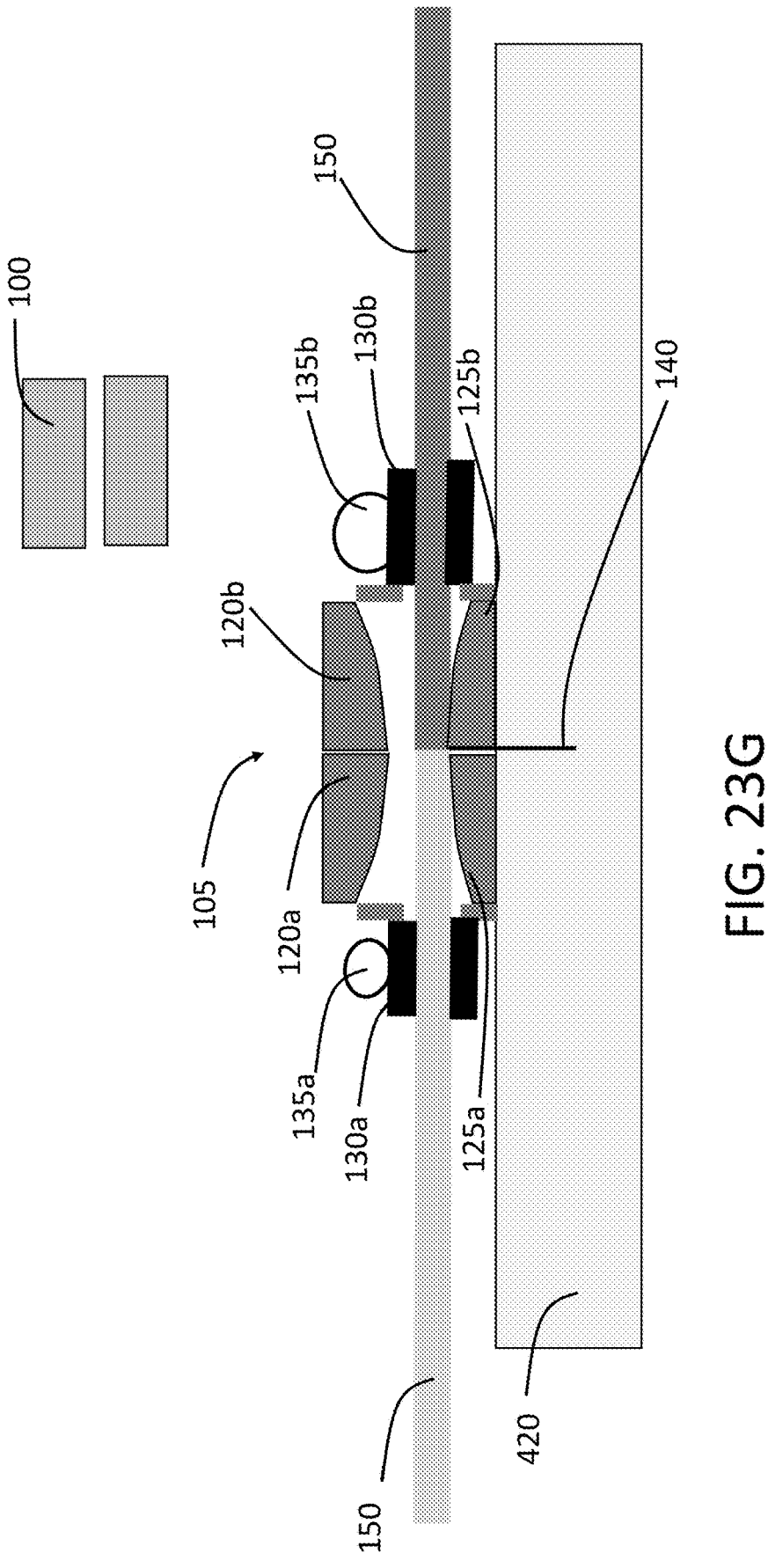
Figure 23H:
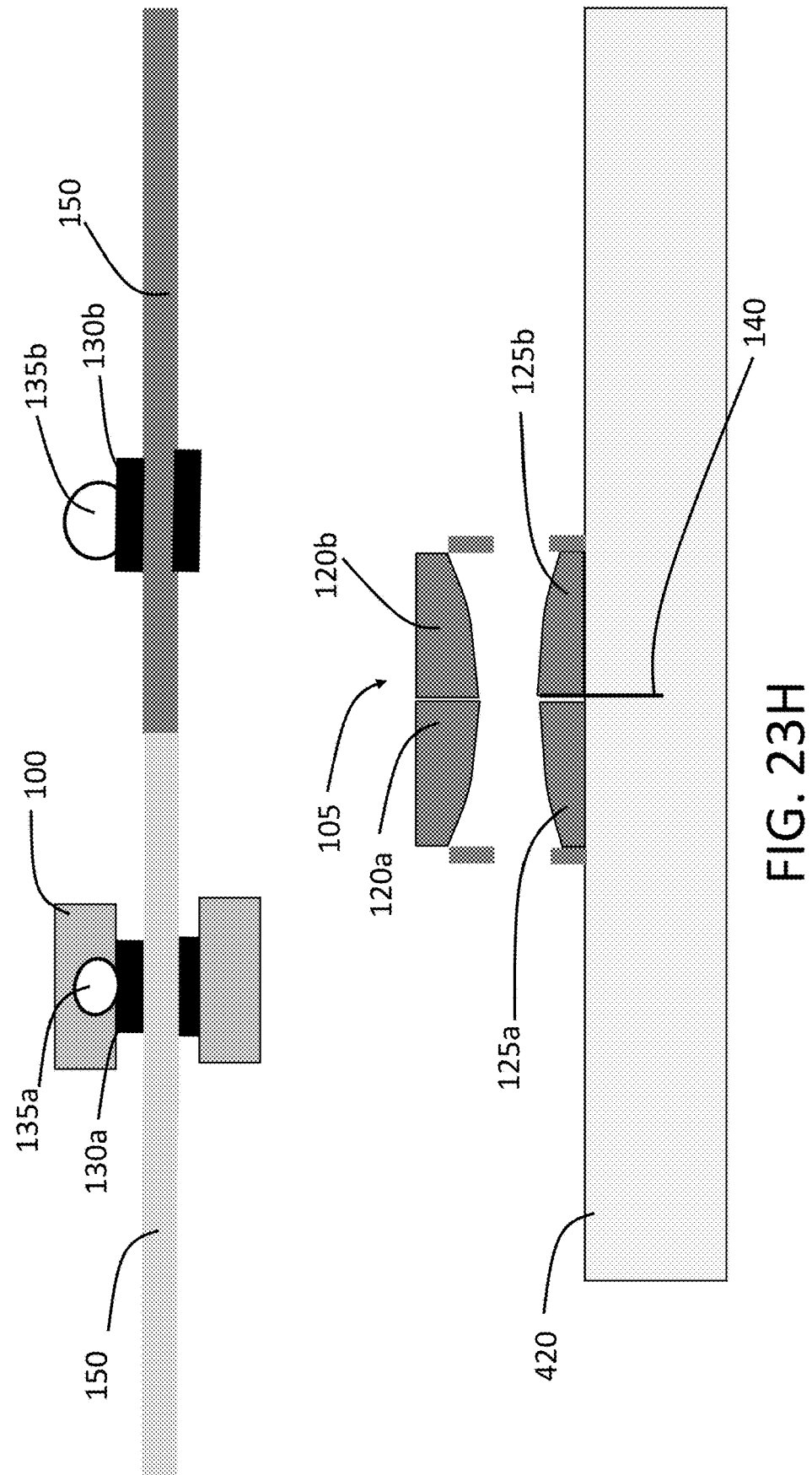

Two end effectors 100 may be used to simultaneously move both tubes 150*a*, 150*b* into the clamping unit 105. In FIG. 23D, the first parts 120*a*, 120*b* of the first jaw 120 move towards the second parts 125*a*, 125*b* of the second jaw 125 to clamp and pinch the tubes 150*a*, 150*b* in the clamping unit 105. In FIG. 23E, the blade 140 cuts through the tubes 150*a*, 150*b*. As previously described, the blade 140 is heated before it cuts the tubes 150*a*, 150*b* and the heat melts the ends of the tubes 150*a*, 150*b*. In FIG. 23F, the blade 140 is removed, and the first parts 120*a*, 125*a* of the clamping unit 105 move relative to the second parts 120*b*, 125*b* of the clamping unit to bring into alignment the tubes 150*a*, 150*b* leading to the respective consumables 13 (not shown). Once the tubes 150*a*, 150*b* are brought into contact, they weld together to form a single tube 150. In FIG. 23G, the first and second parts 120*a*, 120*b* of the first jaw 120 move away from the first and second parts 125*a*, 125*b* of the second jaw 125 to release the tube 150. In FIG. 23H, the end effector 100 holds one of the holders 130*a* to allow the tube 150 to be removed from the clamping unit 105. The tube 150 may then be placed into a pumping unit 30 so that fluid can be pumped through the tube 150.

Figure 24A:
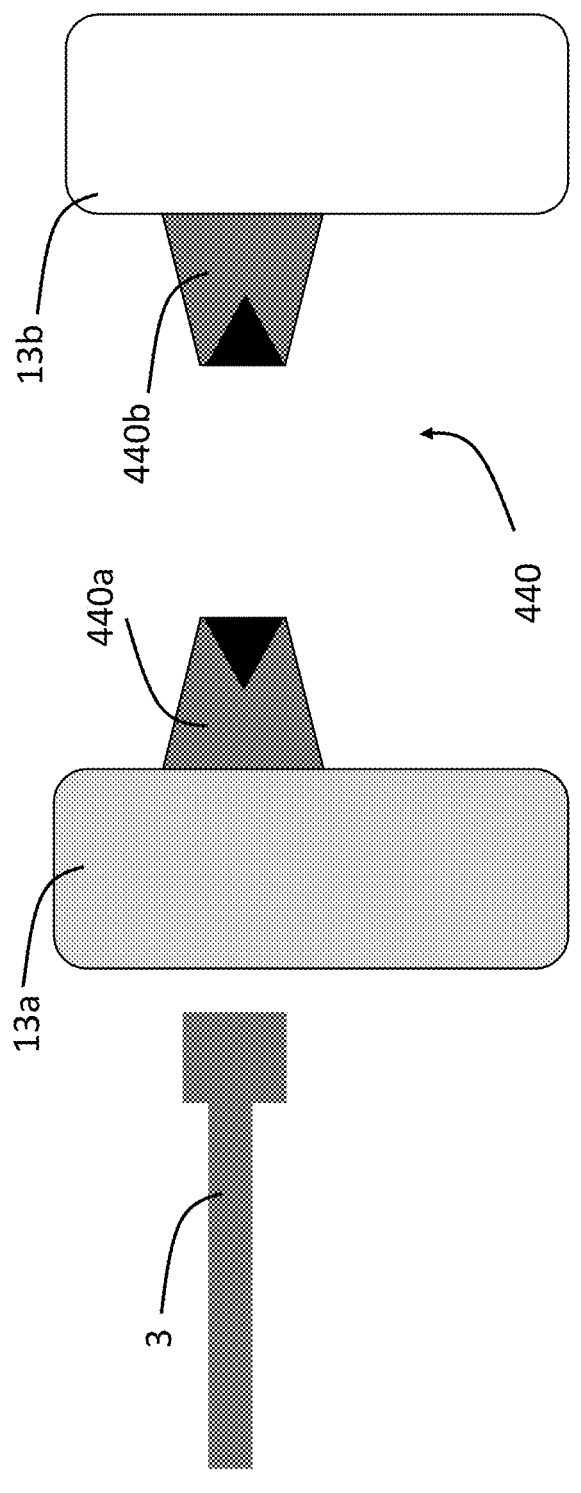
FIGS. 24A to 24C show an embodiment of an apparatus for forming aseptic connections between consumables in the automated bioprocessing system.
Figure 24B:
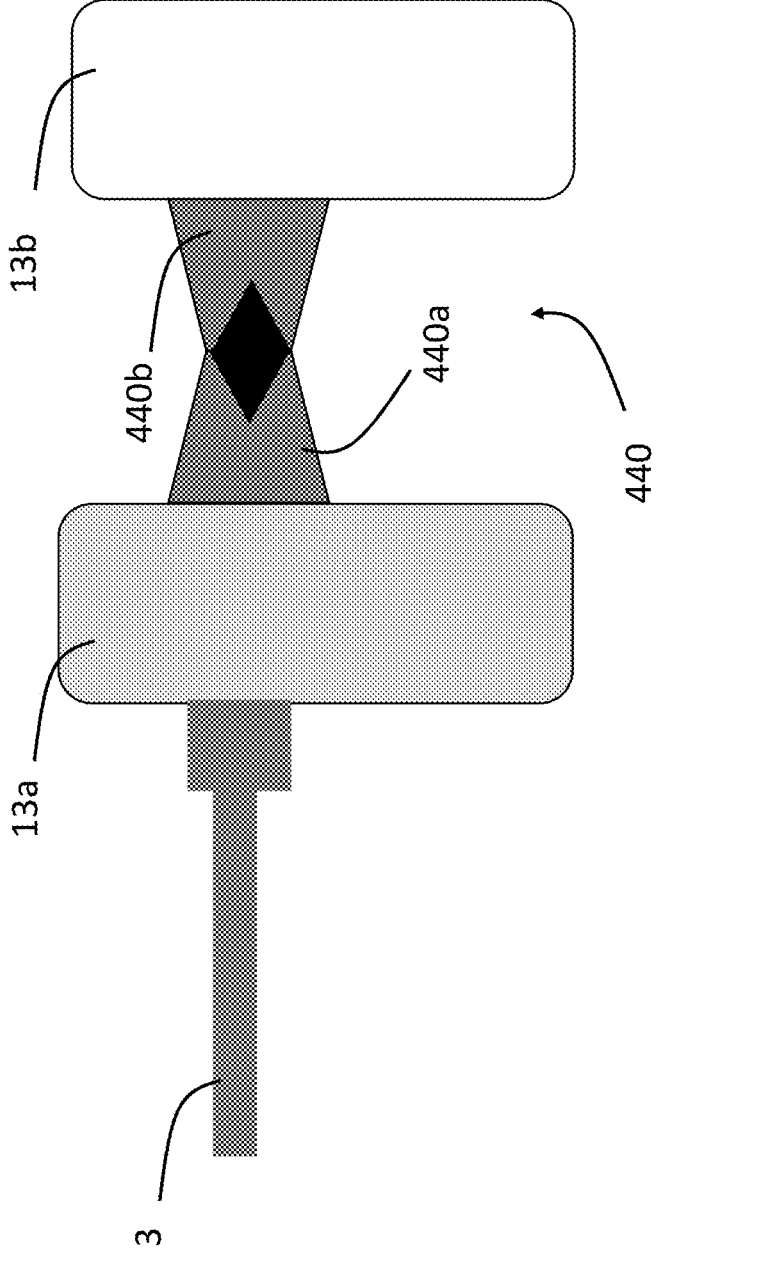
Figure 24C:
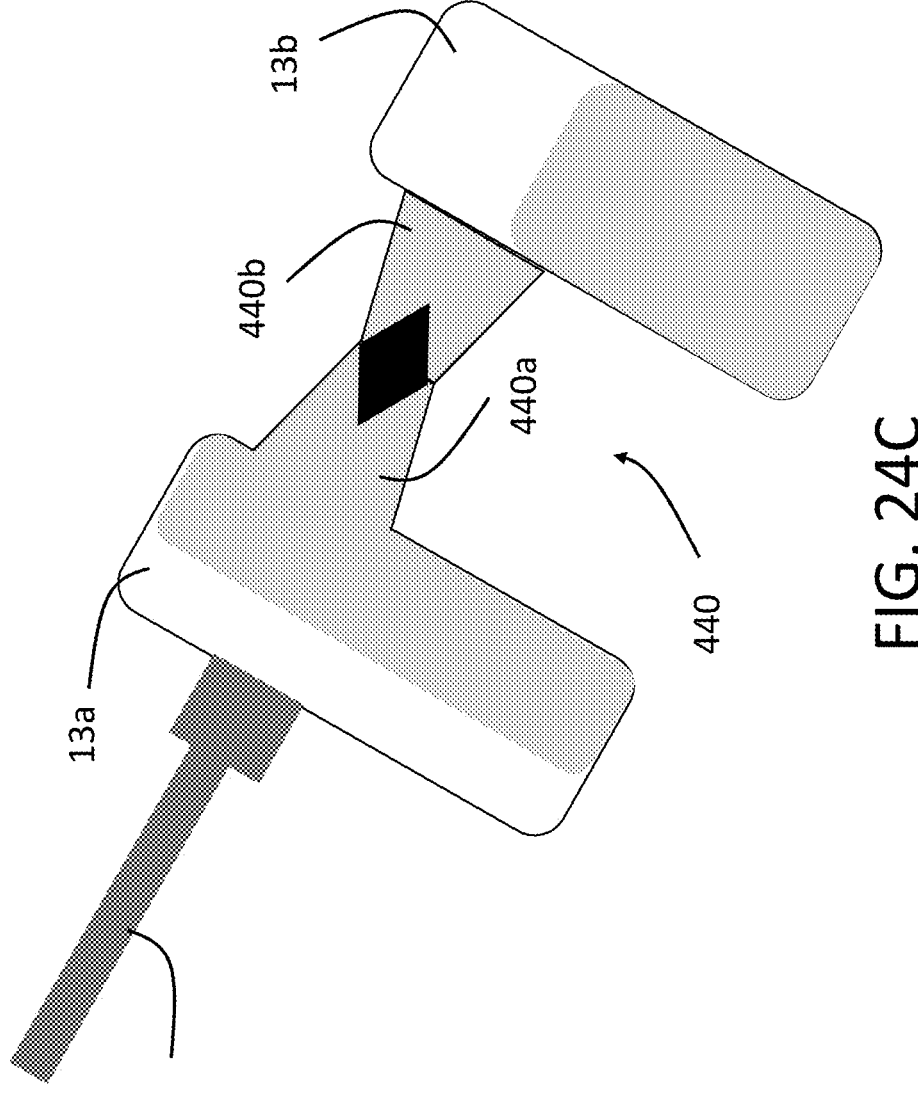

FIG. 24A shows an alternative apparatus for making aseptic connections between containers 13*a*, 13*b* to be connected together using first and second parts 440*a*, 440*b* of an aseptic connector 440 that are each mounted directly to the respective containers 13*a*, 13*b*. A robotic arm 3 is used to hold and manipulate each of the containers 13*a*, 13*b*. These connectors may be any reversible aseptic connector 440, such as the one described in FIG. 20, or a connector with an elastomeric seal. In FIG. 24B, the containers 13*a*, 13*b* have been connected together using the first and second parts 440*a*, 440*b* of the aseptic connector 440, thereby forming a pathway for fluid between the containers 13*a*, 13*b*. In FIG. 24C, the robotic arm 3 tilts the container to allow fluid to flow from container 13*a*, through the aseptic connector, and into container 13*b* under the force of gravity. The containers 13*a*, 13*b*, may have a sterile air filter (not shown) to allow air to fill the containers 13*a*, 13*b* as the fluid moves. Alternatively, collapsible containers such as bags may be used.

It will be appreciated that other reversible connections known in the art may be adapted for use within the bioprocessing (cell therapy) system 1. Such connections may be adapted to have features that are easily handled by the robotic device 2, such as a magnetic collar for easy alignment. It will be appreciated that any feature of a particular embodiment described herein may be applied to another embodiment, in any appropriate combination. It will also be appreciated that particular combinations of the various features described and defined in any aspects described herein can be implemented and/or supplied and/or used independently. Any apparatus feature described herein may also be incorporated as a method feature, and vice versa.

Referring to FIG. 1, the reference numerals indicate the following features:

1000: Cell washing and concentration
1001: Cell starting material
1002: Buffer
1003: Cell washer
1004: Waste
1005: Intermediate material
1010: Activation, transduction, expansion1011: Reagents
1012: Media
1013: Expansion chamber
1014: Waste
1015: Harvest

1020: Fill finish
1021: Final formulation
1022: Mixing chamber
1023: Product bag 1
1024: Product bag 2
1025: Product bag 3
1026: QC bag While the foregoing is directed to exemplary embodiments of the present invention, it will be understood that the present invention is described herein purely by way of example, and modifications of detail can be made within the scope of the invention. Furthermore, one skilled in the art will understand that the present invention may not be limited to the embodiments disclosed herein, or to any details shown in the accompanying figures that are not described in detail herein or defined in the claims. Indeed, such superfluous features may be removed from the figures without prejudice to the present invention.

Moreover, other and further embodiments of the invention will be apparent to those skilled in the art from consideration of the specification, and may be devised without departing from the basic scope thereof, which is determined by the claims that follow.

The invention claimed is:

1. A bioprocessing system, comprising:
a series of processing stations for performing operations for bioprocessing and comprising a first station and a second station;
a first container having a flexible tube connected thereto;
a second container;
a robotic arm;
one or more end effectors; and
a control system programmed to control the robotic arm and the one or more end effectors to:
manipulate the flexible tube of the first container to create a closed aseptic fluid connection between the first container and the second container, the closed aseptic fluid connection enabling a transfer of fluid or cell material between the first container and the second container via the closed aseptic fluid connection;
disconnect, responsive to completion of the transfer of the fluid or cell material between the first container and the second container via the closed aseptic fluid connection, the closed aseptic fluid connections to enable a third container to be connected to the first container; and
move the first container or the second container from the first station to the second station;
wherein the control system is programmed to verify the creation of the closed aseptic fluid connection by controlling the robotic arm and the one or more end effectors to apply a force on a side of the closed aseptic fluid connection, measure a mechanical property, and verify the creation of the closed aseptic fluid connection based on the mechanical property.

2. The bioprocessing system of claim 1, wherein the control system is further programmed to control the robotic arm and the one or more end effectors to seal a disconnected fluid connection, such that the transfer of fluid or cells to or from the first and second containers is inhibited.

3. The bioprocessing system of claim 1, wherein the one or more end effectors comprise a pump operable to pump the fluid or cells between the first container and the second container via the closed aseptic fluid connection.

4. The bioprocessing system of claim 1, further comprising a non-sterile space, wherein the series of processing stations, the first container, the second container, and the robot are positioned in the non-sterile space so as to be exposed to a non- sterile atmosphere.

5. The bioprocessing system of claim 1, further comprising means for inspecting the closed aseptic fluid connection, and wherein the control system comprises one or more processing or control units.

6. The bioprocessing system of claim 1, comprising a sensor, wherein the control system is programmed to verify creation of the closed aseptic fluid connection based on data from the sensor.

7. The bioprocessing system of claim 6, wherein the sensor is a camera, and wherein the control system is programmed to verify the creation of the closed aseptic fluid connection using data from the camera.

8. The bioprocessing system of claim 7, wherein the camera comprises a microscope lens.

9. The bioprocessing system of claim 7, wherein the control system is programmed to use machine vision to identify each of the containers in images from the camera.

10. The bioprocessing system of claim 7, wherein the camera is configured as an infra-red camera.

11. The bioprocessing system of claim 6, the sensor is a fluid sensor or atmospheric sniff sensor configured to detect fluid leakage from the closed aseptic fluid connection when fluid is pumped therethrough.

12. The bioprocessing system of claim 6, wherein the control system is programmed to control the robot to apply pressure or tension to the flexible tube while the sensor collects the data used to verify the creation of the closed aseptic fluid connection.

13. The bioprocessing system of claim 1, wherein the one or more end effectors are a plurality of end effectors, comprising different types of end effectors, and wherein the robotic arm is configured to selectively engage with the plurality of end effectors.

14. The bioprocessing system of claim 1, wherein the first station and the second station are one or more types of stations from a set comprising a concentration station for performing concentrations, a washing station for washing, and an incubator for performing incubation.

15. The bioprocessing system of claim 1, wherein the control system is programmed to control the robotic arm and the one or more end effectors according to a first workflow when if the first container contains a first patient sample and a second workflow if the first container contains a second patient sample, the first workflow different than the second workflow.

16. The bioprocessing system of claim 1, wherein the flexible tube of the first container is a first flexible tube, wherein the second container has a second flexible tube connected thereto, and wherein the control system is programmed to control the robotic arm and the one or more end effectors to manipulate both the first flexible tube and the second flexible tube to create the closed aseptic fluid connection.

17. The bioprocessing system of claim 16, wherein the one or more end effectors comprise a tube welder configured to join the first tube to the second tube by removing an end portion of each of the first and second tubes prior to welding them together thereby to form a sterile tube weld between the first and second tubes, wherein the control system is programmed to control the robotic arm and the one or more end effectors to create the close aseptic connection by controlling the tube welder.

18. The bioprocessing system of claim 17, wherein the robotic arm comprises a gripping unit configured to selectively engage with the one or more end effectors, the one or more end effectors comprising a tube welder and a pumping unit.

19. A bioprocessing system, comprising:

a series of processing stations for performing operations for bioprocessing and comprising a first station and a second station;

a first container having a flexible tube connected thereto;

a second container;

a robotic arm;

one or more end effectors, wherein the robotic arm comprises a gripping unit configured to selectively engage with the one or more end effectors, the one or more end effectors comprising a tube welder and a pumping unit; and a control system programmed to control the robotic arm and the one or more end effectors to:

manipulate the flexible tube of the first container to create a closed aseptic fluid connection between the first container and the second container, the closed aseptic fluid connection enabling a transfer of fluid or cell material between the first container and the second container via the closed aseptic fluid connection;

disconnect, responsive to completion of the transfer of the fluid or cell material between the first container and the second container via the closed aseptic fluid connection, the closed aseptic fluid connections to enable a third container to be connected to the first container; and move the first container or the second container from the first station to the second station.

20. A bioprocessing system, comprising:

a series of processing stations for performing operations for bioprocessing and comprising a first station and a second station;

a first container having a flexible tube connected thereto;

a second container;

a robotic arm;

one or more end effectors; and a control system programmed to control the robotic arm and the one or more end effectors to:

manipulate the flexible tube of the first container to create a closed aseptic fluid connection between the first container and the second container, the closed aseptic fluid connection enabling a transfer of fluid or cell material between the first container and the second container via the closed aseptic fluid connection;

disconnect, responsive to completion of the transfer of the fluid or cell material between the first container and the second container via the closed aseptic fluid connection, the closed aseptic fluid connections to enable a third container to be connected to the first container; and move the first container or the second container from the first station to the second station;

wherein the one or more end effectors comprise a pump operable to pump the fluid or cells between the first container and the second container via the closed aseptic fluid connection.

* * * * *